US006431707B1

(12) United States Patent
Jordan et al.

(10) Patent No.: US 6,431,707 B1
(45) Date of Patent: Aug. 13, 2002

(54) MATERIALS AND METHODS FOR DETECTION OR MONITORING OF NEOPLASTIC DISEASE

(76) Inventors: Berry Jordan, 435 NW. 50$^{th}$ Blvd., Gainesville, FL (US) 32607; Ting Fang, 158 30th St., New Orleans, LA (US) 70124

( * ) Notice: Subject to any disclaimer, the term of this patent is extended or adjusted under 35 U.S.C. 154(b) by 0 days.

(21) Appl. No.: 09/462,250

(22) PCT Filed: May 6, 1999

(86) PCT No.: PCT/US99/09899

§ 371 (c)(1), (2), (4) Date: Mar. 6, 2000

(87) PCT Pub. No.: WO99/56610

PCT Pub. Date: Nov. 11, 1999

Related U.S. Application Data

(60) Provisional application No. 60/084,417, filed on May 6, 1998.

(51) Int. Cl.[7] .................................................. A61B 3/10

(52) U.S. Cl. ...................................................... 351/200

(58) Field of Search ................................ 435/7.2, 7.21, 435/7.92; 436/506, 63, 64, 813; 530/350, 413, 417; 351/205, 206, 222, 246

(56) References Cited

U.S. PATENT DOCUMENTS 5,405,749 A * 4/1995 Polans et al. .............. 435/7.23

OTHER PUBLICATIONS

C. E. Thirkill et al., "The Cancer Connection: The Retinal CAR Antigen is Expressed in Small Cell Carcinoma of the Lung," Invest. Ophthal. Vis. Sci., 33(4): 847 (1992).*

Jordan, B.L., W.W. Dawson, T. Fang (1998) "Functional Retinal Abnormalities Among Cancer Patients" *Invest Opthalmol Vis Sci* 39(4):S402.

Dawson, W., B. Jordan, K. Hazariwala, T. Fang, R. Marsh "Electroretinography and Psychophysics in cancer associated retinal deficit (CARD) Syndrome" presented in Prague, Czech Republic at annual ISEV meeting, spring 1998.

Posner, Jerome B., Josep Dalmau (1995) "Clinical enigmas of paraneoplastic neurologic disorders" *Clinical Neurology and Neurosurgery* 97:61–70.

Alarcón–Segovia, Donato, Alejandro Ruiz–Argüelles and Luis Llorente (1996) "Broken dogma: penetration of autoantibodies into living cells" *Immunology Today* 17(4):163–164.

Darnell, Robert B. (1996) "Onconeural antigens and the paraneoplastic neurologic disorders: At the intersection of cancer, immunity, and the brain" *Proc. Natl. Acad. Sci. USA* 93:4529–4536.

Korngruth, S.E. (1989) "Neuronal Proteins and Paraneoplastic Syndromes" *N. Eng. J. Med* 321(23):1607–1608.

* cited by examiner

*Primary Examiner*—George Manuel
(74) *Attorney, Agent, or Firm*—Saliwanchik, Lloyd & Saliwanchik

(57) ABSTRACT

The subject invention provides a method for early detection of cancer. More specifically, the subject invention concerns a non-invasive test whereby retinal dysfunctions are correlated with the presence of neoplastic disease.

28 Claims, 48 Drawing Sheets

| PATIENT 1: | | See Table 1 #11 | |
|---|---|---|---|
| DOT m/d/y | | AGE | 66 |
| 1/15/98 | 1st EYE | 2nd EYE | |
| EYE | RIGHT | left | |
| Reference | PLACEMEN | PLACEMENT | |
| cap position | cap position | cap position | |
| 85 | 2 | 1 | |
| 1 | 85 | 5 | |
| 2 | 1 | 7 | |
| 3 | 3 | 85 | |
| 4 | 5 | 4 | |
| 5 | 4 | 3 | |
| 6 | 6 | 2 | |
| 7 | 7 | 6 | |
| 8 | 8 | 8 | |
| 9 | 9 | 9 | |
| 10 | 10 | 11 | |
| 11 | 11 | 10 | |
| 12 | 12 | 15 | |
| 13 | 14 | 12 | |
| 14 | 13 | 13 | |
| 15 | 15 | 14 | |
| 16 | 16 | 16 | |
| 17 | 19 | 17 | |
| 18 | 18 | 19 | |
| 19 | 17 | 18 | |
| 20 | 21 | 21 | |
| 21 | 20 | 20 | |

| PATIENT 2: | | See Table 3 #6 | |
|---|---|---|---|
| DOT m/d/y | | AGE | 41 |
| 2/3/98 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 1 | 1 | |
| 2 | 2 | 2 | |
| 3 | 3 | 3 | |
| 4 | 5 | 4 | |
| 5 | 4 | 5 | |
| 6 | 6 | 6 | |
| 7 | 7 | 7 | |
| 8 | 8 | 8 | |
| 9 | 9 | 9 | |
| 10 | 10 | 10 | |
| 11 | 11 | 11 | |
| 12 | 12 | 12 | |
| 13 | 13 | 13 | |
| 14 | 14 | 14 | |
| 15 | 15 | 15 | |
| 16 | 17 | 16 | |
| 17 | 16 | 17 | |
| 18 | 18 | 18 | |
| 19 | 20 | 20 | |
| 20 | 19 | 19 | |
| 21 | 21 | 21 | |

| PATIENT 3: | | See Table 1 #15 | |
|---|---|---|---|
| DOT m/d/y | | AGE | 41 |
| 1/13/98 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 1 | 1 | |
| 2 | 2 | 2 | |
| 3 | 3 | 3 | |
| 4 | 4 | 4 | |
| 5 | 5 | 5 | |
| 6 | 6 | 6 | |
| 7 | 7 | 7 | |
| 8 | 9 | 9 | |
| 9 | 8 | 8 | |
| 10 | 11 | 10 | |
| 11 | 10 | 11 | |
| 12 | 12 | 12 | |
| 13 | 14 | 14 | |
| 14 | 13 | 15 | |
| 15 | 15 | 13 | |
| 16 | 17 | 16 | |
| 17 | 16 | 17 | |
| 18 | 18 | 18 | |
| 19 | 19 | 19 | |
| 20 | 20 | 20 | |
| 21 | 21 | 21 | |

FIG. 7A-1

| | | | | | | | | |
|---|---|---|---|---|---|---|---|---|
| 22 | 24 | 25 | 22 | 22 | 22 | 22 | 23 | 22 |
| 23 | 26 | 28 | 23 | 23 | 23 | 23 | 22 | 23 |
| 24 | 23 | 22 | 24 | 24 | 24 | 24 | 24 | 24 |
| 25 | 25 | 23 | 25 | 25 | 25 | 25 | 26 | 25 |
| 26 | 22 | 24 | 26 | 26 | 26 | 26 | 25 | 28 |
| 27 | 27 | 26 | 27 | 27 | 27 | 27 | 27 | 29 |
| 28 | 30 | 29 | 28 | 28 | 29 | 28 | 30 | 26 |
| 29 | 28 | 27 | 29 | 29 | 30 | 29 | 28 | 27 |
| 30 | 29 | 31 | 30 | 31 | 28 | 30 | 29 | 30 |
| 31 | 31 | 32 | 31 | 30 | 31 | 31 | 32 | 32 |
| 32 | 32 | 30 | 32 | 32 | 32 | 32 | 31 | 31 |
| 33 | 34 | 36 | 33 | 33 | 33 | 33 | 34 | 34 |
| 34 | 37 | 35 | 34 | 34 | 34 | 34 | 33 | 35 |
| 35 | 35 | 37 | 35 | 35 | 35 | 35 | 35 | 33 |
| 36 | 33 | 34 | 36 | 36 | 36 | 36 | 36 | 37 |
| 37 | 39 | 39 | 37 | 37 | 37 | 37 | 37 | 36 |
| 38 | 38 | 40 | 38 | 38 | 38 | 38 | 38 | 38 |
| 39 | 42 | 41 | 39 | 39 | 40 | 39 | 40 | 39 |
| 40 | 36 | 33 | 40 | 40 | 39 | 40 | 39 | 40 |
| 41 | 40 | 38 | 41 | 42 | 42 | 41 | 42 | 41 |
| 42 | 41 | 42 | 42 | 41 | 41 | 42 | 41 | 42 |
| 43 | 45 | 50 | 43 | 43 | 43 | 43 | 43 | 43 |
| 44 | 43 | 44 | 44 | 46 | 44 | 44 | 44 | 45 |
| 45 | 44 | 43 | 45 | 45 | 46 | 45 | 48 | 44 |

FIG. 7A-2

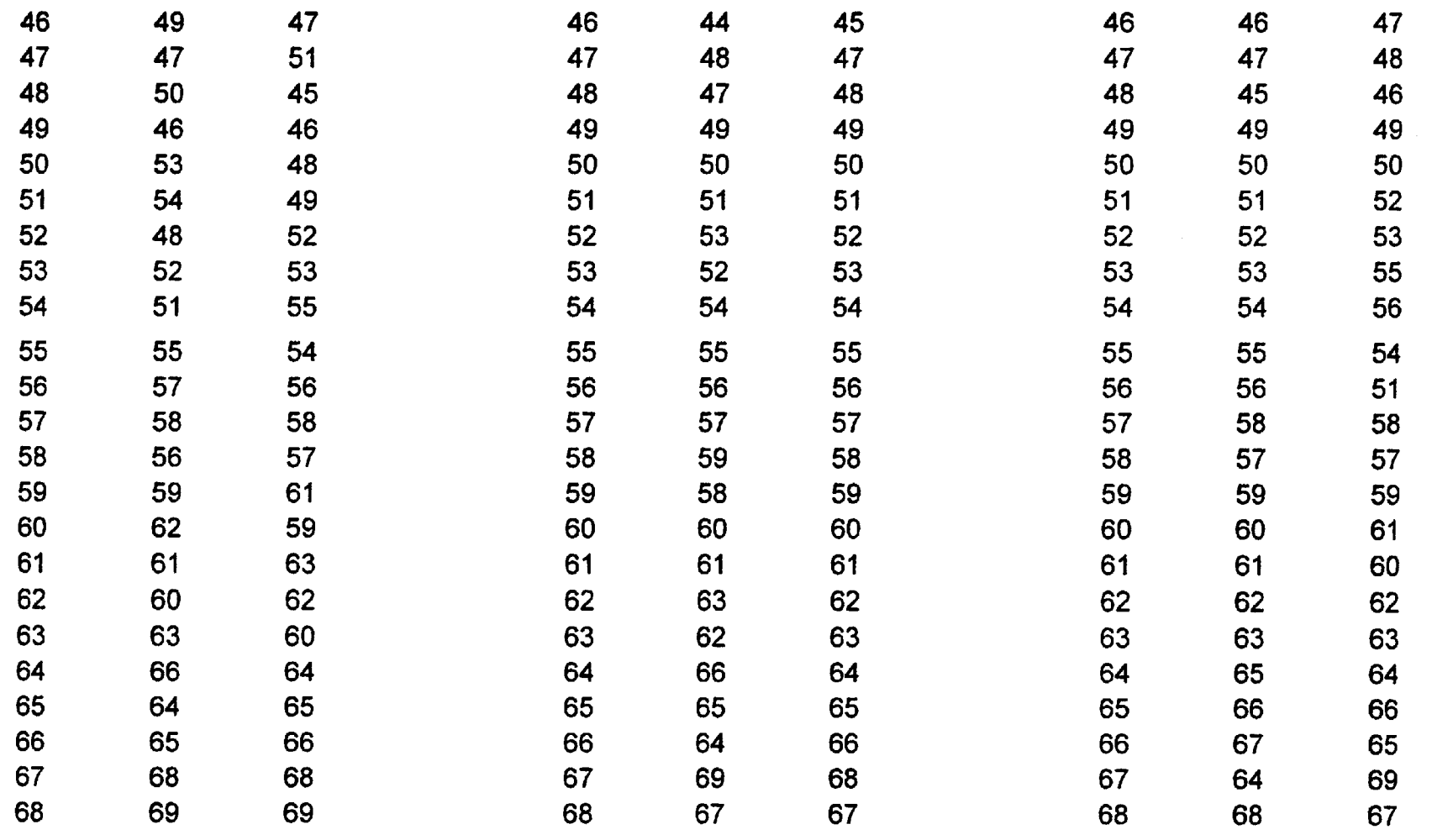

| | | | | | | | | |
|---|---|---|---|---|---|---|---|---|
| 46 | 49 | 47 | 46 | 44 | 45 | 46 | 46 | 47 |
| 47 | 47 | 51 | 47 | 48 | 47 | 47 | 47 | 48 |
| 48 | 50 | 45 | 48 | 47 | 48 | 48 | 45 | 46 |
| 49 | 46 | 46 | 49 | 49 | 49 | 49 | 49 | 49 |
| 50 | 53 | 48 | 50 | 50 | 50 | 50 | 50 | 50 |
| 51 | 54 | 49 | 51 | 51 | 51 | 51 | 51 | 52 |
| 52 | 48 | 52 | 52 | 53 | 52 | 52 | 52 | 53 |
| 53 | 52 | 53 | 53 | 52 | 53 | 53 | 53 | 55 |
| 54 | 51 | 55 | 54 | 54 | 54 | 54 | 54 | 56 |
| 55 | 55 | 54 | 55 | 55 | 55 | 55 | 55 | 54 |
| 56 | 57 | 56 | 56 | 56 | 56 | 56 | 56 | 51 |
| 57 | 58 | 58 | 57 | 57 | 57 | 57 | 58 | 58 |
| 58 | 56 | 57 | 58 | 59 | 58 | 58 | 57 | 57 |
| 59 | 59 | 61 | 59 | 58 | 59 | 59 | 59 | 59 |
| 60 | 62 | 59 | 60 | 60 | 60 | 60 | 60 | 61 |
| 61 | 61 | 63 | 61 | 61 | 61 | 61 | 61 | 60 |
| 62 | 60 | 62 | 62 | 63 | 62 | 62 | 62 | 62 |
| 63 | 63 | 60 | 63 | 62 | 63 | 63 | 63 | 63 |
| 64 | 66 | 64 | 64 | 66 | 64 | 64 | 65 | 64 |
| 65 | 64 | 65 | 65 | 65 | 65 | 65 | 66 | 66 |
| 66 | 65 | 66 | 66 | 64 | 66 | 66 | 67 | 65 |
| 67 | 68 | 68 | 67 | 69 | 68 | 67 | 64 | 69 |
| 68 | 69 | 69 | 68 | 67 | 67 | 68 | 68 | 67 |

FIG. 7A-3

| | | | | | | | | |
|---|---|---|---|---|---|---|---|---|
| 69 | 70 | 67 | 69 | 68 | 70 | 69 | 69 | 68 |
| 70 | 67 | 70 | 70 | 71 | 69 | 70 | 70 | 70 |
| 71 | 71 | 71 | 71 | 70 | 71 | 71 | 72 | 72 |
| 72 | 72 | 72 | 72 | 73 | 72 | 72 | 71 | 71 |
| 73 | 79 | 73 | 73 | 72 | 73 | 73 | 73 | 73 |
| 74 | 76 | 76 | 74 | 74 | 74 | 74 | 74 | 76 |
| 75 | 73 | 75 | 75 | 77 | 75 | 75 | 75 | 74 |
| 76 | 81 | 74 | 76 | 76 | 76 | 76 | 78 | 75 |
| 77 | 74 | 78 | 77 | 75 | 77 | 77 | 76 | 79 |
| 78 | 77 | 77 | 78 | 80 | 78 | 78 | 77 | 77 |
| 79 | 82 | 80 | 79 | 78 | 79 | 79 | 80 | 78 |
| 80 | 80 | 82 | 80 | 79 | 80 | 80 | 79 | 80 |
| 81 | 83 | 81 | 81 | 81 | 81 | 81 | 82 | 81 |
| 82 | 84 | 79 | 82 | 82 | 82 | 82 | 81 | 82 |
| 83 | 75 | 83 | 83 | 83 | 83 | 83 | 83 | 84 |
| 84 | 78 | 84 | 84 | 84 | 84 | 84 | 84 | 83 |

FIG. 7A-4

See Table 1 #11

| | | |
|---|---|---|
| age | 66 | |
| Error score | 292 | 260 |
| Mean error | 5.435294 | 5.058824 |
| SQRT of error | 17.08801 | 16.12452 |
| B+Y SQRT | 13.71131 | 12.04159 |
| R+G SQRT | 11.22497 | 10.34408 |
| Quad. axis | 2.486337 | 1.697514 |
| BINOCULARLY NORMAL | | |
| On eye to eye comparison | | |
| 0.713491994 | | |
| Box 1 SQRT | 6 | 7.549834 |
| Box 2 SQRT | 8.42615 | 9.539392 |
| Box 3 SQRT | 8.774964 | 8.3666 |
| Box 4 SQRT | 10.3923 | 6.480741 |
| Amp. sine | 1.666321 | 0.931422 |
| C.M.A. | 78.8451 | 84.1179 |
| | 36.34163 | 41.61442 |
| dev. +/- | 1.581381 | 2.826288 |
| beta | 0.306574 | 0.184118 |
| M.S.E. | 6.450184 | 6.437355 |
| S.E.(A) | 0.389575 | 0.389188 |

See Table 3 #6

| | | |
|---|---|---|
| age | 41 | |
| Error score | 84 | 32 |
| Mean error | 2.988235 | 2.376471 |
| SQRT of error | 9.165151 | 5.656854 |
| B+Y SQRT | 6.480741 | 3.464102 |
| R+G SQRT | 7.071068 | 4.472136 |
| Quad. axis | -0.59033 | -1.00803 |
| 95% BINOC ERROR | | |
| On eye to eye comparison | | |
| 3.25829714 | | |
| Box 1 SQRT | 3.464102 | 2 |
| Box 2 SQRT | 3.162278 | 4 |
| Box 3 SQRT | 5.196152 | 2 |
| Box 4 SQRT | 5.91608 | 2.828427 |
| Amp. sine | 0.326247 | 0.279203 |
| C.M.A. | 70.80964 | 73.24586 |
| | 28.30616 | 30.74238 |
| dev. +/- | 3.691149 | 2.344494 |
| beta | 0.109177 | 0.117487 |
| M.S.E. | 1.34709 | 0.398035 |
| S.E.(A) | 0.178034 | 0.096776 |

See Table 1 #15

| | | |
|---|---|---|
| age | 41 | |
| Error score | 100 | 116 |
| Mean error | 3.176471 | 3.364706 |
| SQRT of erro | 10 | 10.77033 |
| B+Y SQRT | 7.681146 | 7.483315 |
| R+G SQRT | 7.071068 | 7.937254 |
| Quad. axis | 0.610078 | -0.45394 |
| BINOCULARLY NORMAL | | |
| On eye to eye comparison | | |
| 1.020329614 | | |
| Box 1 SQRT | 4.242641 | 3.464102 |
| Box 2 SQRT | 5.477226 | 5.385165 |
| Box 3 SQRT | 5.09902 | 6.324555 |
| Box 4 SQRT | 5.09902 | 5.91608 |
| Amp. sine | 0.310174 | 0.225952 |
| C.M.A. | 74.97126 | 70.78569 |
| | 32.46778 | 28.28221 |
| dev. +/- | 3.548246 | 6.364388 |
| beta | 0.097647 | 0.067154 |
| M.S.E. | 1.125171 | 1.920997 |
| S.E.(A) | 0.16271 | 0.212603 |

FIG. 7A-5

| PATIENT 4: | | Table 3 #8 | |
|---|---|---|---|
| DOT m/d/y | | AGE | 60 |
| 6/17/98 | 1st EYE | 2nd EYE | |
| EYE | RIGHT | left | |
| Reference cap position | PLACEMEN cap position | PLACEMENT cap position | |
| 85 | 1 | 85 | |
| 1 | 85 | 1 | |
| 2 | 2 | 2 | |
| 3 | 3 | 3 | |
| 4 | 4 | 4 | |
| 5 | 5 | 6 | |
| 6 | 6 | 5 | |
| 7 | 8 | 7 | |
| 8 | 7 | 8 | |
| 9 | 10 | 9 | |
| 10 | 9 | 11 | |
| 11 | 12 | 10 | |
| 12 | 11 | 12 | |
| 13 | 13 | 14 | |
| 14 | 14 | 13 | |
| 15 | 15 | 15 | |
| 16 | 17 | 16 | |
| 17 | 16 | 17 | |
| 18 | 18 | 18 | |
| 19 | 21 | 20 | |
| 20 | 19 | 19 | |
| 21 | 20 | 21 | |

| PATIENT 5: | | Table 3 #10 | |
|---|---|---|---|
| DOT m/d/y | | AGE | 44 |
| 6/25/98 | 1st EYE | 2nd EYE | |
| EYE | RIGHT | left | |
| Reference cap position | PLACEMEN cap position | PLACEMENT cap position | |
| 85 | 85 | 85 | |
| 1 | 1 | 1 | |
| 2 | 2 | 2 | |
| 3 | 3 | 3 | |
| 4 | 5 | 4 | |
| 5 | 4 | 5 | |
| 6 | 6 | 8 | |
| 7 | 7 | 6 | |
| 8 | 8 | 7 | |
| 9 | 10 | 9 | |
| 10 | 9 | 10 | |
| 11 | 13 | 11 | |
| 12 | 12 | 12 | |
| 13 | 14 | 14 | |
| 14 | 11 | 15 | |
| 15 | 15 | 13 | |
| 16 | 16 | 17 | |
| 17 | 18 | 16 | |
| 18 | 17 | 21 | |
| 19 | 19 | 18 | |
| 20 | 21 | 19 | |
| 21 | 20 | 20 | |

| PATIENT 6: | | Table 3 #9 | |
|---|---|---|---|
| DOT m/d/y | | AGE | 42 |
| 10/31/97 | 1st EYE | 2nd EYE | |
| EYE | left | right | |
| Reference cap position | PLACEMEN cap position | PLACEMENT cap position | |
| 85 | 85 | 85 | |
| 1 | 2 | 1 | |
| 2 | 1 | 2 | |
| 3 | 3 | 3 | |
| 4 | 5 | 4 | |
| 5 | 4 | 5 | |
| 6 | 6 | 6 | |
| 7 | 8 | 7 | |
| 8 | 7 | 8 | |
| 9 | 9 | 9 | |
| 10 | 10 | 10 | |
| 11 | 11 | 11 | |
| 12 | 12 | 12 | |
| 13 | 14 | 13 | |
| 14 | 13 | 14 | |
| 15 | 15 | 15 | |
| 16 | 17 | 16 | |
| 17 | 16 | 17 | |
| 18 | 18 | 18 | |
| 19 | 20 | 19 | |
| 20 | 21 | 21 | |
| 21 | 19 | 20 | |

FIG. 7B-1

| | | | | | | | | |
|---|---|---|---|---|---|---|---|---|
| 22 | 25 | 22 | 22 | 22 | 23 | 22 | 22 | 22 |
| 23 | 23 | 23 | 23 | 23 | 25 | 23 | 23 | 23 |
| 24 | 22 | 26 | 24 | 24 | 24 | 24 | 24 | 24 |
| 25 | 26 | 25 | 25 | 26 | 22 | 25 | 25 | 25 |
| 26 | 24 | 24 | 26 | 25 | 26 | 26 | 27 | 26 |
| 27 | 27 | 27 | 27 | 27 | 27 | 27 | 26 | 28 |
| 28 | 28 | 31 | 28 | 28 | 28 | 28 | 29 | 27 |
| 29 | 29 | 28 | 29 | 29 | 29 | 29 | 30 | 29 |
| 30 | 31 | 30 | 30 | 30 | 32 | 30 | 28 | 31 |
| 31 | 30 | 29 | 31 | 31 | 33 | 31 | 31 | 30 |
| 32 | 32 | 32 | 32 | 32 | 31 | 32 | 33 | 32 |
| 33 | 33 | 33 | 33 | 34 | 30 | 33 | 32 | 33 |
| 34 | 35 | 35 | 34 | 35 | 34 | 34 | 34 | 34 |
| 35 | 34 | 34 | 35 | 33 | 35 | 35 | 35 | 35 |
| 36 | 36 | 36 | 36 | 37 | 36 | 36 | 36 | 37 |
| 37 | 39 | 39 | 37 | 38 | 38 | 37 | 38 | 36 |
| 38 | 37 | 37 | 38 | 36 | 37 | 38 | 37 | 38 |
| 39 | 38 | 40 | 39 | 39 | 39 | 39 | 39 | 39 |
| 40 | 40 | 38 | 40 | 42 | 40 | 40 | 40 | 40 |
| 41 | 41 | 41 | 41 | 41 | 42 | 41 | 41 | 42 |
| 42 | 42 | 42 | 42 | 40 | 41 | 42 | 42 | 41 |
| 43 | 44 | 43 | 43 | 44 | 43 | 43 | 43 | 43 |
| 44 | 43 | 45 | 44 | 43 | 44 | 44 | 45 | 45 |
| 45 | 45 | 44 | 45 | 45 | 46 | 45 | 47 | 44 |

FIG. 7B-2

| | | | | | | | | |
|---|---|---|---|---|---|---|---|---|
| 46 | 47 | 46 | 46 | 48 | 45 | 46 | 46 | 46 |
| 47 | 46 | 48 | 47 | 47 | 47 | 47 | 44 | 48 |
| 48 | 49 | 47 | 48 | 49 | 48 | 48 | 48 | 47 |
| 49 | 50 | 49 | 49 | 46 | 49 | 49 | 49 | 49 |
| 50 | 48 | 51 | 50 | 53 | 50 | 50 | 50 | 50 |
| 51 | 53 | 50 | 51 | 50 | 53 | 51 | 53 | 51 |
| 52 | 51 | 54 | 52 | 52 | 51 | 52 | 51 | 52 |
| 53 | 55 | 55 | 53 | 51 | 54 | 53 | 52 | 54 |
| 54 | 52 | 53 | 54 | 55 | 52 | 54 | 54 | 53 |
| 55 | 54 | 52 | 55 | 54 | 55 | 55 | 55 | 55 |
| 56 | 56 | 56 | 56 | 56 | 56 | 56 | 56 | 56 |
| 57 | 57 | 58 | 57 | 57 | 57 | 57 | 57 | 58 |
| 58 | 60 | 57 | 58 | 58 | 59 | 58 | 58 | 57 |
| 59 | 58 | 59 | 59 | 61 | 58 | 59 | 59 | 59 |
| 60 | 59 | 60 | 60 | 59 | 60 | 60 | 60 | 60 |
| 61 | 61 | 61 | 61 | 63 | 63 | 61 | 61 | 61 |
| 62 | 62 | 62 | 62 | 60 | 61 | 62 | 62 | 62 |
| 63 | 63 | 63 | 63 | 62 | 62 | 63 | 63 | 63 |
| 64 | 64 | 64 | 64 | 64 | 64 | 64 | 64 | 64 |
| 65 | 65 | 66 | 65 | 67 | 68 | 65 | 65 | 65 |
| 66 | 66 | 65 | 66 | 65 | 66 | 66 | 66 | 66 |
| 67 | 70 | 68 | 67 | 66 | 65 | 67 | 67 | 67 |
| 68 | 67 | 67 | 68 | 68 | 67 | 68 | 68 | 68 |

FIG. 7B-3

| | | | | | | | | |
|---|---|---|---|---|---|---|---|---|
| 69 | 68 | 69 | 69 | 70 | 69 | 69 | 69 | 69 |
| 70 | 71 | 71 | 70 | 69 | 70 | 70 | 70 | 70 |
| 71 | 69 | 72 | 71 | 76 | 72 | 71 | 71 | 71 |
| 72 | 74 | 70 | 72 | 72 | 71 | 72 | 72 | 72 |
| 73 | 72 | 73 | 73 | 75 | 73 | 73 | 73 | 73 |
| 74 | 73 | 75 | 74 | 71 | 76 | 74 | 74 | 74 |
| 75 | 75 | 74 | 75 | 74 | 75 | 75 | 76 | 75 |
| 76 | 77 | 76 | 76 | 73 | 74 | 76 | 75 | 76 |
| 77 | 76 | 77 | 77 | 81 | 78 | 77 | 77 | 77 |
| 78 | 78 | 78 | 78 | 83 | 79 | 78 | 78 | 78 |
| 79 | 79 | 80 | 79 | 82 | 77 | 79 | 79 | 79 |
| 80 | 81 | 79 | 80 | 84 | 80 | 80 | 80 | 80 |
| 81 | 80 | 81 | 81 | 78 | 81 | 81 | 81 | 81 |
| 82 | 82 | 82 | 82 | 77 | 83 | 82 | 82 | 82 |
| 83 | 84 | 83 | 83 | 80 | 82 | 83 | 83 | 83 |
| 84 | 83 | 84 | 84 | 79 | 84 | 84 | 84 | 84 |

FIG. 7B-4

Table 3 #8

| | | |
|---|---|---|
| age | 60 | |
| Error score | 144 | 112 |
| Mean error | 3.6941176 | 3.3176471 |
| SQRT of erro | 12 | 10.583005 |
| B+Y SQRT | 9 | 7.4161985 |
| R+G SQRT | 9 | 7.6811457 |
| Quad. axis | 0 | -0.264947 |
| BINOCULARLY NORMAL | | |
| On eye to eye comparison | | |
| 1.166994756 | | |
| Box 1 SQRT | 5.477226 | 4 |
| Box 2 SQRT | 5.744563 | 6.708204 |
| Box 3 SQRT | 6.480741 | 5.291503 |
| Box 4 SQRT | 6.244998 | 4.795832 |
| Amp. sine | 0.4679429 | 0.3429092 |
| C.M.A. | 21.109112 | 72.924181 |
| | 63.605633 | 30.420702 |
| dev. +/- | 3.0457777 | 3.3650659 |
| beta | 0.1266724 | 0.1033592 |
| M.S.E. | 1.8869649 | 1.2368789 |
| S.E.(A) | 0.2107111 | 0.1705961 |

Table 3 #10

| | | |
|---|---|---|
| age | 44 | |
| Error score | 204 | 132 |
| Mean error | 4.4 | 3.5529412 |
| SQRT of erro | 14.282857 | 11.489125 |
| B+Y SQRT | 11.224972 | 7.6157731 |
| R+G SQRT | 9.486833 | 8.8881944 |
| Quad. axis | 1.7381392 | -1.272421 |
| 95% BINOC ERROR | | |
| On eye to eye comparison | | |
| 2.543731564 | | |
| Box 1 SQRT | 5.656854 | 6 |
| Box 2 SQRT | 5.291503 | 5.291503 |
| Box 3 SQRT | 7.874008 | 5.91608 |
| Box 4 SQRT | 9.055385 | 5.744563 |
| Amp. sine | 0.49235 | 0.6536313 |
| C.M.A. | 80.165154 | 21.655336 |
| | 37.661675 | 64.151857 |
| dev. +/- | 4.4283958 | 1.8785324 |
| beta | 0.1118977 | 0.1839691 |
| M.S.E. | 4.4159331 | 1.4005054 |
| S.E.(A) | 0.3223419 | 0.1815298 |

Table 3 #9

| | | |
|---|---|---|
| age | 42 | |
| Error score | 72 | 36 |
| Mean error | 2.847059 | 2.423529 |
| SQRT of erro | 8.485281 | 6 |
| B+Y SQRT | 7.348469 | 4.358899 |
| R+G SQRT | 5.656854 | 4.123106 |
| Quad. axis | 1.691615 | 0.235793 |
| BINOCULARLY NORMAL | | |
| On eye to eye comparison | | |
| 2.235281 | | |
| Box 1 SQRT | 5.196152 | 2 |
| Box 2 SQRT | 4.582576 | 4.123106 |
| Box 3 SQRT | 4.358899 | 3.872983 |
| Box 4 SQRT | 2.236068 | 0 |
| Amp. sine | 0.214055 | 0.081539 |
| C.M.A. | 5.679393 | 1.338413 |
| | 48.17591 | 43.83493 |
| dev. +/- | 4.448483 | 7.229805 |
| beta | 0.075185 | 0.033645 |
| M.S.E. | 0.84228 | 0.322823 |
| S.E.(A) | 0.140778 | 0.087154 |

FIG. 7B-5

| PATIENT 7: | | Table 1 #14 |
|---|---|---|
| DOT m/d/y | | AGE 65 |
| 1/14/98 | 1st EYE | 2nd EYE |
| EYE | RIGHT | left |
| Reference cap position | PLACEMEN cap position | PLACEMENT cap position |
| 85 | 1 | 2 |
| 1 | 4 | 85 |
| 2 | 85 | 1 |
| 3 | 3 | 3 |
| 4 | 2 | 4 |
| 5 | 5 | 5 |
| 6 | 7 | 7 |
| 7 | 8 | 6 |
| 8 | 9 | 10 |
| 9 | 6 | 8 |
| 10 | 11 | 9 |
| 11 | 10 | 11 |
| 12 | 14 | 14 |
| 13 | 13 | 12 |
| 14 | 12 | 13 |
| 15 | 15 | 15 |
| 16 | 16 | 16 |
| 17 | 17 | 17 |
| 18 | 20 | 21 |
| 19 | 21 | 20 |
| 20 | 19 | 18 |
| 21 | 18 | 19 |

| PATIENT 8: | | Table 1 #2 |
|---|---|---|
| DOT m/d/y | | AGE 27 |
| 12/4/97 | 1st EYE | 2nd EYE |
| EYE | RIGHT | left |
| Reference cap position | PLACEMEN cap position | PLACEMENT cap position |
| 85 | 85 | 1 |
| 1 | 2 | 85 |
| 2 | 1 | 3 |
| 3 | 3 | 4 |
| 4 | 5 | 2 |
| 5 | 4 | 5 |
| 6 | 6 | 7 |
| 7 | 7 | 6 |
| 8 | 9 | 8 |
| 9 | 8 | 9 |
| 10 | 10 | 10 |
| 11 | 11 | 11 |
| 12 | 12 | 12 |
| 13 | 13 | 14 |
| 14 | 14 | 13 |
| 15 | 15 | 15 |
| 16 | 16 | 17 |
| 17 | 18 | 16 |
| 18 | 17 | 18 |
| 19 | 19 | 19 |
| 20 | 21 | 21 |
| 21 | 20 | 20 |

| PATIENT 9: | | Table 1 #1 |
|---|---|---|
| DOT m/d/y | | AGE 50 |
| 10/28/97 | 1st EYE | 2nd EYE |
| EYE | RIGHT | left |
| Reference cap position | PLACEMEN cap position | PLACEMENT cap position |
| 85 | 85 | 1 |
| 1 | 2 | 2 |
| 2 | 1 | 85 |
| 3 | 6 | 4 |
| 4 | 5 | 3 |
| 5 | 4 | 6 |
| 6 | 3 | 5 |
| 7 | 7 | 7 |
| 8 | 9 | 8 |
| 9 | 10 | 9 |
| 10 | 8 | 10 |
| 11 | 11 | 11 |
| 12 | 13 | 12 |
| 13 | 14 | 15 |
| 14 | 12 | 13 |
| 15 | 15 | 14 |
| 16 | 17 | 16 |
| 17 | 16 | 17 |
| 18 | 18 | 18 |
| 19 | 19 | 19 |
| 20 | 21 | 21 |
| 21 | 20 | 20 |

FIG. 7C-1

| | | | | | | | | |
|---|---|---|---|---|---|---|---|---|
| 22 | 25 | 23 | 22 | 22 | 22 | 22 | 22 | 22 |
| 23 | 23 | 22 | 23 | 23 | 23 | 23 | 23 | 23 |
| 24 | 22 | 24 | 24 | 24 | 25 | 24 | 24 | 24 |
| 25 | 26 | 25 | 25 | 26 | 27 | 25 | 26 | 25 |
| 26 | 24 | 26 | 26 | 25 | 29 | 26 | 25 | 27 |
| 27 | 27 | 27 | 27 | 27 | 30 | 27 | 27 | 26 |
| 28 | 28 | 30 | 28 | 28 | 32 | 28 | 28 | 28 |
| 29 | 31 | 28 | 29 | 30 | 31 | 29 | 29 | 29 |
| 30 | 29 | 29 | 30 | 29 | 24 | 30 | 31 | 31 |
| 31 | 30 | 32 | 31 | 31 | 26 | 31 | 32 | 30 |
| 32 | 34 | 31 | 32 | 32 | 28 | 32 | 30 | 32 |
| 33 | 33 | 33 | 33 | 33 | 34 | 33 | 33 | 33 |
| 34 | 32 | 34 | 34 | 35 | 33 | 34 | 34 | 34 |
| 35 | 35 | 35 | 35 | 34 | 35 | 35 | 35 | 35 |
| 36 | 38 | 36 | 36 | 36 | 36 | 36 | 40 | 36 |
| 37 | 37 | 40 | 37 | 37 | 37 | 37 | 42 | 37 |
| 38 | 39 | 38 | 38 | 42 | 39 | 38 | 38 | 38 |
| 39 | 36 | 37 | 39 | 40 | 38 | 39 | 41 | 39 |
| 40 | 41 | 42 | 40 | 39 | 41 | 40 | 37 | 40 |
| 41 | 40 | 41 | 41 | 38 | 42 | 41 | 39 | 41 |
| 42 | 42 | 39 | 42 | 41 | 40 | 42 | 36 | 42 |
| 43 | 48 | 46 | 43 | 45 | 43 | 43 | 50 | 43 |
| 44 | 49 | 48 | 44 | 43 | 46 | 44 | 46 | 46 |
| 45 | 46 | 43 | 45 | 46 | 44 | 45 | 45 | 47 |

FIG. 7C-2

| | | | | | | | | |
|---|---|---|---|---|---|---|---|---|
| 46 | 45 | 45 | 46 | 44 | 45 | 46 | 44 | 45 |
| 47 | 44 | 44 | 47 | 47 | 48 | 47 | 48 | 44 |
| 48 | 47 | 47 | 48 | 48 | 47 | 48 | 47 | 50 |
| 49 | 43 | 51 | 49 | 50 | 49 | 49 | 43 | 48 |
| 50 | 53 | 49 | 50 | 51 | 50 | 50 | 49 | 49 |
| 51 | 50 | 50 | 51 | 49 | 51 | 51 | 52 | 53 |
| 52 | 51 | 54 | 52 | 53 | 52 | 52 | 51 | 51 |
| 53 | 52 | 53 | 53 | 52 | 54 | 53 | 53 | 52 |
| 54 | 54 | 52 | 54 | 54 | 53 | 54 | 54 | 54 |
| 55 | 57 | 55 | 55 | 55 | 55 | 55 | 56 | 55 |
| 56 | 56 | 56 | 56 | 56 | 56 | 56 | 55 | 56 |
| 57 | 55 | 57 | 57 | 59 | 57 | 57 | 59 | 58 |
| 58 | 58 | 58 | 58 | 57 | 58 | 58 | 58 | 57 |
| 59 | 59 | 59 | 59 | 58 | 59 | 59 | 57 | 59 |
| 60 | 60 | 60 | 60 | 60 | 60 | 60 | 61 | 60 |
| 61 | 62 | 62 | 61 | 62 | 62 | 61 | 62 | 62 |
| 62 | 63 | 61 | 62 | 61 | 61 | 62 | 60 | 63 |
| 63 | 61 | 63 | 63 | 63 | 63 | 63 | 63 | 61 |
| 64 | 66 | 66 | 64 | 64 | 64 | 64 | 64 | 66 |
| 65 | 64 | 64 | 65 | 66 | 65 | 65 | 65 | 64 |
| 66 | 65 | 65 | 66 | 65 | 66 | 66 | 67 | 65 |
| 67 | 69 | 67 | 67 | 67 | 67 | 67 | 66 | 67 |
| 68 | 68 | 69 | 68 | 68 | 68 | 68 | 68 | 69 |
| 69 | 71 | 70 | 69 | 69 | 69 | 69 | 69 | 68 |

FIG. 7C-3

| | | | | | | | | |
|---|---|---|---|---|---|---|---|---|
| 70 | 70 | 68 | 70 | 70 | 70 | 70 | 71 | 70 |
| 71 | 72 | 71 | 71 | 71 | 71 | 71 | 70 | 71 |
| 72 | 67 | 72 | 72 | 72 | 72 | 72 | 72 | 72 |
| 73 | 78 | 73 | 73 | 73 | 73 | 73 | 74 | 73 |
| 74 | 76 | 78 | 74 | 74 | 74 | 74 | 73 | 75 |
| 75 | 73 | 79 | 75 | 76 | 76 | 75 | 75 | 74 |
| 76 | 75 | 76 | 76 | 75 | 75 | 76 | 78 | 79 |
| 77 | 77 | 75 | 77 | 77 | 77 | 77 | 77 | 77 |
| 78 | 74 | 77 | 78 | 80 | 78 | 78 | 76 | 76 |
| 79 | 79 | 74 | 79 | 78 | 79 | 79 | 79 | 78 |
| 80 | 81 | 80 | 80 | 79 | 80 | 80 | 81 | 81 |
| 81 | 80 | 84 | 81 | 81 | 82 | 81 | 84 | 82 |
| 82 | 84 | 81 | 82 | 82 | 81 | 82 | 82 | 80 |
| 83 | 82 | 83 | 83 | 84 | 83 | 83 | 83 | 84 |
| 84 | 83 | 82 | 84 | 83 | 84 | 84 | 80 | 83 |

FIG. 7C-4

Table 1 #14

| | | |
|---|---|---|
| age | 65 | |
| Error score | 256 | 184 |
| Mean error | 5.0117647 | 4.1647059 |
| SQRT of erro | 16 | 13.56466 |
| B+Y SQRT | 12.727922 | 10.954451 |
| R+G SQRT | 10.440307 | 8.1853528 |
| Quad. axis | 2.2876156 | 2.7690984 |
| BINOCULARLY NORMAL | | |
| On eye to eye comparison | | |
| 2.18534 | | |
| Box 1 SQRT | 7.28011 | 6.244998 |
| Box 2 SQRT | 8.3666 | 6.708204 |
| Box 3 SQRT | 6.928203 | 6.480741 |
| Box 4 SQRT | 9.219544 | 7.615773 |
| Amp. sine | 0.6970685 | 0.9644788 |
| C.M.A. | 78.943251 | 83.060257 |
| | 36.439772 | 40.556778 |
| dev. +/- | 3.8840018 | 1.8411127 |
| beta | 0.1390864 | 0.2315839 |
| M.S.E. | 6.8091284 | 2.9290569 |
| S.E.(A) | 0.4002684 | 0.2625243 |

Table 1 #2

| | | |
|---|---|---|
| age | 27 | |
| Error score | 108 | 104 |
| Mean error | 3.270588 | 3.223529 |
| SQRT of erro | 10.3923 | 10.19804 |
| B+Y SQRT | 8.888194 | 7.483315 |
| R+G SQRT | 5.91608 | 6.928203 |
| Quad. axis | 2.972115 | 0.555112 |
| BINOCULARLY NORMAL | | |
| On eye to eye comparison | | |
| 0.055734 | | |
| Box 1 SQRT | 4.242641 | 5 |
| Box 2 SQRT | 5.656854 | 7.071068 |
| Box 3 SQRT | 6.082763 | 4.242641 |
| Box 4 SQRT | 4.582576 | 3.316625 |
| Amp. sine | 0.652568 | 0.405924 |
| C.M.A. | 1.115459781 | 79.24345957 |
| | 43.61198078 | 36.73998057 |
| dev. +/- | 1.634796293 | 3.431059797 |
| beta | 0.199526 | 0.125925 |
| M.S.E. | 1.057208 | 1.801885 |
| S.E.(A) | 0.15772 | 0.205906 |

Table 1 #1

| | | |
|---|---|---|
| age | 50 | |
| Error score | 204 | 116 |
| Mean error | 4.4 | 3.3647059 |
| SQRT of erro | 14.282857 | 10.77033 |
| B+Y SQRT | 12.409674 | 8.1240384 |
| R+G SQRT | 7.5498344 | 6.9282032 |
| Quad. axis | 4.8598392 | 1.1958352 |
| 95% BINOC ERROR | | |
| On eye to eye comparison | | |
| 3.262527243 | | |
| Box 1 SQRT | 6.164414 | 4.898979 |
| Box 2 SQRT | 8.062258 | 3.162278 |
| Box 3 SQRT | 7.681146 | 6.244998 |
| Box 4 SQRT | 6.480741 | 6.557439 |
| Amp. sine | 1.5141409 | 0.3551135 |
| C.M.A. | 0.7908426 | 3.3399295 |
| | 43.287364 | 45.83645 |
| dev. +/- | 1.6802033 | 4.0600547 |
| beta | 0.3441229 | 0.1055407 |
| M.S.E. | 6.0122631 | 1.930989 |
| S.E.(A) | 0.3761183 | 0.213155 |

FIG. 7C-5

PATIENT 10: Table 1 #7

| DOT m/d/y | | AGE | 36 |
|---|---|---|---|
| 11/20/97 | 1st EYE | 2nd EYE | |
| EYE | RIGHT | left | |
| Reference cap position | PLACEMEN cap position | PLACEMENT cap position | |
| 85 | 85 | 85 | |
| 1 | 1 | 1 | |
| 2 | 2 | 2 | |
| 3 | 3 | 3 | |
| 4 | 4 | 4 | |
| 5 | 6 | 5 | |
| 6 | 5 | 6 | |
| 7 | 7 | 7 | |
| 8 | 8 | 8 | |
| 9 | 10 | 10 | |
| 10 | 9 | 8 | |
| 11 | 11 | 11 | |
| 12 | 12 | 12 | |
| 13 | 13 | 14 | |
| 14 | 14 | 13 | |
| 15 | 15 | 15 | |
| 16 | 16 | 16 | |
| 17 | 17 | 17 | |
| 18 | 18 | 18 | |
| 19 | 19 | 19 | |
| 20 | 20 | 21 | |
| 21 | 21 | 20 | |

FIG. 7D-1

| | | |
|---|---|---|
| 22 | 22 | 23 |
| 23 | 23 | 22 |
| 24 | 24 | 24 |
| 25 | 26 | 25 |
| 26 | 27 | 26 |
| 27 | 25 | 27 |
| 28 | 28 | 28 |
| 29 | 29 | 29 |
| 30 | 30 | 31 |
| 31 | 35 | 30 |
| 32 | 31 | 32 |
| 33 | 32 | 33 |
| 34 | 33 | 34 |
| 35 | 34 | 35 |
| 36 | 36 | 36 |
| 37 | 37 | 37 |
| 38 | 38 | 38 |
| 39 | 39 | 39 |
| 40 | 40 | 40 |
| 41 | 41 | 41 |
| 42 | 42 | 42 |
| 43 | 45 | 43 |
| 44 | 43 | 45 |
| 45 | 44 | 47 |

FIG. 7D-2

| | | |
|---|---|---|
| 46 | 46 | 44 |
| 47 | 47 | 48 |
| 48 | 48 | 46 |
| 49 | 49 | 49 |
| 50 | 50 | 51 |
| 51 | 51 | 50 |
| 52 | 52 | 54 |
| 53 | 53 | 52 |
| 54 | 54 | 53 |
| 55 | 55 | 55 |
| 56 | 56 | 56 |
| 57 | 58 | 57 |
| 58 | 57 | 58 |
| 59 | 59 | 59 |
| 60 | 60 | 60 |
| 61 | 62 | 62 |
| 62 | 61 | 61 |
| 63 | 63 | 63 |
| 64 | 64 | 64 |
| 65 | 66 | 65 |
| 66 | 65 | 66 |
| 67 | 67 | 67 |
| 68 | 69 | 68 |

FIG. 7D-3

| | | |
|---|---|---|
| 69 | 68 | 69 |
| 70 | 70 | 70 |
| 71 | 71 | 71 |
| 72 | 72 | 72 |
| 73 | 73 | 73 |
| 74 | 75 | 75 |
| 75 | 74 | 74 |
| 76 | 76 | 76 |
| 77 | 77 | 77 |
| 78 | 78 | 79 |
| 79 | 79 | 78 |
| 80 | 80 | 80 |
| 81 | 82 | 81 |
| 82 | 81 | 82 |
| 83 | 83 | 84 |
| 84 | 84 | 83 |

FIG. 7D-4

Table 1 #7

| | | |
|---|---|---|
| age | 36 | |
| Error score | 64 | 72 |
| Mean error | 2.7529412 | 2.8470588 |
| SQRT of erro | 8 | 8.4852814 |
| B+Y SQRT | 5.4772256 | 7.0710678 |
| R+G SQRT | 5.8309519 | 4.7958315 |
| Quad. axis | -0.353726 | 2.2752363 |
| BINOCULARLY NORMAL | | |
| On eye to eye comparison | | |
| 0.735281374 | | |
| Box 1 SQRT | 2.828427 | 4.123106 |
| Box 2 SQRT | 5.196152 | 2.828427 |
| Box 3 SQRT | 3.741657 | 5.91608 |
| Box 4 SQRT | 3.872983 | 3.464102 |
| Amp. sine | 0.3895382 | 0.5822303 |
| C.M.A. | 73.606231 | 7.0870776 |
| | 31.102752 | 49.583599 |
| dev. +/- | 2.7492362 | 1.7681913 |
| beta | 0.1414989 | 0.2045024 |
| M.S.E. | 1.0653835 | 0.9845321 |
| S.E.(A) | 0.1583283 | 0.152202 |

FIG. 7D-5

PATIENT 11: Table 1 #12

| DOT m/d/y | | AGE | 40 |
|---|---|---|---|
| 2/20/98 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 2 | 1 | |
| 2 | 1 | 2 | |
| 3 | 3 | 3 | |
| 4 | 4 | 5 | |
| 5 | 5 | 4 | |
| 6 | 6 | 6 | |
| 7 | 7 | 7 | |
| 8 | 9 | 9 | |
| 9 | 8 | 8 | |
| 10 | 10 | 10 | |
| 11 | 11 | 11 | |
| 12 | 12 | 12 | |
| 13 | 14 | 14 | |
| 14 | 13 | 13 | |
| 15 | 15 | 15 | |
| 16 | 16 | 16 | |
| 17 | 17 | 17 | |
| 18 | 18 | 18 | |
| 19 | 19 | 19 | |
| 20 | 20 | 20 | |
| 21 | 21 | 21 | |
| 22 | 22 | 23 | |

PATIENT 12: Table 3 #7

| DOT m/d/y | | AGE | 47 |
|---|---|---|---|
| 2/3/98 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 2 | 1 | |
| 2 | 1 | 2 | |
| 3 | 3 | 3 | |
| 4 | 4 | 4 | |
| 5 | 6 | 5 | |
| 6 | 5 | 6 | |
| 7 | 7 | 7 | |
| 8 | 8 | 8 | |
| 9 | 9 | 9 | |
| 10 | 10 | 10 | |
| 11 | 11 | 12 | |
| 12 | 12 | 11 | |
| 13 | 13 | 14 | |
| 14 | 14 | 13 | |
| 15 | 15 | 15 | |
| 16 | 16 | 17 | |
| 17 | 17 | 18 | |
| 18 | 18 | 16 | |
| 19 | 19 | 19 | |
| 20 | 21 | 20 | |
| 21 | 20 | 21 | |
| 22 | 22 | 22 | |

PATIENT 13: Table 3 #5

| DOT m/d/y | | AGE | 57 |
|---|---|---|---|
| 12/10/97 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 1 | 2 | |
| 2 | 2 | 1 | |
| 3 | 3 | 3 | |
| 4 | 4 | 4 | |
| 5 | 5 | 6 | |
| 6 | 6 | 5 | |
| 7 | 7 | 7 | |
| 8 | 8 | 8 | |
| 9 | 9 | 9 | |
| 10 | 10 | 10 | |
| 11 | 11 | 11 | |
| 12 | 12 | 12 | |
| 13 | 13 | 13 | |
| 14 | 14 | 14 | |
| 15 | 15 | 15 | |
| 16 | 16 | 16 | |
| 17 | 17 | 17 | |
| 18 | 18 | 18 | |
| 19 | 19 | 19 | |
| 20 | 20 | 20 | |
| 21 | 21 | 21 | |
| 22 | 22 | 22 | |

FIG. 7E-1

| | | | | | | | | |
|---|---|---|---|---|---|---|---|---|
| 23 | 24 | 22 | 23 | 23 | 24 | 23 | 23 | 23 |
| 24 | 23 | 24 | 24 | 24 | 23 | 24 | 24 | 24 |
| 25 | 25 | 25 | 25 | 25 | 25 | 25 | 25 | 25 |
| 26 | 26 | 26 | 26 | 26 | 26 | 26 | 26 | 26 |
| 27 | 28 | 27 | 27 | 28 | 27 | 27 | 27 | 27 |
| 28 | 27 | 29 | 28 | 27 | 29 | 28 | 29 | 30 |
| 29 | 29 | 31 | 29 | 29 | 28 | 29 | 28 | 28 |
| 30 | 30 | 28 | 30 | 30 | 31 | 30 | 30 | 29 |
| 31 | 31 | 30 | 31 | 31 | 30 | 31 | 31 | 31 |
| 32 | 32 | 32 | 32 | 32 | 32 | 32 | 32 | 32 |
| 33 | 33 | 34 | 33 | 34 | 33 | 33 | 34 | 33 |
| 34 | 34 | 33 | 34 | 33 | 35 | 34 | 33 | 34 |
| 35 | 35 | 35 | 35 | 35 | 34 | 35 | 35 | 35 |
| 36 | 36 | 36 | 36 | 36 | 37 | 36 | 36 | 36 |
| 37 | 37 | 38 | 37 | 37 | 38 | 37 | 37 | 38 |
| 38 | 40 | 37 | 38 | 38 | 36 | 38 | 38 | 37 |
| 39 | 38 | 39 | 39 | 40 | 39 | 39 | 39 | 42 |
| 40 | 39 | 40 | 40 | 39 | 40 | 40 | 41 | 39 |
| 41 | 41 | 41 | 41 | 42 | 41 | 41 | 42 | 40 |
| 42 | 42 | 42 | 42 | 41 | 42 | 42 | 40 | 41 |
| 43 | 46 | 43 | 43 | 43 | 43 | 43 | 43 | 43 |
| 44 | 43 | 45 | 44 | 45 | 44 | 44 | 45 | 44 |
| 45 | 45 | 44 | 45 | 46 | 45 | 45 | 46 | 45 |
| 46 | 48 | 47 | 46 | 44 | 46 | 46 | 47 | 46 |
| 47 | 44 | 46 | 47 | 47 | 48 | 47 | 44 | 47 |
| 48 | 47 | 48 | 48 | 48 | 47 | 48 | 48 | 48 |
| 49 | 50 | 49 | 49 | 49 | 49 | 49 | 49 | 49 |
| 50 | 49 | 50 | 50 | 51 | 51 | 50 | 50 | 51 |
| 51 | 52 | 51 | 51 | 50 | 52 | 51 | 51 | 50 |
| 52 | 53 | 52 | 52 | 53 | 50 | 52 | 54 | 52 |
| 53 | 51 | 54 | 53 | 52 | 54 | 53 | 53 | 53 |
| 54 | 54 | 53 | 54 | 54 | 53 | 54 | 52 | 54 |
| 55 | 56 | 55 | 55 | 55 | 55 | 55 | 55 | 55 |

FIG. 7E-2

| | | | | | | | | |
|---|---|---|---|---|---|---|---|---|
| 56 | 55 | 56 | 56 | 56 | 56 | 56 | 56 | 56 |
| 57 | 58 | 57 | 57 | 57 | 57 | 57 | 57 | 57 |
| 58 | 57 | 58 | 58 | 58 | 58 | 58 | 58 | 58 |
| 59 | 59 | 59 | 59 | 59 | 59 | 59 | 59 | 59 |
| 60 | 60 | 60 | 60 | 60 | 60 | 60 | 60 | 61 |
| 61 | 61 | 61 | 61 | 62 | 61 | 61 | 61 | 62 |
| 62 | 63 | 62 | 62 | 61 | 62 | 62 | 62 | 60 |
| 63 | 62 | 63 | 63 | 63 | 63 | 63 | 63 | 63 |
| 64 | 64 | 64 | 64 | 64 | 64 | 64 | 65 | 64 |
| 65 | 66 | 65 | 65 | 66 | 65 | 65 | 64 | 65 |
| 66 | 67 | 66 | 66 | 65 | 67 | 66 | 66 | 66 |
| 67 | 68 | 68 | 67 | 67 | 66 | 67 | 67 | 67 |
| 68 | 65 | 69 | 68 | 68 | 69 | 68 | 69 | 69 |
| 69 | 69 | 67 | 69 | 69 | 68 | 69 | 68 | 68 |
| 70 | 70 | 70 | 70 | 70 | 71 | 70 | 70 | 70 |
| 71 | 71 | 71 | 71 | 71 | 72 | 71 | 71 | 71 |
| 72 | 73 | 72 | 72 | 72 | 70 | 72 | 72 | 72 |
| 73 | 72 | 73 | 73 | 73 | 73 | 73 | 73 | 73 |
| 74 | 75 | 74 | 74 | 75 | 74 | 74 | 75 | 75 |
| 75 | 74 | 75 | 75 | 74 | 75 | 75 | 74 | 74 |
| 76 | 77 | 76 | 76 | 76 | 79 | 76 | 76 | 76 |
| 77 | 76 | 77 | 77 | 77 | 78 | 77 | 77 | 77 |
| 78 | 78 | 79 | 78 | 78 | 77 | 78 | 79 | 78 |
| 79 | 79 | 78 | 79 | 79 | 76 | 79 | 78 | 79 |
| 80 | 80 | 81 | 80 | 80 | 80 | 80 | 80 | 80 |
| 81 | 82 | 82 | 81 | 82 | 81 | 81 | 82 | 82 |
| 82 | 81 | 80 | 82 | 81 | 82 | 82 | 81 | 81 |
| 83 | 84 | 84 | 83 | 83 | 83 | 83 | 84 | 83 |
| 84 | 83 | 83 | 84 | 84 | 84 | 84 | 83 | 84 |

FIG. 7E-3

Table 1 #12

| | | |
|---|---|---|
| age | 40 | |
| Error score | 112 | 72 |
| Mean error | 3.317647 | 2.847059 |
| SQRT of erro | 10.58301 | 8.485281 |
| B+Y SQRT | 8.485281 | 6.557439 |
| R+G SQRT | 6.480741 | 5.477226 |
| Quad. axis | 2.004541 | 1.080213 |
| BINOCULARLY NORMAL | | |
| On eye to eye comparison | | |
| 1.84772387 | | |
| Box 1 SQRT | 3.464102 | 3.741657 |
| Box 2 SQRT | 4.582576 | 4.795832 |
| Box 3 SQRT | 6.855655 | 3.316625 |
| Box 4 SQRT | 5.656854 | 4.898979 |
| Amp. sine | 0.554868 | 0.430219 |
| C.M.A. | 3.179307 | 79.01966 |
| | 45.67583 | 36.51618 |
| dev. +/- | 2.217786 | 1.977803 |
| beta | 0.167247 | 0.15111 |
| M.S.E. | 1.406694 | 0.672555 |
| S.E.(A) | 0.18193 | 0.125797 |

Table 3 #7

| | | |
|---|---|---|
| age | 47 | |
| Error score | 60 | 84 |
| Mean error | 2.705882 | 2.988235 |
| SQRT of erro | 7.745967 | 9.165151 |
| B+Y SQRT | 6.480741 | 6.480741 |
| R+G SQRT | 4.582576 | 6.708204 |
| Quad. axis | 1.898165 | -0.22746 |
| BINOCULARLY NORMAL | | |
| On eye to eye comparison | | |
| 1.669184697 | | |
| Box 1 SQRT | 3.316625 | 4.123106 |
| Box 2 SQRT | 4.123106 | 4.795832 |
| Box 3 SQRT | 4.472136 | 4 |
| Box 4 SQRT | 3.464102 | 5.291503 |
| Amp. sine | 0.323284 | 0.361454 |
| C.M.A. | 84.8409 | 70.61622 |
| | 42.33742 | 28.11274 |
| dev. +/- | 1.980016 | 2.929942 |
| beta | 0.119474 | 0.120959 |
| M.S.E. | 0.380616 | 1.041852 |
| S.E.(A) | 0.094634 | 0.15657 |

Table 3 #5

| | | |
|---|---|---|
| age | 57 | |
| Error score | 60 | 56 |
| Mean error | 2.705882 | 2.658824 |
| SQRT of erro | 7.745967 | 7.483315 |
| B+Y SQRT | 6.324555 | 5.656854 |
| R+G SQRT | 4.358899 | 4.795832 |
| Quad. axis | 1.965656 | 0.861023 |
| BINOCULARLY NORMAL | | |
| On eye to eye comparison | | |
| 0.012651919 | | |
| Box 1 SQRT | 0 | 2.645751 |
| Box 2 SQRT | 4.123106 | 4.898979 |
| Box 3 SQRT | 4.582576 | 3.464102 |
| Box 4 SQRT | 4.690416 | 3.605551 |
| Amp. sine | 0.516735 | 0.382254 |
| C.M.A. | 82.05842 | 79.96252 |
| | 39.55494 | 37.45904 |
| dev. +/- | 1.721929 | 2.559252 |
| beta | 0.190967 | 0.143768 |
| M.S.E. | 0.735442 | 0.889023 |
| S.E.(A) | 0.131547 | 0.144631 |

FIG. 7E-4

| | | | | | | | | | | | |
|---|---|---|---|---|---|---|---|---|---|---|---|
| PATIENT 14: | | Table 1 #3 | | PATIENT 15: | | Table 1 #4 | | PATIENT 16: | | Table 1 #5 | |
| DOT m/d/y | | AGE | 54 | DOT m/d/y | | AGE | 55 | DOT m/d/y | | AGE | 62 |
| 10/30/97 | 1st EYE | 2nd EYE | | 10/7/97 | 1st EYE | 2nd EYE | | 11/18/97 | 1st EYE | 2nd EYE | |
| EYE | RIGHT | left | | EYE | RIGHT | left | | EYE | RIGHT | left | |
| Reference | PLACEMEN | PLACEMENT | | Reference | PLACEMEN | PLACEMENT | | Reference | PLACEMEN | PLACEMENT | |
| cap position | cap position | cap position | | cap position | cap position | cap position | | cap position | cap position | cap position | |
| 85 | 85 | 85 | | 85 | 85 | 85 | | 85 | 85 | 2 | |
| 1 | 3 | 2 | | 1 | 1 | 1 | | 1 | 2 | 85 | |
| 2 | 5 | 1 | | 2 | 2 | 2 | | 2 | 1 | 1 | |
| 3 | 4 | 4 | | 3 | 3 | 3 | | 3 | 3 | 3 | |
| 4 | 2 | 3 | | 4 | 4 | 4 | | 4 | 4 | 4 | |
| 5 | 1 | 10 | | 5 | 5 | 5 | | 5 | 6 | 5 | |
| 6 | 8 | 9 | | 6 | 6 | 6 | | 6 | 8 | 7 | |
| 7 | 6 | 7 | | 7 | 7 | 8 | | 7 | 5 | 6 | |
| 8 | 7 | 8 | | 8 | 8 | 7 | | 8 | 7 | 8 | |
| 9 | 10 | 6 | | 9 | 10 | 9 | | 9 | 9 | 10 | |
| 10 | 9 | 5 | | 10 | 9 | 10 | | 10 | 10 | 9 | |
| 11 | 13 | 13 | | 11 | 11 | 11 | | 11 | 11 | 12 | |
| 12 | 11 | 12 | | 12 | 12 | 12 | | 12 | 12 | 11 | |
| 13 | 12 | 11 | | 13 | 14 | 14 | | 13 | 13 | 14 | |
| 14 | 14 | 14 | | 14 | 13 | 13 | | 14 | 14 | 13 | |
| 15 | 16 | 15 | | 15 | 15 | 15 | | 15 | 15 | 15 | |
| 16 | 15 | 16 | | 16 | 16 | 16 | | 16 | 16 | 16 | |
| 17 | 17 | 17 | | 17 | 17 | 17 | | 17 | 17 | 17 | |
| 18 | 18 | 18 | | 18 | 18 | 18 | | 18 | 18 | 18 | |
| 19 | 19 | 20 | | 19 | 19 | 19 | | 19 | 19 | 19 | |
| 20 | 21 | 19 | | 20 | 20 | 20 | | 20 | 20 | 20 | |
| 21 | 20 | 21 | | 21 | 21 | 21 | | 21 | 21 | 21 | |
| 22 | 24 | 22 | | 22 | 22 | 22 | | 22 | 22 | 22 | |

FIG. 7F-1

| | | | | | | | | |
|---|---|---|---|---|---|---|---|---|
| 23 | 27 | 23 | 23 | 23 | 23 | 23 | 23 | 23 |
| 24 | 26 | 24 | 24 | 24 | 24 | 24 | 24 | 24 |
| 25 | 28 | 25 | 25 | 25 | 25 | 25 | 25 | 25 |
| 26 | 25 | 26 | 26 | 26 | 26 | 26 | 26 | 26 |
| 27 | 23 | 27 | 27 | 27 | 27 | 27 | 27 | 27 |
| 28 | 22 | 29 | 28 | 29 | 29 | 28 | 28 | 28 |
| 29 | 29 | 28 | 29 | 28 | 28 | 29 | 30 | 29 |
| 30 | 30 | 30 | 30 | 30 | 30 | 30 | 29 | 31 |
| 31 | 31 | 31 | 31 | 31 | 31 | 31 | 31 | 30 |
| 32 | 33 | 34 | 32 | 32 | 32 | 32 | 32 | 32 |
| 33 | 32 | 33 | 33 | 33 | 33 | 33 | 34 | 33 |
| 34 | 34 | 32 | 34 | 34 | 34 | 34 | 33 | 34 |
| 35 | 36 | 35 | 35 | 35 | 35 | 35 | 35 | 35 |
| 36 | 35 | 39 | 36 | 37 | 37 | 36 | 36 | 36 |
| 37 | 40 | 37 | 37 | 36 | 36 | 37 | 38 | 38 |
| 38 | 39 | 38 | 38 | 39 | 38 | 38 | 37 | 37 |
| 39 | 38 | 36 | 39 | 38 | 39 | 39 | 39 | 39 |
| 40 | 42 | 40 | 40 | 40 | 40 | 40 | 40 | 40 |
| 41 | 37 | 41 | 41 | 41 | 41 | 41 | 41 | 42 |
| 42 | 41 | 42 | 42 | 42 | 42 | 42 | 42 | 41 |
| 43 | 44 | 43 | 43 | 43 | 43 | 43 | 43 | 43 |
| 44 | 43 | 44 | 44 | 46 | 44 | 44 | 44 | 44 |
| 45 | 45 | 45 | 45 | 45 | 46 | 45 | 45 | 46 |
| 46 | 46 | 46 | 46 | 44 | 45 | 46 | 46 | 45 |
| 47 | 48 | 47 | 47 | 47 | 47 | 47 | 47 | 47 |
| 48 | 52 | 50 | 48 | 48 | 48 | 48 | 49 | 48 |
| 49 | 47 | 48 | 49 | 49 | 49 | 49 | 48 | 49 |
| 50 | 49 | 49 | 50 | 50 | 50 | 50 | 50 | 50 |
| 51 | 50 | 52 | 51 | 51 | 52 | 51 | 51 | 51 |
| 52 | 51 | 51 | 52 | 52 | 51 | 52 | 53 | 53 |
| 53 | 53 | 54 | 53 | 53 | 53 | 53 | 52 | 52 |
| 54 | 54 | 53 | 54 | 54 | 55 | 54 | 54 | 54 |
| 55 | 55 | 56 | 55 | 55 | 54 | 55 | 55 | 55 |

FIG. 7F-2

| | | | | | | | | |
|---|---|---|---|---|---|---|---|---|
| 56 | 56 | 55 | 56 | 57 | 56 | 56 | 56 | 56 |
| 57 | 59 | 57 | 57 | 56 | 57 | 57 | 58 | 57 |
| 58 | 57 | 58 | 58 | 58 | 58 | 58 | 57 | 58 |
| 59 | 58 | 59 | 59 | 59 | 59 | 59 | 59 | 59 |
| 60 | 60 | 60 | 60 | 60 | 60 | 60 | 60 | 60 |
| 61 | 62 | 62 | 61 | 61 | 62 | 61 | 62 | 62 |
| 62 | 61 | 61 | 62 | 62 | 61 | 62 | 61 | 61 |
| 63 | 63 | 63 | 63 | 63 | 63 | 63 | 63 | 63 |
| 64 | 64 | 65 | 64 | 64 | 64 | 64 | 64 | 64 |
| 65 | 65 | 64 | 65 | 66 | 65 | 65 | 66 | 66 |
| 66 | 66 | 66 | 66 | 67 | 66 | 66 | 65 | 65 |
| 67 | 68 | 67 | 67 | 65 | 67 | 67 | 67 | 67 |
| 68 | 67 | 69 | 68 | 68 | 68 | 68 | 68 | 68 |
| 69 | 70 | 70 | 69 | 69 | 69 | 69 | 70 | 69 |
| 70 | 69 | 68 | 70 | 71 | 70 | 70 | 69 | 71 |
| 71 | 71 | 71 | 71 | 70 | 71 | 71 | 71 | 70 |
| 72 | 72 | 72 | 72 | 72 | 72 | 72 | 72 | 72 |
| 73 | 73 | 73 | 73 | 73 | 74 | 73 | 73 | 73 |
| 74 | 74 | 74 | 74 | 74 | 73 | 74 | 74 | 74 |
| 75 | 75 | 76 | 75 | 76 | 75 | 75 | 75 | 75 |
| 76 | 77 | 75 | 76 | 75 | 77 | 76 | 76 | 76 |
| 77 | 76 | 77 | 77 | 78 | 78 | 77 | 77 | 78 |
| 78 | 79 | 79 | 78 | 77 | 76 | 78 | 78 | 77 |
| 79 | 84 | 80 | 79 | 79 | 79 | 79 | 79 | 80 |
| 80 | 80 | 78 | 80 | 80 | 80 | 80 | 80 | 79 |
| 81 | 78 | 81 | 81 | 82 | 81 | 81 | 81 | 81 |
| 82 | 83 | 82 | 82 | 81 | 82 | 82 | 82 | 84 |
| 83 | 82 | 84 | 83 | 83 | 83 | 83 | 84 | 83 |
| 84 | 81 | 83 | 84 | 84 | 84 | 84 | 83 | 82 |

FIG. 7F-3

Table 1 #3

| | | |
|---|---|---|
| age | 54 | |
| Error score | 184 | 124 |
| Mean error | 4.164706 | 3.458824 |
| SQRT of erro | 13.56466 | 11.13553 |
| B+Y SQRT | 11.74734 | 9.380832 |
| R+G SQRT | 8.062258 | 6.557439 |
| Quad. axis | 3.685082 | 2.823393 |
| BINOCULARLY NORMAL | | |
| On eye to eye comparison | | |
| 2.179131241 | | |
| Box 1 SQRT | 7 | 6.557439 |
| Box 2 SQRT | 7.615773 | 5.291503 |
| Box 3 SQRT | 5.91608 | 5.09902 |
| Box 4 SQRT | 6.480741 | 5.196152 |
| Amp. sine | 0.846294 | 0.57568 |
| C.M.A. | 83.86575 | 3.042024 |
| | 41.36227 | 45.53855 |
| dev. +/- | 2.373259 | 2.663097 |
| beta | 0.203206 | 0.166438 |
| M.S.E. | 3.747267 | 2.18332 |
| S.E.(A) | 0.296936 | 0.226654 |

Table 1 #4

| | | |
|---|---|---|
| age | 55 | |
| Error score | 56 | 44 |
| Mean error | 2.658824 | 2.517647 |
| SQRT of erro | 7.483315 | 6.63325 |
| B+Y SQRT | 5.744563 | 5.291503 |
| R+G SQRT | 5.09902 | 4.242641 |
| Quad. axis | 0.645543 | 1.048862 |
| BINOCULARLY NORMAL | | |
| On eye to eye comparison | | |
| 0.600065193 | | |
| Box 1 SQRT | 2.828427 | 2.828427 |
| Box 2 SQRT | 3.741657 | 2.828427 |
| Box 3 SQRT | 3.316625 | 4 |
| Box 4 SQRT | 4.795832 | 3.464102 |
| Amp. sine | 0.261283 | 0.074656 |
| C.M.A. | 77.2275 | 0.265899 |
| | 34.72402 | 42.76242 |
| dev. +/- | 2.780579 | 8.814882 |
| beta | 0.09827 | 0.029653 |
| M.S.E. | 0.490314 | 0.40229 |
| S.E.(A) | 0.10741 | 0.097292 |

Table 1 #5

| | | |
|---|---|---|
| age | 62 | |
| Error score | 56 | 72 |
| Mean error | 2.658824 | 2.847059 |
| SQRT of erro | 7.483315 | 8.485281 |
| B+Y SQRT | 5.656854 | 7.348469 |
| R+G SQRT | 4.690416 | 4.472136 |
| Quad. axis | 0.966438 | 2.876333 |
| BINOCULARLY NORMAL | | |
| On eye to eye comparison | | |
| 1.251966601 | | |
| Box 1 SQRT | 3.605551 | 4.795832 |
| Box 2 SQRT | 3.464102 | 3.464102 |
| Box 3 SQRT | 4.123106 | 3.605551 |
| Box 4 SQRT | 3.741657 | 4.898979 |
| Amp. sine | 0.216589 | 0.484693 |
| C.M.A. | 4.504398 | 0.849105 |
| | 47.00092 | 43.34563 |
| dev. +/- | 3.473597 | 1.75371 |
| beta | 0.081461 | 0.170243 |
| M.S.E. | 0.525792 | 0.671167 |
| S.E.(A) | 0.111228 | 0.125667 |

FIG. 7F-4

| PATIENT 17: | | Table 1 #9 | |
|---|---|---|---|
| DOT m/d/y | | AGE | 46 |
| 10/31/97 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 1 | 2 | |
| 2 | 3 | 1 | |
| 3 | 2 | 4 | |
| 4 | 5 | 3 | |
| 5 | 4 | 5 | |
| 6 | 6 | 6 | |
| 7 | 7 | 7 | |
| 8 | 8 | 8 | |
| 9 | 9 | 9 | |
| 10 | 10 | 10 | |
| 11 | 11 | 11 | |
| 12 | 12 | 12 | |
| 13 | 13 | 13 | |
| 14 | 14 | 14 | |
| 15 | 15 | 15 | |
| 16 | 16 | 16 | |
| 17 | 17 | 17 | |
| 18 | 18 | 18 | |
| 19 | 20 | 19 | |
| 20 | 19 | 20 | |
| 21 | 21 | 21 | |
| 22 | 22 | 22 | |

| PATIENT 18: | | Table 1 #13 | |
|---|---|---|---|
| DOT m/d/y | | AGE | 66 |
| 1/22/98 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 1 | 1 | |
| 2 | 2 | 2 | |
| 3 | 3 | 3 | |
| 4 | 5 | 4 | |
| 5 | 4 | 5 | |
| 6 | 6 | 6 | |
| 7 | 7 | 7 | |
| 8 | 8 | 8 | |
| 9 | 9 | 9 | |
| 10 | 10 | 10 | |
| 11 | 11 | 11 | |
| 12 | 12 | 12 | |
| 13 | 13 | 13 | |
| 14 | 14 | 14 | |
| 15 | 15 | 15 | |
| 16 | 16 | 16 | |
| 17 | 17 | 17 | |
| 18 | 18 | 18 | |
| 19 | 19 | 19 | |
| 20 | 20 | 20 | |
| 21 | 21 | 21 | |
| 22 | 22 | 22 | |

| PATIENT 19: | | Table 3 #3 | |
|---|---|---|---|
| DOT m/d/y | | AGE | 69 |
| 10/6/97 | 1st EYE | 2nd EYE | |
| EYE | RIGHT | left | |
| Reference | PLACEMEN | PLACEMENT | |
| cap position | cap position | cap position | |
| 85 | 1 | 85 | |
| 1 | 2 | 2 | |
| 2 | 85 | 1 | |
| 3 | 3 | 3 | |
| 4 | 4 | 4 | |
| 5 | 5 | 7 | |
| 6 | 8 | 6 | |
| 7 | 6 | 5 | |
| 8 | 7 | 10 | |
| 9 | 9 | 8 | |
| 10 | 11 | 12 | |
| 11 | 10 | 9 | |
| 12 | 12 | 11 | |
| 13 | 13 | 14 | |
| 14 | 14 | 13 | |
| 15 | 15 | 15 | |
| 16 | 16 | 17 | |
| 17 | 17 | 16 | |
| 18 | 18 | 18 | |
| 19 | 20 | 21 | |
| 20 | 19 | 20 | |
| 21 | 21 | 19 | |
| 22 | 22 | 22 | |

FIG. 7G-1

| | | | | | | | | |
|---|---|---|---|---|---|---|---|---|
| 23 | 23 | 23 | 23 | 23 | 23 | 23 | 23 | 25 |
| 24 | 24 | 24 | 24 | 24 | 24 | 24 | 25 | 23 |
| 25 | 25 | 25 | 25 | 25 | 25 | 25 | 24 | 24 |
| 26 | 26 | 26 | 26 | 26 | 26 | 26 | 28 | 27 |
| 27 | 27 | 27 | 27 | 27 | 27 | 27 | 29 | 26 |
| 28 | 28 | 28 | 28 | 28 | 28 | 28 | 30 | 31 |
| 29 | 29 | 29 | 29 | 30 | 29 | 29 | 26 | 29 |
| 30 | 30 | 30 | 30 | 29 | 30 | 30 | 27 | 30 |
| 31 | 31 | 31 | 31 | 31 | 31 | 31 | 32 | 28 |
| 32 | 33 | 32 | 32 | 32 | 32 | 32 | 31 | 32 |
| 33 | 32 | 34 | 33 | 33 | 33 | 33 | 33 | 33 |
| 34 | 34 | 33 | 34 | 34 | 34 | 34 | 34 | 35 |
| 35 | 35 | 35 | 35 | 35 | 35 | 35 | 37 | 36 |
| 36 | 36 | 36 | 36 | 36 | 36 | 36 | 35 | 34 |
| 37 | 37 | 37 | 37 | 37 | 37 | 37 | 36 | 41 |
| 38 | 40 | 38 | 38 | 38 | 38 | 38 | 40 | 42 |
| 39 | 39 | 39 | 39 | 39 | 39 | 39 | 38 | 39 |
| 40 | 38 | 40 | 40 | 40 | 40 | 40 | 39 | 37 |
| 41 | 41 | 41 | 41 | 41 | 42 | 41 | 41 | 38 |
| 42 | 42 | 42 | 42 | 42 | 41 | 42 | 42 | 40 |
| 43 | 43 | 43 | 43 | 43 | 43 | 43 | 43 | 44 |
| 44 | 45 | 45 | 44 | 46 | 45 | 44 | 44 | 45 |
| 45 | 44 | 44 | 45 | 47 | 46 | 45 | 49 | 46 |
| 46 | 46 | 46 | 46 | 44 | 44 | 46 | 50 | 43 |
| 47 | 47 | 47 | 47 | 45 | 47 | 47 | 46 | 48 |
| 48 | 49 | 48 | 48 | 48 | 48 | 48 | 47 | 47 |
| 49 | 48 | 49 | 49 | 49 | 49 | 49 | 45 | 50 |
| 50 | 50 | 50 | 50 | 50 | 50 | 50 | 48 | 52 |
| 51 | 51 | 51 | 51 | 51 | 51 | 51 | 51 | 51 |
| 52 | 52 | 52 | 52 | 52 | 52 | 52 | 52 | 49 |
| 53 | 53 | 53 | 53 | 53 | 53 | 53 | 53 | 53 |
| 54 | 54 | 54 | 54 | 54 | 54 | 54 | 55 | 56 |
| 55 | 55 | 56 | 55 | 55 | 55 | 55 | 56 | 54 |

FIG. 7G-2

| | | | | | | | | |
|---|---|---|---|---|---|---|---|---|
| 56 | 56 | 55 | 56 | 56 | 56 | 56 | 54 | 55 |
| 57 | 57 | 57 | 57 | 57 | 57 | 57 | 57 | 57 |
| 58 | 58 | 58 | 58 | 58 | 58 | 58 | 58 | 60 |
| 59 | 59 | 59 | 59 | 59 | 59 | 59 | 59 | 58 |
| 60 | 60 | 60 | 60 | 60 | 60 | 60 | 60 | 59 |
| 61 | 61 | 61 | 61 | 62 | 61 | 61 | 62 | 61 |
| 62 | 62 | 62 | 62 | 61 | 62 | 62 | 63 | 63 |
| 63 | 63 | 63 | 63 | 63 | 63 | 63 | 61 | 62 |
| 64 | 64 | 64 | 64 | 64 | 64 | 64 | 64 | 64 |
| 65 | 65 | 65 | 65 | 65 | 66 | 65 | 64 | 65 |
| 66 | 66 | 66 | 66 | 66 | 65 | 66 | 66 | 66 |
| 67 | 67 | 67 | 67 | 67 | 67 | 67 | 69 | 68 |
| 68 | 68 | 68 | 68 | 68 | 68 | 68 | 68 | 67 |
| 69 | 69 | 69 | 69 | 69 | 69 | 69 | 67 | 71 |
| 70 | 70 | 71 | 70 | 70 | 70 | 70 | 70 | 69 |
| 71 | 71 | 70 | 71 | 71 | 71 | 71 | 71 | 70 |
| 72 | 72 | 72 | 72 | 72 | 72 | 72 | 72 | 72 |
| 73 | 73 | 73 | 73 | 73 | 73 | 73 | 73 | 74 |
| 74 | 74 | 74 | 74 | 74 | 74 | 74 | 74 | 75 |
| 75 | 75 | 75 | 75 | 75 | 75 | 75 | 78 | 76 |
| 76 | 76 | 77 | 76 | 77 | 76 | 76 | 77 | 73 |
| 77 | 77 | 76 | 77 | 76 | 77 | 77 | 76 | 78 |
| 78 | 79 | 79 | 78 | 78 | 79 | 78 | 75 | 77 |
| 79 | 78 | 78 | 79 | 79 | 78 | 79 | 79 | 83 |
| 80 | 82 | 80 | 80 | 80 | 80 | 80 | 83 | 81 |
| 81 | 80 | 83 | 81 | 81 | 81 | 81 | 84 | 84 |
| 82 | 83 | 82 | 82 | 82 | 82 | 82 | 82 | 82 |
| 83 | 81 | 81 | 83 | 83 | 83 | 83 | 81 | 79 |
| 84 | 84 | 84 | 84 | 84 | 84 | 84 | 80 | 80 |

FIG. 7G-3

| | Table 1 #9 | |
|---|---|---|
| age | 46 | |
| Error score | 52 | 40 |
| Mean error | 2.611765 | 2.470588 |
| SQRT of erro | 7.211103 | 6.324555 |
| B+Y SQRT | 7 | 5.385165 |
| R+G SQRT | 2.645751 | 3.162278 |
| Quad. axis | 4.354249 | 2.222887 |
| BINOCULARLY NORMAL | | |
| On eye to eye comparison | | |
| 0.636547231 | | |
| Box 1 SQRT | 3.464102 | 2.645751 |
| Box 2 SQRT | 3.605551 | 2.236068 |
| Box 3 SQRT | 2.645751 | 2.645751 |
| Box 4 SQRT | 4.472136 | 4.582576 |
| Amp. sine | 0.786957 | 0.501771 |
| C.M.A. | 83.03721 | 81.78055 |
| | 40.53373 | 39.27707 |
| dev. +/- | 0.964458 | 1.260728 |
| beta | 0.301312 | 0.203098 |
| M.S.E. | 0.535119 | 0.371736 |
| S.E.(A) | 0.11221 | 0.093524 |

| | Table 1 #13 | |
|---|---|---|
| age | 66 | |
| Error score | 28 | 20 |
| Mean error | 2.329412 | 2.235294 |
| SQRT of erro | 5.291503 | 4.472136 |
| B+Y SQRT | 4.358899 | 4 |
| R+G SQRT | 3 | 2 |
| Quad. axis | 1.358899 | 2 |
| BINOCULARLY NORMAL | | |
| On eye to eye comparison | | |
| 0.569366667 | | |
| Box 1 SQRT | 2 | 0 |
| Box 2 SQRT | 2.44949 | 2.236068 |
| Box 3 SQRT | 3.741657 | 2.828427 |
| Box 4 SQRT | 2 | 2.645751 |
| Amp. sine | 0.231069 | 0.231963 |
| C.M.A. | 0.867365 | 83.61968 |
| | 43.36389 | 41.1162 |
| dev. +/- | 2.64766 | 2.369435 |
| beta | 0.099196 | 0.103773 |
| M.S.E. | 0.347689 | 0.280613 |
| S.E.(A) | 0.090448 | 0.081257 |

| | Table 3 #3 | |
|---|---|---|
| age | 69 | 208 |
| Error score | 140 | 4.447059 |
| Mean error | 3.647059 | 14.42221 |
| SQRT of erro | 11.83216 | 11.13553 |
| B+Y SQRT | 9.327379 | 9.055385 |
| R+G SQRT | 7.348469 | 2.080144 |
| Quad. axis | 1.97891 | |
| 95% BINOC ERROR | | |
| On eye to eye comparison | | |
| 2.840045536 | | |
| Box 1 SQRT | 5 | 7 |
| Box 2 SQRT | 6.324555 | 7.681146 |
| Box 3 SQRT | 6.324555 | 6.557439 |
| Box 4 SQRT | 5.91608 | 7.549834 |
| Amp. sine | 0.665888 | 0.641126 |
| C.M.A. | 81.98512 | 83.27127 |
| | 39.48164 | 40.76779 |
| dev. +/- | 2.111464 | 2.623866 |
| beta | 0.182582 | 0.144168 |
| M.S.E. | 1.836336 | 2.628764 |
| S.E.(A) | 0.207865 | 0.248703 |

FIG. 7G-4

PATIENT 20: Table 3 #2

| | | | |
|---|---|---|---|
| DOT m/d/y | | AGE | 62 |
| 11/6/97 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 1 | 1 | |
| 2 | 2 | 2 | |
| 3 | 3 | 3 | |
| 4 | 4 | 4 | |
| 5 | 5 | 5 | |
| 6 | 6 | 7 | |
| 7 | 7 | 6 | |
| 8 | 8 | 8 | |
| 9 | 9 | 9 | |
| 10 | 10 | 10 | |
| 11 | 11 | 11 | |
| 12 | 12 | 12 | |
| 13 | 13 | 14 | |
| 14 | 15 | 13 | |
| 15 | 14 | 15 | |
| 16 | 16 | 16 | |
| 17 | 17 | 17 | |
| 18 | 18 | 18 | |
| 19 | 19 | 19 | |
| 20 | 20 | 20 | |
| 21 | 21 | 21 | |
| 22 | 22 | 22 | |

FIG. 7H-1

| | | |
|---|---|---|
| 23 | 23 | 23 |
| 24 | 24 | 24 |
| 25 | 25 | 25 |
| 26 | 26 | 26 |
| 27 | 27 | 27 |
| 28 | 29 | 28 |
| 29 | 28 | 29 |
| 30 | 30 | 30 |
| 31 | 31 | 31 |
| 32 | 32 | 32 |
| 33 | 33 | 33 |
| 34 | 34 | 34 |
| 35 | 35 | 35 |
| 36 | 36 | 36 |
| 37 | 38 | 37 |
| 38 | 37 | 38 |
| 39 | 39 | 39 |
| 40 | 40 | 40 |
| 41 | 41 | 42 |
| 42 | 42 | 41 |
| 43 | 44 | 43 |
| 44 | 43 | 45 |
| 45 | 45 | 44 |
| 46 | 46 | 46 |
| 47 | 48 | 47 |
| 48 | 47 | 49 |
| 49 | 49 | 48 |
| 50 | 50 | 50 |
| 51 | 51 | 51 |
| 52 | 52 | 53 |
| 53 | 54 | 52 |
| 54 | 53 | 54 |
| 55 | 55 | 55 |

FIG. 7H-2

| | | |
|---|---|---|
| 56 | 57 | 56 |
| 57 | 56 | 57 |
| 58 | 58 | 58 |
| 59 | 59 | 59 |
| 60 | 60 | 61 |
| 61 | 61 | 60 |
| 62 | 62 | 62 |
| 63 | 63 | 63 |
| 64 | 64 | 64 |
| 65 | 65 | 66 |
| 66 | 66 | 65 |
| 67 | 68 | 67 |
| 68 | 67 | 68 |
| 69 | 69 | 69 |
| 70 | 70 | 70 |
| 71 | 71 | 71 |
| 72 | 72 | 72 |
| 73 | 73 | 73 |
| 74 | 74 | 75 |
| 75 | 75 | 74 |
| 76 | 76 | 77 |
| 77 | 78 | 76 |
| 78 | 77 | 78 |
| 79 | 79 | 79 |
| 80 | 80 | 80 |
| 81 | 82 | 82 |
| 82 | 81 | 83 |
| 83 | 84 | 84 |
| 84 | 83 | 81 |

FIG. 7H-3

Table 3 #2

| | | |
|---|---|---|
| age | 62 | |
| Error score | 44 | 48 |
| Mean error | 2.517647 | 2.564706 |
| SQRT of erro | 6.63325 | 6.928203 |
| B+Y SQRT | 5.477226 | 6 |
| R+G SQRT | 4.123106 | 3.872983 |
| Quad. axis | 1.35412 | 2.127017 |
| BINOCULARLY NORMAL | | |
| On eye to eye comparison | | |
| 0.54495365 | | |
| | | |
| Box 1 SQRT | 2 | 2.828427 |
| Box 2 SQRT | 3.162278 | 2.236068 |
| Box 3 SQRT | 3.741657 | 4 |
| Box 4 SQRT | 4 | 4.358899 |
| | | |
| Amp. sine | 0.218047 | 0.291361 |
| | | |
| C.M.A. | 84.58224 | 1.860217 |
| | 42.07876 | 44.35674 |
| dev. +/- | 2.638185 | 2.704324 |
| | | |
| beta | 0.086607 | 0.113604 |
| M.S.E. | 0.307392 | 0.576715 |
| S.E.(A) | 0.085046 | 0.116489 |

FIG. 7H-4

| PATIENT 21: | | Table 1 #10 | |
|---|---|---|---|
| DOT m/d/y | | AGE | 66 |
| 10/27/97 | 1st EYE | 2nd EYE | |
| EYE | RIGHT | left | |
| Reference | PLACEMEN | PLACEMENT | |
| cap position | cap position | cap position | |
| 85 | 85 | 1 | |
| 1 | 1 | 85 | |
| 2 | 2 | 2 | |
| 3 | 4 | 3 | |
| 4 | 3 | 5 | |
| 5 | 5 | 4 | |
| 6 | 6 | 6 | |
| 7 | 7 | 7 | |
| 8 | 8 | 8 | |
| 9 | 9 | 9 | |
| 10 | 10 | 11 | |
| 11 | 11 | 10 | |
| 12 | 12 | 12 | |
| 13 | 14 | 13 | |
| 14 | 13 | 14 | |
| 15 | 15 | 15 | |
| 16 | 16 | 16 | |
| 17 | 17 | 17 | |
| 18 | 18 | 18 | |
| 19 | 19 | 19 | |
| 20 | 20 | 20 | |
| 21 | 21 | 21 | |

| PATIENT 22: | | Table 1 #6 | |
|---|---|---|---|
| DOT m/d/y | | AGE | 45 |
| 9/22/97 | 1st EYE | 2nd EYE | |
| EYE | RIGHT | left | |
| Reference | PLACEMEN | PLACEMENT | |
| cap position | cap position | cap position | |
| 85 | 85 | 1 | |
| 1 | 1 | 85 | |
| 2 | 2 | 2 | |
| 3 | 3 | 3 | |
| 4 | 5 | 5 | |
| 5 | 4 | 4 | |
| 6 | 6 | 6 | |
| 7 | 7 | 7 | |
| 8 | 8 | 9 | |
| 9 | 10 | 8 | |
| 10 | 9 | 10 | |
| 11 | 11 | 11 | |
| 12 | 12 | 12 | |
| 13 | 15 | 13 | |
| 14 | 13 | 14 | |
| 15 | 14 | 15 | |
| 16 | 16 | 17 | |
| 17 | 17 | 16 | |
| 18 | 18 | 18 | |
| 19 | 19 | 20 | |
| 20 | 21 | 19 | |
| 21 | 20 | 21 | |

| PATIENT 23: | | Table 1 #8 | |
|---|---|---|---|
| DOT m/d/y | | AGE | 50 |
| 10/21/97 | 1st EYE | 2nd EYE | |
| EYE | RIGHT | left | |
| Reference | PLACEMEN | PLACEMENT | |
| cap position | cap position | cap position | |
| 85 | 1 | 2 | |
| 1 | 85 | 85 | |
| 2 | 2 | 1 | |
| 3 | 4 | 4 | |
| 4 | 5 | 3 | |
| 5 | 3 | 5 | |
| 6 | 7 | 7 | |
| 7 | 6 | 6 | |
| 8 | 8 | 8 | |
| 9 | 9 | 9 | |
| 10 | 10 | 10 | |
| 11 | 11 | 11 | |
| 12 | 12 | 12 | |
| 13 | 13 | 14 | |
| 14 | 16 | 13 | |
| 15 | 14 | 16 | |
| 16 | 15 | 15 | |
| 17 | 18 | 18 | |
| 18 | 17 | 17 | |
| 19 | 19 | 19 | |
| 20 | 20 | 21 | |
| 21 | 21 | 20 | |

FIG. 7I-1

| | | | | | | | | |
|---|---|---|---|---|---|---|---|---|
| 22 | 22 | 22 | 22 | 22 | 22 | 22 | 23 | 25 |
| 23 | 23 | 23 | 23 | 23 | 23 | 23 | 22 | 23 |
| 24 | 24 | 24 | 24 | 25 | 26 | 24 | 24 | 22 |
| 25 | 25 | 25 | 25 | 24 | 25 | 25 | 26 | 24 |
| 26 | 26 | 26 | 26 | 26 | 24 | 26 | 25 | 26 |
| 27 | 27 | 27 | 27 | 29 | 27 | 27 | 27 | 28 |
| 28 | 28 | 28 | 28 | 30 | 28 | 28 | 28 | 27 |
| 29 | 29 | 29 | 29 | 27 | 29 | 29 | 29 | 29 |
| 30 | 30 | 30 | 30 | 28 | 30 | 30 | 31 | 31 |
| 31 | 31 | 31 | 31 | 31 | 31 | 31 | 30 | 30 |
| 32 | 32 | 33 | 32 | 33 | 32 | 32 | 32 | 32 |
| 33 | 34 | 32 | 33 | 32 | 35 | 33 | 34 | 35 |
| 34 | 33 | 34 | 34 | 34 | 34 | 34 | 33 | 33 |
| 35 | 35 | 35 | 35 | 35 | 33 | 35 | 35 | 34 |
| 36 | 36 | 36 | 36 | 36 | 36 | 36 | 36 | 40 |
| 37 | 38 | 38 | 37 | 38 | 38 | 37 | 39 | 39 |
| 38 | 37 | 37 | 38 | 37 | 37 | 38 | 40 | 36 |
| 39 | 39 | 39 | 39 | 41 | 39 | 39 | 37 | 38 |
| 40 | 42 | 40 | 40 | 40 | 41 | 40 | 38 | 37 |
| 41 | 41 | 42 | 41 | 39 | 42 | 41 | 42 | 41 |
| 42 | 40 | 41 | 42 | 42 | 40 | 42 | 41 | 42 |
| 43 | 43 | 43 | 43 | 43 | 43 | 43 | 45 | 44 |
| 44 | 44 | 44 | 44 | 44 | 44 | 44 | 48 | 45 |
| 45 | 46 | 45 | 45 | 45 | 46 | 45 | 43 | 43 |
| 46 | 45 | 46 | 46 | 47 | 45 | 46 | 44 | 47 |
| 47 | 47 | 48 | 47 | 46 | 47 | 47 | 46 | 46 |
| 48 | 48 | 47 | 48 | 49 | 49 | 48 | 49 | 50 |
| 49 | 49 | 49 | 49 | 48 | 48 | 49 | 47 | 49 |
| 50 | 50 | 51 | 50 | 50 | 52 | 50 | 50 | 51 |
| 51 | 53 | 50 | 51 | 52 | 51 | 51 | 52 | 48 |
| 52 | 52 | 53 | 52 | 51 | 50 | 52 | 53 | 52 |

FIG. 7I-2

| | | | | | | | | |
|---|---|---|---|---|---|---|---|---|
| 53 | 51 | 52 | 53 | 53 | 53 | 53 | 51 | 54 |
| 54 | 54 | 54 | 54 | 55 | 55 | 54 | 54 | 53 |
| 55 | 55 | 55 | 55 | 54 | 54 | 55 | 55 | 55 |
| 56 | 56 | 56 | 56 | 57 | 57 | 56 | 57 | 56 |
| 57 | 57 | 57 | 57 | 56 | 56 | 57 | 56 | 58 |
| 58 | 58 | 58 | 58 | 59 | 58 | 58 | 59 | 57 |
| 59 | 59 | 59 | 59 | 58 | 59 | 59 | 58 | 59 |
| 60 | 60 | 60 | 60 | 60 | 61 | 60 | 60 | 60 |
| 61 | 61 | 61 | 61 | 61 | 60 | 61 | 61 | 61 |
| 62 | 62 | 62 | 62 | 62 | 62 | 62 | 62 | 62 |
| 63 | 63 | 63 | 63 | 63 | 63 | 63 | 63 | 63 |
| 64 | 64 | 64 | 64 | 64 | 65 | 64 | 64 | 64 |
| 65 | 65 | 66 | 65 | 66 | 64 | 65 | 65 | 66 |
| 66 | 66 | 65 | 66 | 65 | 66 | 66 | 66 | 65 |
| 67 | 67 | 67 | 67 | 67 | 67 | 67 | 67 | 67 |
| 68 | 68 | 68 | 68 | 70 | 68 | 68 | 69 | 68 |
| 69 | 69 | 69 | 69 | 71 | 69 | 69 | 68 | 70 |
| 70 | 71 | 71 | 70 | 69 | 70 | 70 | 70 | 69 |
| 71 | 70 | 70 | 71 | 68 | 72 | 71 | 71 | 71 |
| 72 | 72 | 72 | 72 | 72 | 71 | 72 | 72 | 72 |
| 73 | 73 | 73 | 73 | 73 | 73 | 73 | 73 | 73 |
| 74 | 74 | 74 | 74 | 74 | 74 | 74 | 74 | 74 |
| 75 | 75 | 75 | 75 | 77 | 77 | 75 | 76 | 75 |
| 76 | 77 | 78 | 76 | 76 | 75 | 76 | 75 | 76 |
| 77 | 76 | 77 | 77 | 75 | 76 | 77 | 77 | 77 |
| 78 | 78 | 76 | 78 | 79 | 79 | 78 | 79 | 78 |
| 79 | 79 | 79 | 79 | 78 | 78 | 79 | 81 | 81 |
| 80 | 80 | 80 | 80 | 80 | 80 | 80 | 78 | 79 |
| 81 | 82 | 82 | 81 | 81 | 81 | 81 | 80 | 83 |
| 82 | 81 | 81 | 82 | 83 | 82 | 82 | 84 | 82 |
| 83 | 83 | 83 | 83 | 82 | 83 | 83 | 82 | 80 |
| 84 | 84 | 84 | 84 | 84 | 84 | 84 | 83 | 84 |

FIG. 7I-3

Table 1 #10

| | | |
|---|---|---|
| age | 66 | |
| Error score | 48 | 56 |
| Mean error | 2.564706 | 2.658824 |
| SQRT of erro | 6.928203 | 7.483315 |
| B+Y SQRT | 6.403124 | 6.480741 |
| R+G SQRT | 3.162278 | 3.605551 |
| Quad. axis | 3.240847 | 2.875189 |
| BINOCULARLY NORMAL | | |
| On eye to eye comparison | | |
| 0.805111543 | | |
| Box 1 SQRT | 2.645751 | 3.162278 |
| Box 2 SQRT | 4 | 3.464102 |
| Box 3 SQRT | 3.464102 | 3.605551 |
| Box 4 SQRT | 3.605551 | 4.582576 |
| Amp. sine | 0.48898 | 0.467053 |
| C.M.A. | 84.15298 | 83.70576 |
| | 41.6495 | 41.20228 |
| dev. +/- | 1.340752 | 1.19787 |
| beta | 0.190657 | 0.175661 |
| M.S.E. | 0.399265 | 0.290759 |
| S.E.(A) | 0.096925 | 0.082713 |

Table 1 #6

| | | |
|---|---|---|
| age | 45 | |
| Error score | 108 | 96 |
| Mean error | 3.2705882 | 3.1294118 |
| SQRT of erro | 10.392305 | 9.797959 |
| B+Y SQRT | 7.6811457 | 7.4161985 |
| R+G SQRT | 7.6811457 | 6.3245553 |
| Quad. axis | 0 | 1.0916432 |
| BINOCULARLY NORMAL | | |
| On eye to eye comparison | | |
| 0.344345874 | | |
| Box 1 SQRT | 4.358899 | 4.242641 |
| Box 2 SQRT | 5.656854 | 5.291503 |
| Box 3 SQRT | 5 | 5.477226 |
| Box 4 SQRT | 5.656854 | 4.472136 |
| Amp. sine | 0.2791564 | 0.2021431 |
| C.M.A. | 71.434759 | 0.3948014 |
| | 28.93128 | 42.891322 |
| dev. +/- | 3.3711943 | 4.2357456 |
| beta | 0.0853536 | 0.0645946 |
| M.S.E. | 0.8227058 | 0.6810193 |
| S.E.(A) | 0.1391322 | 0.1265859 |

Table 1 #8

| | | |
|---|---|---|
| age | 50 | |
| Error score | 136 | 144 |
| Mean error | 3.6 | 3.694118 |
| SQRT of erro | 11.6619 | 12 |
| B+Y SQRT | 10.3923 | 9.746794 |
| R+G SQRT | 6.324555 | 7.141428 |
| Quad. axis | 4.06775 | 2.605366 |
| BINOCULARLY NORMAL | | |
| On eye to eye comparison | | |
| 0.58809621 | | |
| Box 1 SQRT | 5.567764 | 5.656854 |
| Box 2 SQRT | 5.91608 | 7.071068 |
| Box 3 SQRT | 6.244998 | 5.656854 |
| Box 4 SQRT | 5.567764 | 5.477226 |
| Amp. sine | 1.124726409 | 0.724686 |
| C.M.A. | 1.259121778 | 83.82811 |
| | 43.75564278 | 41.32464 |
| dev. +/- | 0.937346825 | 1.842092 |
| beta | 0.312424003 | 0.196173 |
| M.S.E. | 1.032466913 | 1.655404 |
| S.E.(A) | 0.155863 | 0.197359 |

FIG. 7I-4

| PATIENT 24: | | Table 3 #4 | |
|---|---|---|---|
| DOT m/d/y | | AGE | 57 |
| 11/14/97 | 1st EYE | 2nd EYE | |
| EYE | RIGHT | left | |
| Reference | PLACEMENT | PLACEMENT | |
| cap position | cap position | cap position | |
| 85 | 85 | 85 | |
| 1 | 1 | 1 | |
| 2 | 2 | 2 | |
| 3 | 3 | 3 | |
| 4 | 4 | 4 | |
| 5 | 5 | 5 | |
| 6 | 6 | 6 | |
| 7 | 7 | 7 | |
| 8 | 8 | 8 | |
| 9 | 9 | 9 | |
| 10 | 10 | 10 | |
| 11 | 11 | 11 | |
| 12 | 12 | 12 | |
| 13 | 13 | 13 | |
| 14 | 14 | 14 | |
| 15 | 15 | 15 | |
| 16 | 16 | 16 | |
| 17 | 17 | 17 | |
| 18 | 18 | 18 | |
| 19 | 19 | 19 | |
| 20 | 20 | 20 | |
| 21 | 21 | 21 | |

| PATIENT 25: | | Table 3 #1 | |
|---|---|---|---|
| DOT m/d/y | | AGE | 45 |
| 10/28/97 | 1st EYE | 2nd EYE | |
| EYE | RIGHT | left | |
| Reference | PLACEMEN | PLACEMENT | |
| cap position | cap position | cap position | |
| 85 | 85 | 85 | |
| 1 | 1 | 1 | |
| 2 | 2 | 2 | |
| 3 | 4 | 4 | |
| 4 | 3 | 3 | |
| 5 | 5 | 5 | |
| 6 | 6 | 6 | |
| 7 | 7 | 7 | |
| 8 | 9 | 9 | |
| 9 | 8 | 8 | |
| 10 | 10 | 10 | |
| 11 | 11 | 11 | |
| 12 | 12 | 12 | |
| 13 | 13 | 13 | |
| 14 | 14 | 14 | |
| 15 | 16 | 16 | |
| 16 | 15 | 15 | |
| 17 | 17 | 18 | |
| 18 | 18 | 20 | |
| 19 | 19 | 17 | |
| 20 | 21 | 19 | |
| 21 | 20 | 21 | |

FIG. 7J-1

| | | | | | |
|---|---|---|---|---|---|
| 22 | 22 | 22 | 22 | 24 | 22 |
| 23 | 23 | 23 | 23 | 22 | 23 |
| 24 | 24 | 24 | 24 | 23 | 24 |
| 25 | 25 | 25 | 25 | 25 | 27 |
| 26 | 26 | 26 | 26 | 26 | 25 |
| 27 | 27 | 28 | 27 | 29 | 26 |
| 28 | 28 | 27 | 28 | 27 | 28 |
| 29 | 29 | 30 | 29 | 28 | 30 |
| 30 | 31 | 29 | 30 | 31 | 29 |
| 31 | 30 | 31 | 31 | 30 | 31 |
| 32 | 32 | 32 | 32 | 32 | 34 |
| 33 | 33 | 34 | 33 | 33 | 33 |
| 34 | 34 | 33 | 34 | 34 | 32 |
| 35 | 35 | 35 | 35 | 35 | 35 |
| 36 | 36 | 36 | 36 | 36 | 37 |
| 37 | 37 | 37 | 37 | 38 | 36 |
| 38 | 38 | 38 | 38 | 37 | 38 |
| 39 | 39 | 39 | 39 | 40 | 39 |
| 40 | 40 | 40 | 40 | 41 | 40 |
| 41 | 42 | 42 | 41 | 39 | 42 |
| 42 | 41 | 41 | 42 | 42 | 41 |
| 43 | 43 | 43 | 43 | 43 | 43 |
| 44 | 47 | 46 | 44 | 44 | 45 |
| 45 | 46 | 47 | 45 | 45 | 44 |
| 46 | 44 | 48 | 46 | 47 | 46 |
| 47 | 45 | 44 | 47 | 48 | 47 |
| 48 | 48 | 45 | 48 | 46 | 51 |
| 49 | 49 | 49 | 49 | 49 | 48 |
| 50 | 50 | 50 | 50 | 50 | 49 |
| 51 | 51 | 51 | 51 | 53 | 52 |
| 52 | 52 | 52 | 52 | 51 | 53 |

FIG. 7J-2

| | | | | | |
|---|---|---|---|---|---|
| 53 | 53 | 53 | 53 | 54 | 50 |
| 54 | 54 | 55 | 54 | 52 | 54 |
| 55 | 55 | 54 | 55 | 56 | 55 |
| 56 | 56 | 56 | 56 | 55 | 56 |
| 57 | 57 | 57 | 57 | 58 | 57 |
| 58 | 58 | 58 | 58 | 59 | 58 |
| 59 | 59 | 59 | 59 | 57 | 61 |
| 60 | 60 | 60 | 60 | 62 | 62 |
| 61 | 61 | 62 | 61 | 61 | 59 |
| 62 | 62 | 61 | 62 | 60 | 60 |
| 63 | 63 | 63 | 63 | 63 | 63 |
| 64 | 64 | 64 | 64 | 64 | 65 |
| 65 | 65 | 65 | 65 | 65 | 64 |
| 66 | 66 | 67 | 66 | 66 | 66 |
| 67 | 67 | 66 | 67 | 67 | 67 |
| 68 | 68 | 68 | 68 | 68 | 69 |
| 69 | 69 | 69 | 69 | 69 | 68 |
| 70 | 70 | 70 | 70 | 71 | 70 |
| 71 | 71 | 71 | 71 | 70 | 72 |
| 72 | 72 | 72 | 72 | 72 | 71 |
| 73 | 73 | 73 | 73 | 73 | 74 |
| 74 | 74 | 74 | 74 | 74 | 73 |
| 75 | 76 | 75 | 75 | 75 | 75 |
| 76 | 77 | 76 | 76 | 76 | 76 |
| 77 | 75 | 77 | 77 | 77 | 77 |
| 78 | 78 | 79 | 78 | 79 | 78 |
| 79 | 79 | 78 | 79 | 78 | 80 |
| 80 | 81 | 80 | 80 | 81 | 79 |
| 81 | 80 | 81 | 81 | 80 | 81 |
| 82 | 82 | 82 | 82 | 83 | 84 |
| 83 | 83 | 83 | 83 | 84 | 83 |
| 84 | 84 | 84 | 84 | 82 | 82 |

FIG. 7J-3

Table 3 #4

| | | |
|---|---|---|
| age | 57 | |
| Error score | 32 | 48 |
| Mean error | 2.3764706 | 2.564706 |
| SQRT of erro | 5.6568542 | 6.928203 |
| B+Y SQRT | 4.8989795 | 5.291503 |
| R+G SQRT | 2.8284271 | 4.472136 |
| Quad. axis | 2.0705524 | 0.819367 |
| BINOCULARLY NORMAL | | |
| On eye to eye comparison | | |
| 1.521348981 | | |
| Box 1 SQRT | 0 | 0 |
| Box 2 SQRT | 3.3166248 | 4.242641 |
| Box 3 SQRT | 3 | 4.690416 |
| Box 4 SQRT | 3.4641016 | 2.828427 |
| Amp. sine | 0.4897892 | 0.214529 |
| C.M.A. | 81.789446 | 82.45599 |
| | 39.285967 | 39.95251 |
| dev. +/- | 1.4751453 | 3.958818 |
| beta | 0.2060994 | 0.083646 |
| M.S.E. | 0.4849195 | 0.670013 |
| S.E.(A) | 0.106817 | 0.125559 |

Table 3 #1

| | | |
|---|---|---|
| age | 45 | |
| Error score | 112 | 120 |
| Mean error | 3.317647 | 3.411765 |
| SQRT of erro | 10.58301 | 10.95445 |
| B+Y SQRT | 8.185353 | 7.681146 |
| R+G SQRT | 7.28011 | 7.745967 |
| Quad. axis | 0.905243 | -0.06482 |
| BINOCULARLY NORMAL | | |
| On eye to eye comparison | | |
| 0.621445906 | | |
| Box 1 SQRT | 4.242641 | 4.898979 |
| Box 2 SQRT | 5.477226 | 5.385165 |
| Box 3 SQRT | 6.63325 | 6.403124 |
| Box 4 SQRT | 4.472136 | 5.09902 |
| Amp. sine | 0.299799 | 0.172437 |
| C.M.A. | 10.28266 | 15.84494 |
| | 52.77918 | 58.34146 |
| dev. +/- | 3.908834 | 6.418971 |
| beta | 0.090365 | 0.050542 |
| M.S.E. | 1.275662 | 1.138077 |
| S.E.(A) | 0.17325 | 0.163641 |

FIG. 7J-4

This patient provides an example of color vision error detected by Ishihara plates (IP).
Patient is classified as having errors by (IP).

| | | | |
|---|---|---|---|
| PATIENT 26: | | NON_CANCER Deutan (genetic error) | |
| Code # | white | male | |
| DOT m/d/y | | AGE | 28 |
| | 1st EYE | 2nd EYE | |
| EYE | RIGHT | left | |
| Reference cap position | PLACEMEN cap position | PLACEMENT cap position | |
| 85 | 85 | 85 | |
| 1 | 1 | 1 | |
| 2 | 2 | 2 | |
| 3 | 3 | 3 | |
| 4 | 4 | 4 | |
| 5 | 5 | 5 | |
| 6 | 6 | 6 | |
| 7 | 8 | 8 | |
| 8 | 7 | 7 | |
| 9 | 10 | 10 | |
| 10 | 9 | 9 | |
| 11 | 11 | 12 | |
| 12 | 12 | 11 | |
| 13 | 14 | 13 | |
| 14 | 13 | 15 | |
| 15 | 17 | 14 | |
| 16 | 16 | 16 | |
| 17 | 15 | 17 | |
| 18 | 18 | 19 | |
| 19 | 19 | 18 | |
| 20 | 20 | 20 | |
| 21 | 21 | 21 | |

FIG. 7K-1

| | | |
|---|---|---|
| 22 | 22 | 22 |
| 23 | 23 | 23 |
| 24 | 24 | 26 |
| 25 | 26 | 25 |
| 26 | 25 | 24 |
| 27 | 27 | 27 |
| 28 | 28 | 29 |
| 29 | 30 | 28 |
| 30 | 29 | 30 |
| 31 | 31 | 31 |
| 32 | 32 | 32 |
| 33 | 33 | 33 |
| 34 | 34 | 34 |
| 35 | 35 | 35 |
| 36 | 36 | 36 |
| 37 | 37 | 38 |
| 38 | 38 | 37 |
| 39 | 39 | 42 |
| 40 | 40 | 41 |
| 41 | 41 | 40 |
| 42 | 42 | 39 |
| 43 | 44 | 43 |
| 44 | 43 | 44 |
| 45 | 45 | 46 |
| 46 | 46 | 45 |
| 47 | 47 | 47 |
| 48 | 49 | 48 |
| 49 | 48 | 49 |
| 50 | 50 | 50 |
| 51 | 51 | 52 |
| 52 | 53 | 51 |

FIG. 7K-2

| | | |
|---|---|---|
| 53 | 52 | 54 |
| 54 | 54 | 53 |
| 55 | 57 | 55 |
| 56 | 55 | 56 |
| 57 | 56 | 57 |
| 58 | 58 | 58 |
| 59 | 60 | 59 |
| 60 | 61 | 61 |
| 61 | 59 | 60 |
| 62 | 62 | 63 |
| 63 | 63 | 62 |
| 64 | 64 | 64 |
| 65 | 65 | 67 |
| 66 | 67 | 66 |
| 67 | 66 | 65 |
| 68 | 68 | 68 |
| 69 | 69 | 69 |
| 70 | 71 | 70 |
| 71 | 70 | 71 |
| 72 | 72 | 73 |
| 73 | 73 | 72 |
| 74 | 74 | 74 |
| 75 | 76 | 75 |
| 76 | 75 | 76 |
| 77 | 77 | 77 |
| 78 | 78 | 78 |
| 79 | 79 | 79 |
| 80 | 80 | 80 |
| 81 | 82 | 82 |
| 82 | 81 | 81 |
| 83 | 84 | 83 |
| 84 | 83 | 84 |

FIG. 7K-3

NON_CANCER Deutan (genetic error)

| | | |
|---|---|---|
| age | 28 | |
| Error score | 76 | 84 |
| Mean error | 2.8941176 | 2.9882353 |
| SQRT of erro | 8.7177979 | 9.1651514 |
| B+Y SQRT | 6.5574385 | 6.7082039 |
| R+G SQRT | 6.5574385 | 6.4807407 |
| Quad. axis | 0 | 0.2274632 |
| BINOCULARLY NORMAL | | |
| On eye to eye comparison | | |
| 0.697353503 | | |
| | | |
| Box 1 SQRT | 4.472136 | 4.472136 |
| Box 2 SQRT | 3.162278 | 5.291503 |
| Box 3 SQRT | 5.09902 | 4.690416 |
| Box 4 SQRT | 4.472136 | 3.741657 |
| | | |
| Amp. sine | 0.4786083 | 0.2175608 |
| | | |
| C.M.A. | 14.200328 | 16.147651 |
| | 56.696849 | 58.644172 |
| dev. +/- | 1.5935408 | 4.6205501 |
| | | |
| beta | 0.1653728 | 0.0728058 |
| M.S.E. | 0.5403417 | 0.9387077 |
| S.E.(A) | 0.112756 | 0.1486178 |

FIG. 7K-4

LEGEND

Calculations are based upon published normative methods for analysis of the Fransworth-Munsell 100 Hue Color Test (using cap 85).

DOT = Date Of color vision Test
Error Score = Total Cap Error
Mean Error = Mean of Error Score
SQRT of Error = √ of Error Score
B+Y SQRT = √ of the Cap Score Consisting of the Blue & Yellow Caps
R+G SQRT = √ of the Cap Score Consisting of the Red & Green Caps
Quadrant Axis = Derives from B+Y SQRT and R+G SQRT Box 1 SQRT = √ of Box 1 Cap Scores
Box 2 SQRT = √ of Box 2 Cap Scores
Box 3 SQRT = √ of Box 3 Cap Scores
Box 4 SQRT = √ of Box 4 Cap Scores Amp. Sine = Amplitude of Sine Wave
C.M.A. = Color of Major Axis
Dev. ± = S.D. ±

β = Modulation of Sine Wave
M.S.E = Mean Standard Error
S.E.(A) = Standard Error (A), where (A) is Amplitude of the Sine Wave

FIG. 7L

MATERIALS AND METHODS FOR DETECTION OR MONITORING OF NEOPLASTIC DISEASE

This application claims priority from application Ser. No. 60/084,417, filed May 6, 1998.

BACKGROUND OF THE INVENTION

Cancer is one of the leading causes of death and disability in the United States. Each year, over 1 million new cases of cancer are diagnosed. Despite the seriousness of the disease, many people survive cancer, with the chances of success often being directly related to whether the cancer is detected at an early stage. For decades researchers have attempted to identify and understand physiological events associated with cancer. Through an improved understanding of cancer and its causes it may be possible to identify better methods for detection, prevention, and treatment.

Cancer can attack almost any portion of the body and often has far-reaching effects within the body of an afflicted individual. When a patient gets cancer many systems in the body undergo changes. These changes may be due to organ failure as the tumor grows to take over the organ(s). Other changes may be due to the increased metabolic rate of the tumor, cell death in or around the tumor, or even due to compounds secreted by the tumor. These various changes in response to tumor growth are known as the pathophysiology of cancer.

Specific examples of physiological changes associated with cancer include the visually devastating retina degenerations, cancer associated retinopathy (CAR) and melanoma associated retinopathy (MAR). Fortunately these severe retinopathies are quite rare (estimated one/100,000 cancer patients). As their names imply, these pathologies are associated with the retina. The retina is the portion of the visual system at the back of the eye responsible for collecting the visual stimuli (light). The light is then converted into impulses decoded by the brain and perceived as vision. The retina is composed of many cell types, with each cell type having a specific function. Cells in the retina are responsible for light detection, signal processing, signal transmission, structural and nutritive functions. The light detection portion is composed of cells known as photoreceptors. Two photoreceptor cell types are present in the primate retina, rods and cones. The rods are responsible for our ability to detect low levels of light, such as the ability to see at night. Among the cones are three types, red, green, and blue. These three types of cones are responsible for the color vision experienced by humans. Fine visual acuity that is present in primates (humans included) occurs due to the cellular composition of a region of the retina, called the macula. Light detection and the ability to see details occur in the macula and are due to cone function. Macular vision uses predominantly cones of the red and green types.

Each type of cone cell contains a different set of light activated pigment proteins. Each pigment type responds to light of a different color. The cone cells also have other biochemical and protein features that make each cone type unique. In the blue cones, one protein is of particular interest—Carbonic Anhydrase (CA).

Rare but serious visual losses have been reported which occur as paraneoplastic retinopathies associated with carcinoma of the lung (Jordan, B. L., W. W. Dawson, T. Fang [1998] *Invest Opthalmol Vis Sci.* 39:s402) and less often with cervix, colon, prostate and breast cancers (Dawson, W., B. Jordan, K. Hazariwala, T. Fang, R. Marsh, presented in Prague, Czech Republic at annual ISCEV meeting, spring 1998). Cancer associated retinopathy (CAR) is characterized by rapid onset, progressive acuity loss and mild-to-moderate fundus changes. A related and even more rare retinopathy has been associated with malignant melanoma of the skin (MAR) (Posner, J. B., J. Dalmau [1995] *Clin Neurol Neurosurg.* 97:61–70; Alarcon-Segovia, D., A. Ruiz-Arguelles, L. Llorente [1996] *Immunology Today* 17:163–164). MAR is typified by sudden onset of night "blindness", bizarre visual image alterations and "moving" lights. Circulating factors and autoimmune responses at various retinal sites have been implicated in both diseases (Darnell, R. B. [1996] *Proc. Natl. Acad. Sci USA* 93:45294536; Korngruth, S. E. [1989] *N Eng J Med* 321, 23:1607–1608). Patients seldom seek speciality eye care before there is a significant change in central vision, such as in CAR or MAR.

Although a growing number of anticancer agents have been identified, the treatment of cancer is still fraught with difficulties and uncertainties. Effective detection and treatment of cancer is particularly challenging because of the many different types of cancer and the associated complexities involved in accurately identifying the presence of a particular form of cancer, and then identifying and applying the proper treatment regimen.

In recent years, a growing number of diagnostic methods have been devised for identifying the presence of cancer. Many of these diagnostic methods are based upon immunological characteristics such as antigen and/or antibody recognition procedures. These procedures are often labor intensive, difficult to interpret or quantify, require a blood sample, and are so specific that only certain forms of cancer are detected. Therefore, a need exists for new methods for identifying those at risk for cancer and/or those in the early stages of cancer. Also, accurate and simple methods for monitoring the progression of cancer are needed.

BRIEF SUMMARY OF THE INVENTION

The subject invention concerns the identification of retinal dysfunctions associated with neoplastic disease. The retinal dysfunctions are observed in patients who have undergone treatment for cancer as well as those who have not undergone treatment. Thus, according to the subject invention it has been determined that physiological responses associated with cancer are manifested as early detectable changes in the retina. In a preferred embodiment, the subject invention pertains to non-invasive tests whereby the existence of certain retinal dysfunctions indicate the presence and/or status of neoplastic disease.

The diagnostic methods of the subject invention involve the identification of an acquired retinal dysfunction in individuals with cancer. The retinal dysfunctions which are the basis of the diagnostic test of the subject invention can be detected as described herein despite the fact that best corrected visual acuity is seldom reduced or abnormal. The methods of the subject invention can be used to identify patients having any of a variety of cancers including, but not limited to, breast, colon, lung, skin, and testicular cancer. Retinal deficits have been found in patients prior to chemotherapy and, advantageously, the test of the subject invention facilitates very early diagnosis of cancer.

The clinical condition detected according to the methods described herein has been termed Cancer Associated Retinal Deficit (CARD). CARD is very different from, and should not be confused with, cancer and melanoma associated retinopathy (CAR and MAR, respectively). CARD does not involve the common clinically detected causes of visual loss (cataracts, glaucoma, macular degeneration, etc.). Also, the functional changes in CARD patients do not appear to be due to chemotherapy, since there is no visible ophthalmologic retinal damage, it exists prior to chemotherapy, and is present in many patients who have received different treatment regimens.

In a particularly preferred embodiment, the presence of cancer is identified based on dysfunctions in color vision, dark adaptation, ERG, and/or EEG. These results can be augmented with results from, for example, a dilated eye examination which can rule out other sources of vision dysfunction.

Results of tests utilizing the methods of the subject invention indicate that a very high proportion of cancer patients have CARD. The majority of these changes are proving to be undetectable in a routine clinical eye exam.

Prior to the current invention, individuals with CARD syndrome were often dismissed (by the ophthalmologist and/or other physician) and told that the vision problems are functional or age related. Proper identification of CARD according to the subject invention is an important diagnostic procedure which can be used to improve quality of patient life and improve cancer survival statistics.

BRIEF SUMMARY OF THE FIGURES

FIGS. 7A through 7L show color vision results as error cap designations of the Farnsworth-Munsell 100 Hue color test for 26 patients. Patients 1 through 25 are cancer patients. Patient 26 is a genetic deutan.

DETAILED DISCLOSURE OF THE INVENTION

Figure 1:
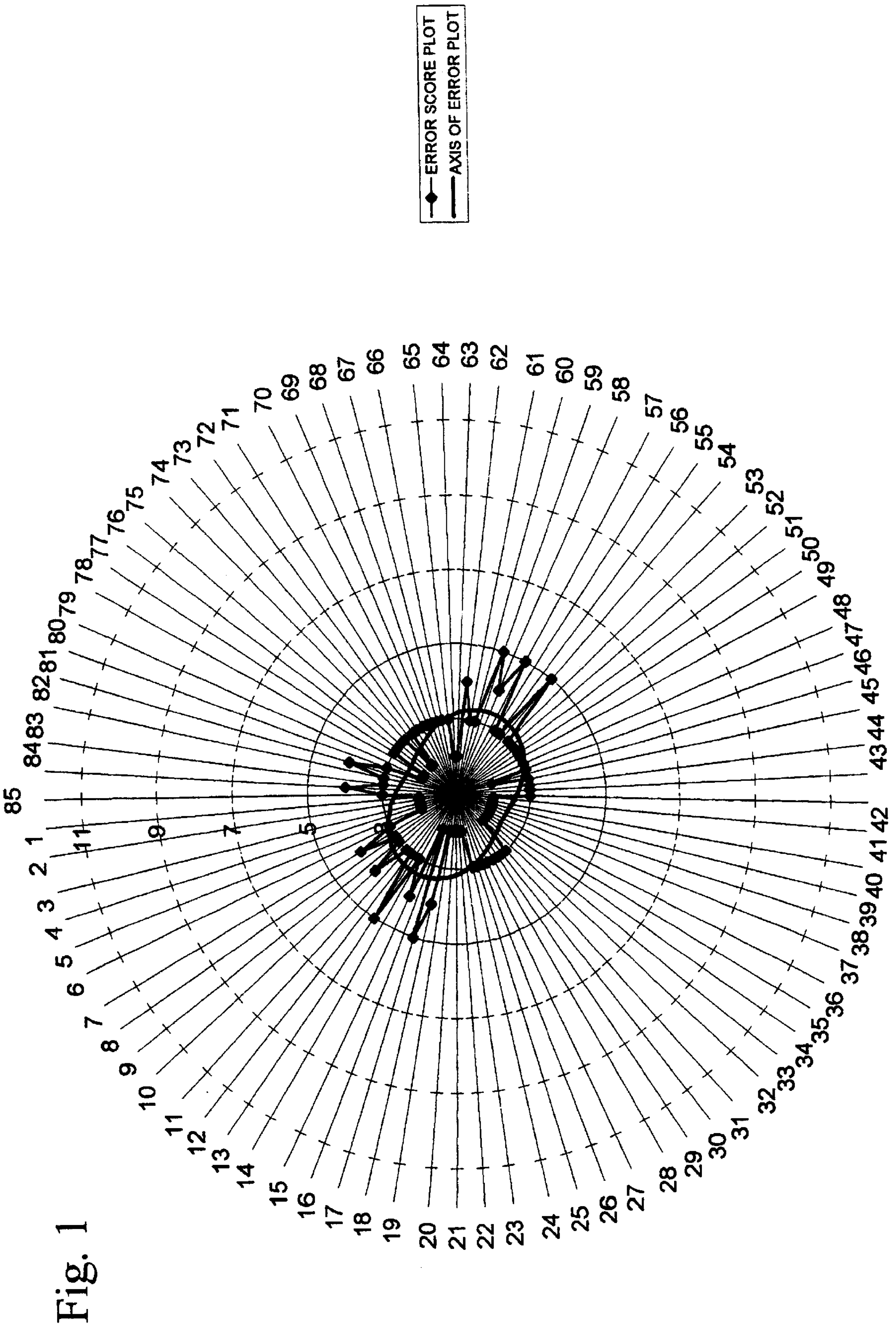
FIG. 1 shows a standard modified circular plot of a Farnsworth-Munsell 100 Hue color test errors for an aberrant color vision for one eye (right) of a genetic deutan patient. Genetic deutan as determined by ISHIHARA color plates (which exhibit a hypersensitivity to the red/green inherited color vision errors). The error score of the right eye is 76 which is not grossly abnormal, yet the patient has a color vision defect. The axis of error plot demonstrates an axis to the errors as shown in the color of major axis (CMA information) 14.2; 56.7 with S.D.=∓1.6.

The subject invention provides materials and methods for the identification of individuals who have Cancer Associated Retinal Deficit (CARD). CARD syndrome is a clinical entity differing in both its etiology and severity of disease from CAR and MAR, and can be used according to the subject invention in the diagnosis, monitoring, and treatment of cancer.

Patients with CARD can be identified as described herein by ophthalmologic examination tests, and/or by an interview or questionnaire as described herein. Advantageously, these methods are non-invasive and can be used to detect cancer at an early stage. For individuals tested by standard ophthalmologic examinations, cancer patients are not expected to have the retinal deficits described here. However, when testing for the deficits that set CARD aside from other visual abnormalities, a high proportion of cancer patients will have the retinal deficits described here. Even using an interview/questionnaire format as described herein, approximately more than half of cancer patients can be identified.

The assays of the subject invention can be used to detect cancer at a very early stage thus enhancing the likelihood of effective treatment of the cancer. In a specific embodiment, melanoma is one cancer for which retina dysfunction symptoms as described herein are clearly present at an early stage. Thus, these visual deficits are present prior to the time when cancer is detected using standard methods of cancer diagnosis.

The tests used to identify CARD can also be useful in following patients treated for cancer, such as with chemotherapeutic regimens. In excess amounts chemotherapy is known to cause retinal degenerations. The side effects of some chemotherapy regimens are peripheral neuropathies. However, these degenerations are different from CARD. Thus the ability to follow neurological function through a series of tests provide new methods of following and preventing the peripheral neuropathies.

The retina is one of the most biochemically active, complex, and sensitive organs of the body and the retina cell types are responsible for the results seen in CARD patients. The retina processes signals from the photoreceptors through a series of cells. Malfunctions can be detected or appear as a blue cone defect. Among the cell types that can be damaged are the bipolar cells, horizontal cells, neurons, Muller, or ganglion cells. Involvement of these cell types is by immunological means (antibodies or T-cells), or by other toxic factors associated with cancer cells. As used herein, "toxic factor" refers to a blood-borne agent which causes the retinal deficits described herein. Thus, in a specific embodiment of the subject invention, tests are developed to indicate the presence of these toxic factor(s).

The retina involvement with cancer provides a linkage between retinal response and progression of the disease. Observation of changes during the course of the disease makes it possible to follow tumor progression. Testing according to the subject invention can be done for new cancer patients to establish a baseline value. From this baseline value, effects of treatment/disease progression can be followed. The testing for CARD can also be used for determining visual disability levels of cancer patients.

The tests utilized according to the subject invention identify retinal deficits which are otherwise genetically rare, or only associated with other diseases of the eye. CARD diagnosis can be accomplished according to the subject invention utilizing all or a subset of the following: 1) a questionnaire which can be administered, for example, during a verbal interview; 2) administration of the Farnsworth-Munsell 100 Hue color test (and analysis of the specific color vision trend/abnormality); 3) testing for dark adaptation (night vision); 4) standard dilated eye examination to verify the absence of biological causes of visual disability including, for example, glaucoma, cataract, diabetic retinopthy, genetic retinal degeneration, macular degeneration, or other disease known to affect the retina; 5) electroretinogram (ERG) to determine the electrical functioning of the retina; and 6) electroencephalograms (EEG) for comparisons with ERG data to establish a non-invasive methodology to screen for cancer, progression/remission of cancer, or side effect of chemotherapy. In preferred embodiments, the methods of the subject invention involve evaluation of color vision, night vision parameters, and/or electrical measurements of neuronal function.

The visual changes in CARD, are not attributable to treatment modalities, and do not change the visual acuity of the patient. These changes have proved to be undetectable in the course of a routine clinical eye exam, and thus have missed diagnosis.

Of the 25 cancer patients that have been fully tested, all 25 patients have one or more visual deficits associated with the symptoms of CARD. The symptoms of CARD can include rare tritan color vision errors (CV), binocular color vision abnormality (which is a significant difference between the color scores for both eyes), abnormal night vision—dark adaptation (DA), and reduction in some portions of the ERG signals, without a significant loss of visual acuity. The deficits found in CARD are distinct and do not involve the common causes of visual loss (cataracts, glaucoma, optic nerve disease, age-related macular degeneration, etc.).

Color vision losses were primarily determined to be tritanoptic (blue-yellow color axis) and though rare, are most frequently seen secondary to other diseases. A few patients also exhibit tetartanopia, a complete loss of color discrimination. These defects are known as acquired dyschromatopsias, and are distinct from inherited color defects. The tritan defect is carried as a non-sex-linked gene in 1/13,000 otherwise normal humans. Due to its rarity no statistics exist for tetartanopia. Among partially tested patients: sample female patients (2/24) have been found with a statistically significant ($P<0.05$) tritan defect, while another (4/24) show clear trends toward a tritan abnormality (one of which has not received any treatment beyond surgery), and (1/24) appears to be a tetartan; sample male patients (4/22) have been found with a statistically significant ($P<0.05$) tritan defect, while others (4/22) show clear trends towards the tritan abnormality (one of which has not received any treatment beyond surgery), and (1/22) appears to be a tetartan. Nearly 33% (15/46) of these sample patients have a tritan or tetartan dyschromatopsias. In one male patient, the tritan dyschromatopsias is localized in one eye, the fellow eye has normal color sensitivity. These findings are consistent with pathophysiology of the highly sensitive blue cone receptor system. The loss of blue cones is from outside the macula and, thus, does not affect visual acuity. These color vision losses could also be due to loss of retina cells responsible for higher order processing.

When sample patients visit an eye specialist with visual complaints, visual acuity tests normally. Retinal findings show a perfectly normal fundus (in most patients). Using the Ishihara color plates and the Farnsworth 100-Hue color vision test, the common sex-linked protan or deutan (red/green) color vision defects have not been found.

Compromised night vision is clinically known as nyctalopia or "night-blindness." Normal persons have two photoreceptor types known as rods and cones. In adapting to the dark, the cone system is responsible for the first approximately 2-log units (100×) of light sensitivity which occurs over the first 5 to 10 minutes of being in the dark. There is then a markedly detectable shift to the rod system function. Full dark adaptation occurs over the next 20+minutes. The rod system is responsible for the final 3–4 log units (1000× to 10,000×) of light sensitivity. In the majority of patients (20/25), this cone rod shift is delayed or incomplete. The result is a loss of 0.5 to 2.5 log units (up to 400×) of final dark adapted sensitivity. The responses found in the later portions of dark adaptation are most likely due to a death/modification of the rod photoreceptor cells.

The DA responses are complex. In all but one patient the cone response is modified, this also suggests a problem with the cone system (or higher order processing). In more than 70% of the patients the DA final threshold is elevated. This suggests a problem with a different area of the visual system—the rods (or the higher level processing involved in the signal transmission). The ERG responses are primarily limited to the reduction of the oscillatory potentials.

On the other side of the light/dark adaptation equation, some patients find moderate illumination uncomfortable (photophobia). This is particularly true of those who have or had melanoma. Many of these same patients also have nyctalopia. This is a further indication that these patients have a problem in their rod photoreceptor system.

While the retina is the most easily accessible portion of the complex neurological system, the brain may provide a myriad of responses in relation to cancer. The ERG reductions show the presence of modifications in the retina of the electrical response characteristics of healthy nervous tissue. The EEG measures electrical changes in the brain and thus also changes in the brain related to cancer at sites remote to the brain. In a specific embodiment of the invention, EEG can detect cancer related to CARD. CARD patient EEG's can be performed on patients with ERG changes and compared with norm data groups. All of this information provides a better picture of the total effect of cancer on the neurological system.

The ERG measures the electrical function of the retina. More than 76% of the patients have ERG defects with most defects of the same type. Traditional interpretation of the ERG results would have suggested a different functional deficit from that suggested by the cone and rod photoreceptor results. The genetic rod and cone degenerative diseases have characteristic ERG patterns. The ERG oscillatory potentials (OPs), it is commonly believed show that a problem exists with the upper layers of the retina (layers away from the photoreceptors). This type of reduction in OPs has been proposed as being due to ischemia in some cases. Whether the observed changes in ERG are due to ischemia, damage to neural tissue, or some other mechanism has not been definitively determined; however, these changes are associated with cancer and thus can be used according to the subject invention to detect cancer as described herein. These changes in OPs indicate that we may very well see a similar functional change in the brain waves of these patients. Brain waves are measured as EEG. Thus, a non-invasive methodology to screen for cancer, progression/remission of cancer, or side effect of chemotherapy would be to measure an equivalent wave form of the EEG.

Visual dysfunctions of this frequency, more than 50% color vision effects, over 90% with dark adaptation defects, and over 70% eyes having ERG defects have not been previously documented. The identification of color vision defects at the trend to tritan level can be improved by advanced testing using anomaloscopic testing and Quadrant analysis of Farnsworth-Munsell 100 Hue tests. Of particular relevance in the diagnosis of CARD are errors in Box 3 of the Farnsworth-Munsell test. Also of interest are errors in Boxes 1, 2 and 4. Color defective sample patient retinal findings are perfectly normal—as could be expected, if these subjects were carrying the dominantly inherited genetic tritan trait. Dark adaptation data from sample patients resembles a genetic disease—Congenital Stationary Night Blindness (CSNB), except for the ERG component which is only moderately changed. The drastic ERG changes seen in CSNB are not seen in these patients. Pedigrees with CSNB or tritan defects have one defect or the other, not both. In contrast, both a tritan and dark adaptation defect exist in 40% of the CARD subject patients, in some cases, monocularly.

The dysfunctions found in this patient sample are different and distinct from those found in CAR and MAR patients. The retina of CAR and MAR patients typically provide some clinical evidence (to an eye specialist) of retinal or fundus damage. Some reported cases of both CAR and MAR have other underlying health problems (diabetes, glaucoma, retinal tears, age related macular degeneration, etc.) which are documented to effect changes in the visual system. The sample patients who have CARD typically do not exhibit the signs of retinal disease. In addition, the color vision defects found in CARD are not detectable by use of the standard Ishihara color plates, as used for CAR and MAR.

Chemotherapy has been known to cause visual problems in some cases. Loss of visual acuity with vincristine, presence of cotton wool spots in patients with systemic disease and interferon treatment, cataracts, macular edema, and isolated retinal crystals in patients on Tamoxifen. None of these responses are present in this cohort of cancer patients. None of the melanoma patients treated with interferon had cotton wool spots, none of the vincristine treated patients were overdosed with the loss of visual acuity, only one patient had Tamoxifen, without the listed effects on vision. Yet, it is possible that some current chemotherapy regimens act synergistically with the biological processes occurring that produce CARD. In a specific embodiment of this invention, patients can be monitored throughout their diagnostic, treatment and recovery process. Treatments can be tailored to protect and reduce neural pathophysiology. The development of a process to follow, or protect the patient from neural pathophysiology will thus aid in treatment regimens by allowing the use of a more cytotoxic drug, or increased dosage, in some treatments that formerly would have lead to neural toxicity and patient suffering.

Various psychophysical tests can be used according to the subject invention to identify CARD. For example, such as Benham's disk can also be used for testing of the patient population. Test series with Benham's disks can identify differences between normal patients and CARD patients, showing which retinal cells are affected. Other tests which can be used to achieve a differentiation between normals (non-cancer) and cancer patients) include color ERG. Other evaluation of the eye can be done including, but not limited to, nerve conduction speeds along the optic nerve, changes in refractive error due to cancer (accommodation), changes in pupil diameters (light sensitivity), and contrast sensitivity.

CARD patients who have completed the fill series of ophthalmologic tests show photoreceptor abnormalities in both color vision and the ability to see light in the dark—Dark Adaptation (DA). The color abnormalities are primarily due to a defective response that involves the blue cones. This shows that this portion is due to the light and color responsiveness of the cone system, while another is due to the interaction of rod and cone response, the final is due to light sensitivity of the rods alone. Most CARD patients have an abnormality of cone system sensitivity in response to DA. Tests for the ability to see fine details (visual acuity), show no abnormalities in the function of the cone cells in the macula. Thus, the primary effects of CARD are not on the red and green cones. The final result is not classified by color conventions as a Deutan or Protan deficient.

Visual dysfunctions of the type and frequency found among these cancer patients (over 50% color vision defects, over 90% with major dark adaptation defects, and over 70% of patients having ERG defects) have not been previously reported.

With the benefit of the descriptions provided herein, those skilled in the art can identify toxic factor(s) associated with the retinal deficits responsible for CARD. Cell specific autoimmune responses are shown by western blot or on cryosections of human donor retinal tissue. The protein(s) involved can then be identified. This is accomplished by, for example, using CARD patient serum to screen a human cDNA retina protein expression library. Patch clamp technology can be used to produce a cell specific cDNA protein expression library, and thus limit results only to the cell types shown to be damaged or missing from histological studies. With an identified protein, the fate of cells in both tumors and the retina can be monitored. This provides: (a) the ability to screen for current or past presence of a tumor growth, and (b) a mechanism for stimulation of the immune system to produce a different yet even more effective anti-tumor response, while sparing the fine portions of vision affected in the current situation with CARD patients.

Examination of tumor secretions for a cell specific cytotoxic compound(s) can be done in several ways. Live tumor cells obtained from patients early during treatment can be grown in tissue culture and the conditioned culture media thus used to grow embryonic mammalian retina. Sera from CARD patients can be examined for protein profiles and undergo an examination for abnormal protein profiles. Abnormal profiles can be used for growth tests of a retina in conditioned culture media.

The autoantibody responses among fully tested cancer patients comprise a broad spectrum of immune reactivites (at one/400 serum dilution): 22 kDa, 24 kDa, 26 kDa, 28 kDa, 30 kDa, 34 kDa, 37 kDa, 44 kDa, 46 kDa, 67 kDa, and 80 kDa proteins.

Testing cancer patient serum (by western blot) shows that all but one patient has an autoimmune response toward a human retinal protein of 30 kDa. On these blot strips this protein is at the location of human retinal CA. Since blue cones have CA, all patients (except 1) have detectable levels of anti-30 kDa antibodies. The results seen in these patients may be due to the immune response acting on this cell type (blue cones) of the retina, or due to an immune response after blue cone damage by another agent.

What is visualized on western blots as the presence of immune reactivity toward the retinal 30 kDa protein (presumed to be CA), may be due to a phenomenon known as cross-reactivity. In cross-reactivity a different protein elicits an immune response, due to protein similarities. These similarities may be evident in common sequences or in epitope conformation. Thus antibodies to the initial protein then recognize and "cross-react" with another different or similar protein. An epitope is part of a protein sequence, contiguous or noncontiguous. Usually these are noncontiguous, and are represented by a 3-Dimensional shape that is recognizable by the 3-Dimensional binding site within the antibody. If, the immune system is responsible for the symptoms seen in CARD patients, it may be possible to test for this by using sections of tissue. The techniques for performing this type of testing are called immunohistochemistry. It has been determined in accordance with the subject invention that 40% of CARD patients have antiretinal antibodies that bind to specific neural cells such as the retina, glial or Muller cells, rods, cones, or any combination thereof. Since cone cells are implicated for some CARD symptoms it would be expected for serum to stain the blue cone cells, or their associated cells responsible for signal transmission.

The deficits of function in the cone system in these CARD patients may be due to the anti-30 kDa antibody action on the retinal cells containing CA, the blue cones. It could also be due to antibodies against another blue cone specific protein, such as the blue cone pigment protein. This autoimmune response could have been induced by any number of proteins, since many cancer types are involved. Yet, the retinal CA has only a limited number of potential epitopes. These epitopes or the expression of antibodies to them could then be the common link for cancers. Tests for such epitope specific reactivity could easily be prepared.

The involvement of the immune system may also be used as a marker of retinal degeneration, with patients showing retinal defects in many cases having antiretinal antibodies, generated as an effect of the cancer causing retinal cell death. Thus, autoimmune responses as measured by CARD patient serum antibody binding to a substrate, cells-tissue, proteins, and epitopes can be used to follow the progression/presence of cancer.

Following are examples which illustrate procedures for practicing the invention. These examples should not be construed as limiting.

EXAMPLE 1

Ouestionnaire

A questionnaire can be used to obtain information regarding color vision and night vision dysfunction. An example of such a questionnaire is provided in Appendix I. Evidence of color and/or night vision dysfunction obtained from the questionnaire, combined with the absence of ocular disease accounting for the dysfunction, is indicative, according to the subject invention, of the presence of cancer.

EXAMPLE 2

Evaluation

Figure 2:
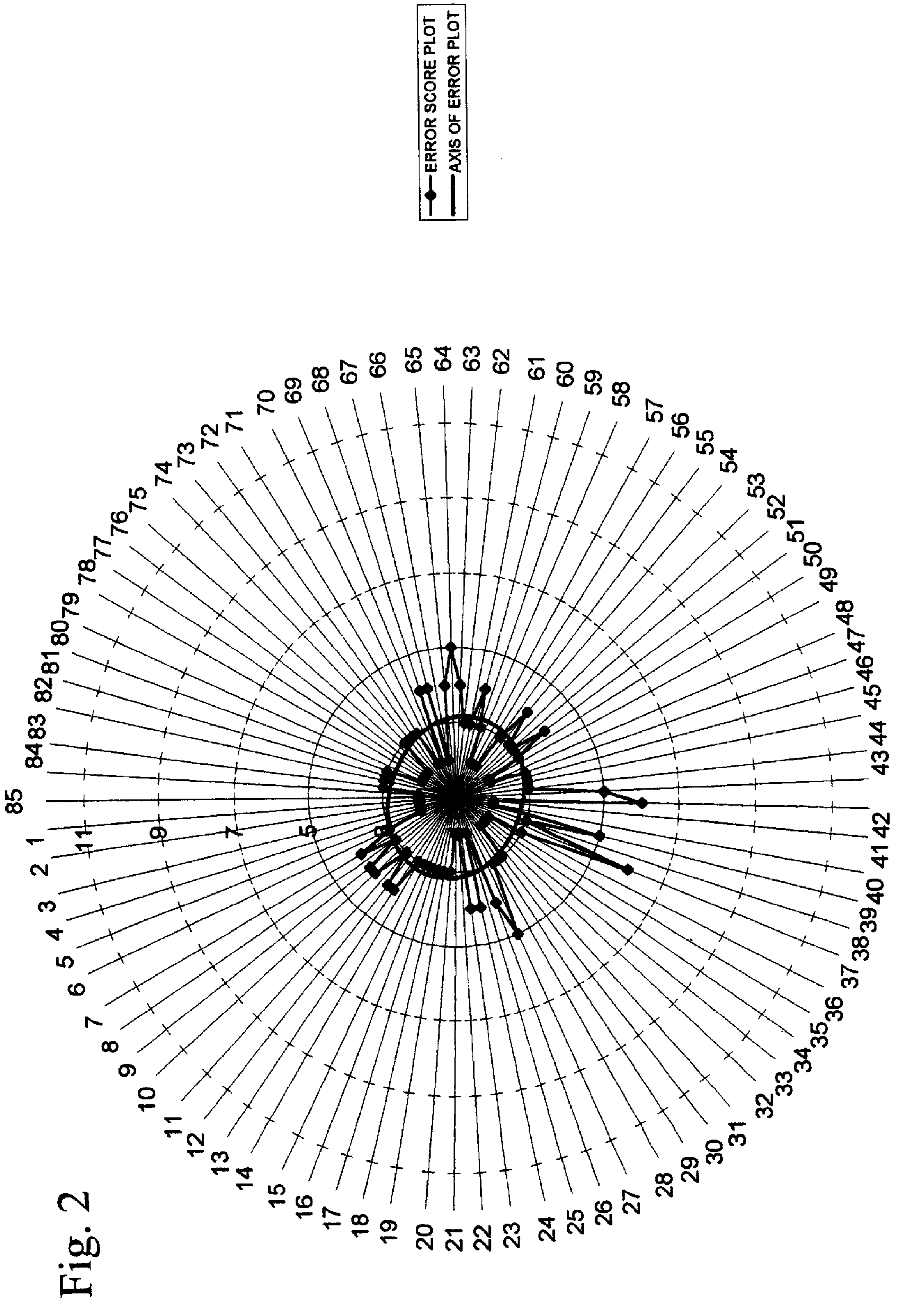
FIG. 2 shows a standard modified circular plot of a Farnsworth-Munsell 100 Hue color test errors for an aberrant color vision for one eye (left) of a genetic deutan patient. Genetic deutan as determined by ISHIHARA color plates (which exhibit a hypersensitivity to the red/green inherited color vision errors). The error score of the left eye is 84 which is not grossly abnormal, yet the patient has a color vision defect. The axis of error plot demonstrates an axis to the errors as shown in the color of major axis (CMA information) 16.1; 58.6 with S.D.=∓4.6.

Patients can be interviewed and a vision-biased questionnaire is administered. Ishihara's color plates and the Farnsworth-Munsell 100 hue color test can be administered. The Ishihara color plates can be used to, for example, rule out common genetic vision defects. Color vision is well characterized with respect to published norm data groups and analysis (Verriest, G. J. Van Laethem, A. Uvijls [1982] *Am. J. Ophthalmol.* 93:635–642; Smith, V. C., J. Pokorny, A. S. Pass [1985] *Am J. Ophthalmol.* 100:176–182; Knoblauch, K. [1987] *Invest Ophthalmol Vis Sci.* 28:707–710; Lugo, M., J. S. Tiedeman [1986] *Am J. Ophthalmol.* 101:469–474; Atchison, D. A., K. J. Bowman, A. J. Vingrys [1991] *Optom Vis Sci* 68:41–48; Bowman, K. J. [1982] *Acta Ophthalmol Copenh.* 60:907–916). Those skilled in the art are familiar with color vision plots which would show standard color vision errors along the red/green color axis. See, for example, FIGS. 1, 2, and patient #26 data in FIG. 7. These are the common sex-linked protan and deutan errors seen in about 7% of the European descended male population.

A retinal examination and/or interview can be conducted to identify any environmental exposure that would lead to retinal damage (Bhargava, S. K., C. I. Phillips, P. A. Aspinall [1973] *Acta Ophthalmol Copenh.* 51:829–840; Mergler, D., G. Huel, R. Bowler, B. Frenette, J. Cone [1991] *Arch Environ Health* 46:326–334; Gobba, F., C. Galassi, M. Imbriani, S. Ghittori, S. Candela, A. Cavalleri [1991] *J Occup Med.* 33:761–765; Dias, P. L. [1990] *Br J Addict.* 85:241–244; Mantyjarvi, M. I., K. Nerdrum, K. Tuppurainen [1992] *J. Clin. Neuroophthalmol.* 12:98–103; Bronte, Stewart J., W. S. Foulds [1972] *Mod Probl Ophthalmol.* 11:168–173; Lakhanpal, V., S. S. Schocket, R. Jiji [1984] *Ophthalmology* 91:443–451). Serum samples can be obtained from the patient during the initial patient enrollment and at subsequent visits. These serum samples can be used for autoimmune testing. Humoral (antibody) responses can be tested against human retinal proteins by western blot, or immunohistochemistry.

Patients can be seen at a later date by an ophthalmologist who develops a medical history, and performs an extensive eye examination, including but not limited to intraocular pressure, visual acuity, refraction, dilated fundus exam, lens and corneal examination. This phase of clinical testing is useful to rule out other physical causes of visual changes. Humphry automated visual field or Goldmann visual field tests are done to check for changes in peripheral vision.

The patient can be given an ERG and/or EEG evaluation. Dark adaptation can be assessed using a Goldmann/Weekers Dark adaptometer (Haag-Streitt, Ag. Bern) for central and/or peripheral retina. The DA is well characterized with respect to known genetic diseases (Miyake, Y., K. Yagasaki, M. Horiguchi, Y. Kawase, T. Kanda [1986] *Arch Ophthalmol.* 104:1013–1020; Fishman, G. A., P. Pulluru, K. R. Alexander, D. J. Derlacki, L. D. Gilbert [1994] *Am J. Ophthalmol.* 118:362–367; Fishman, G. A., K. R. Alexander, A. H. Milam, D. J. Derlacki [1996] *Ophthalmology* 103–96–104), drug modifications (Mavrikakis, M., S. Papazoglou, P. P. Sfikakis et al. [1996] *Ann Rheum Dis.* 55:187–189; Decensi, A., R. Torrisi, A. Polizzi et al. [1994] *J. Natl. Cancer Inst.* 86:105–110; Gottlob, I., K. Strenn, B. Schneider [1994] *Graefes Arch Clin Exp Ophthalmol.* 232:584–588; Weleber, R. G., S. T. Denman, J. M. Hanifin, W. J. Cunningham [1986] *Arch Ophthalmol* 104:831–837), and to the phasic parameters involved in the analysis of DA (Herse, P. [1995] *Optom Vis. Sci.* 72:907–910). The DA is multiphasic (cone response, cone-rod shift—a shift to rod function, a bi-phasic rod response, and final threshold).

EXAMPLE 3

Detection of CARD 110 randomly selected patients with various cancers have given informed consent (25 have completed all phases of testing). Initial testing involved Ishihara plates, near visual acuity, and questions about visual symptoms. Each sample patient first underwent a thorough interview to determine if any idiosyncratic vision problems existed. Patients which informed of ophthalmologic disease/damage, or cancer (to brain) which might confound test results were not enrolled.

Further testing consisted of: an ophthalmologic exam, Humphries or Goldmann visual fields, Farnsworth-Munsell 100-hue color test, Goldmann/Weekers (central and peripheral) dark adaptation test, fundus photos, Heidelberg laser scanning tomography, and measurements of electrical function of neural tissue. Serum samples were drawn for autoantibody testing on western blots of normal donor human retinal tissue extracts, for AntiNuclear Antibody (ANA), and for western blots with purified proteins. The Farnsworth-Munsell 100-Hue color test was analyzed by computer program, quadrant analysis, or other CV testing/analysis scheme.

The summarized data are as follows; average age—52 (27 to 69); 13 male, 12 female; all white; cancer types—testicular, melanoma, kidney (2 types), lung (3 types) breast (4 types), colon, bladder, Ewing sarcoma, and ovarian; most patients have had treatment; color vision defects=11 tritan or trend to tritan, 2 tetartan, 4 binocular color abnormality; ERG defects consisted of photopic, macular 4, oscillatory potential, and scotopic defects; elevation in dark adaptation thresholds in 30 eyes; only one eye had a visual acuity of 20/40, all other eyes had better visual acuity; only 9 eyes had age-related changes in the macular region; 1 patient had an inferior nasal visual field defect; 4 patients had detectable antinuclear antibody (ANA) titer—none above 1/40; all but 1 patient (No. 7, Table 1) had antiretinal antibodies (ARA) detectable at a titer of 1/400 on western blot of human retinal proteins; 50% of the patients had IgG antibodies to the human retinal form of glyceraldehyde 6 phosphate dehydrogenase; only 4 patients had IgM antibodies to enolase, while 4 had weak IgG and 10 had strong IgG responses against enolase.

The results of this study are presented in Tables 1 to 3, and in FIG. 7. FIG. 7 is a spreadsheet showing the color vision data collected for CARD patients. Table 2 summarizes the data obtained for patients with melanoma. Table 1 summarizes the data obtained for all patients except those with breast cancer. Some of the patients in Table 2 are also shown in Table 1. Table 3 summarizes the data obtained for patients with breast cancer.

Figure 3:
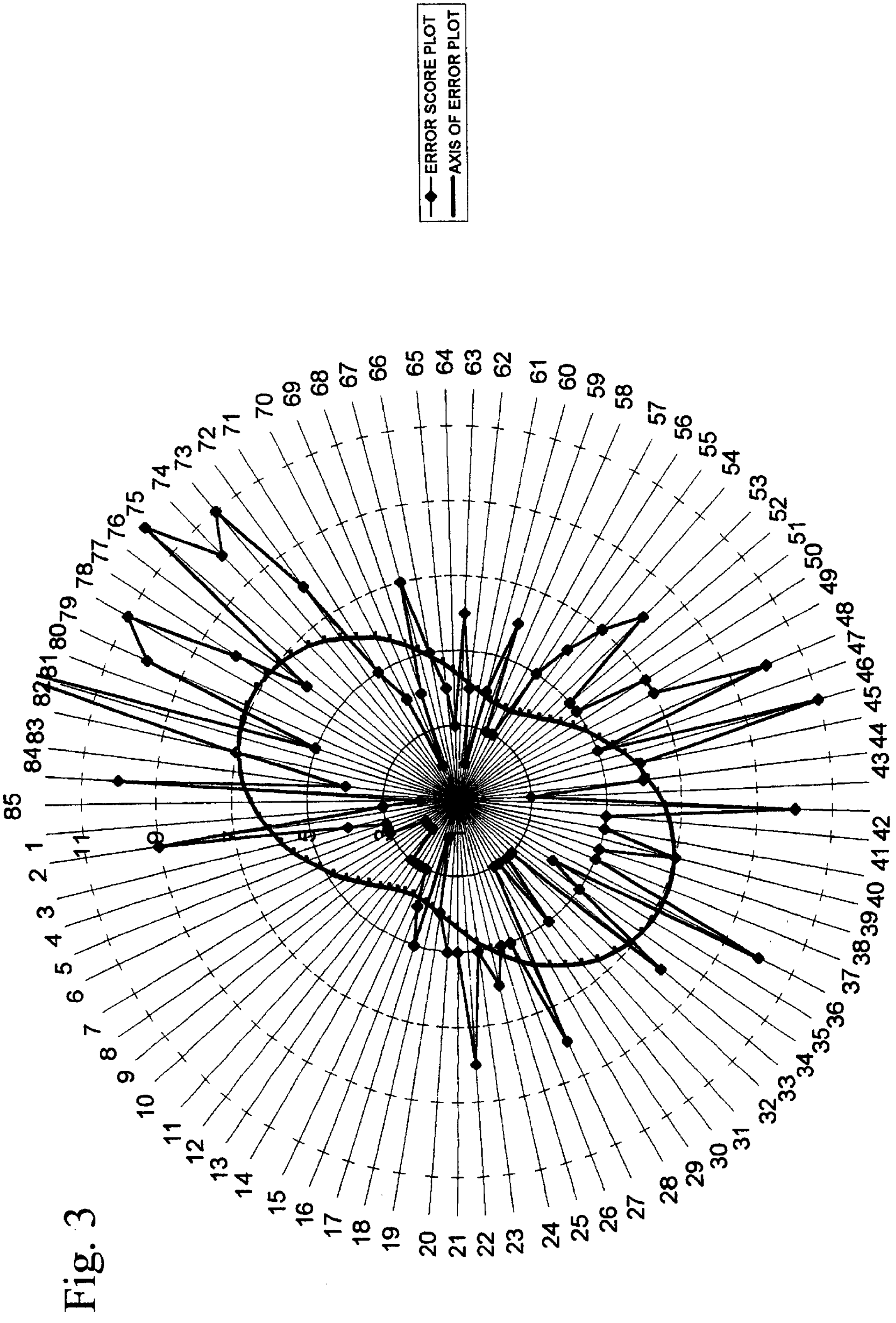
FIG. 3 shows a standard modified circular plot of a Farnsworth-Munsell 100 Hue color test errors for an aberrant color vision for one eye (right) of a patient with melanoma of the skin. The error score exceeds the critical value for age and sex. The patient has color vision abnormality. The axis of this Figure differs from that of the patient's other eye as illustrated in FIG. 4. The error score plot of the right eye total error score of 292 is grossly abnormal. The axis of error plot demonstrates an axis to the errors as shown in the color of major axis (CMA information) 78.8; 36.3 with S.D.=∓1.6.
Figure 4:
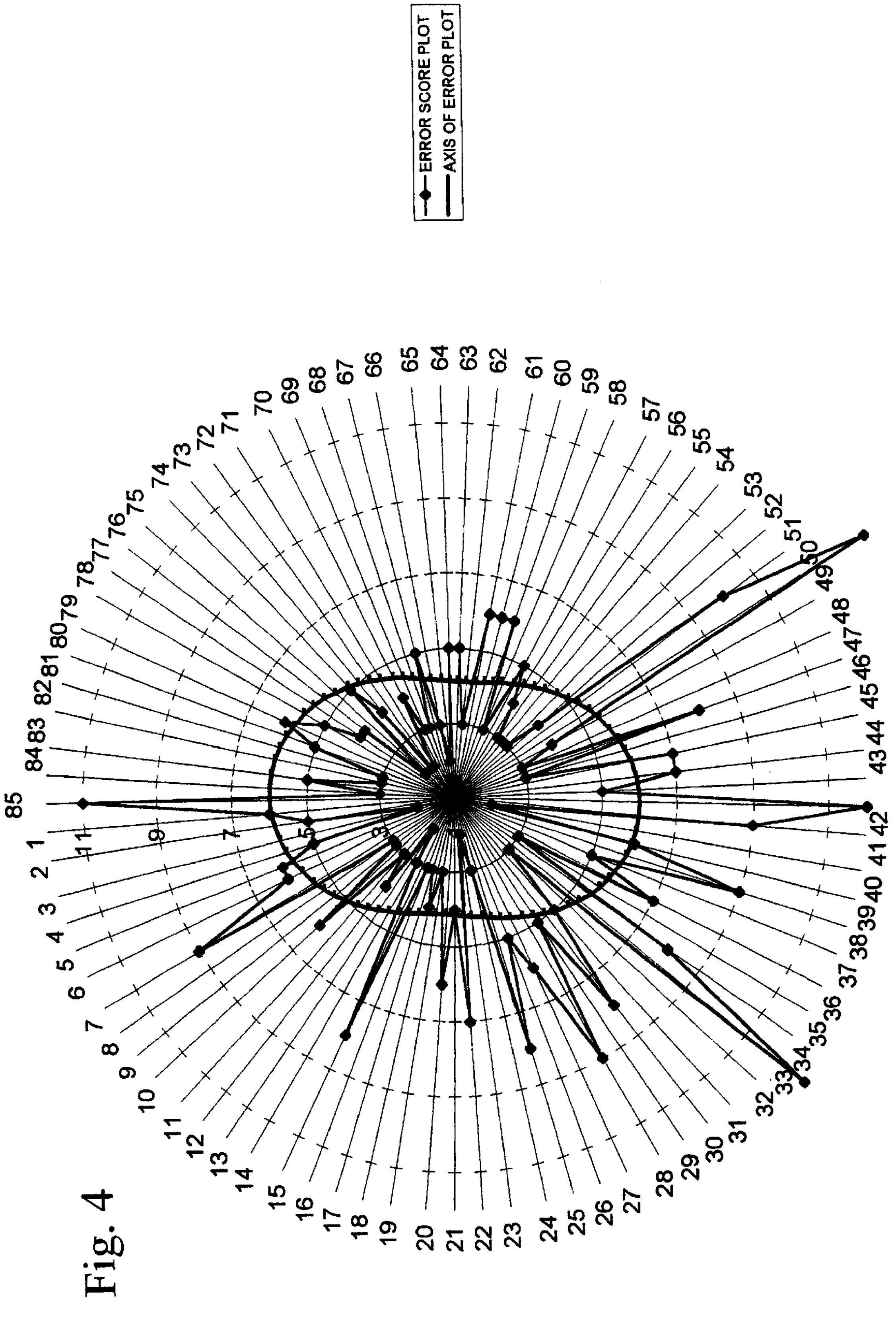
FIG. 4 shows a standard modified circular plot of a Farnsworth-Munsell 100 Hue color test errors for an aberrant color vision for one eye (left) of a patient with melanoma of the skin. The error score exceeds the critical value for age and sex. The patient has color vision abnormality. The axis of this Figure differs from that of the patient's other eye as illustrated in FIG. 3. The error score plot of the right eye total error score of 260 is grossly abnormal. The axis of error plot demonstrates an axis to the errors as shown in the color of major axis (CMA information ) 84.1; 41.6 with S.D.=∓2.8.
Figure 5:
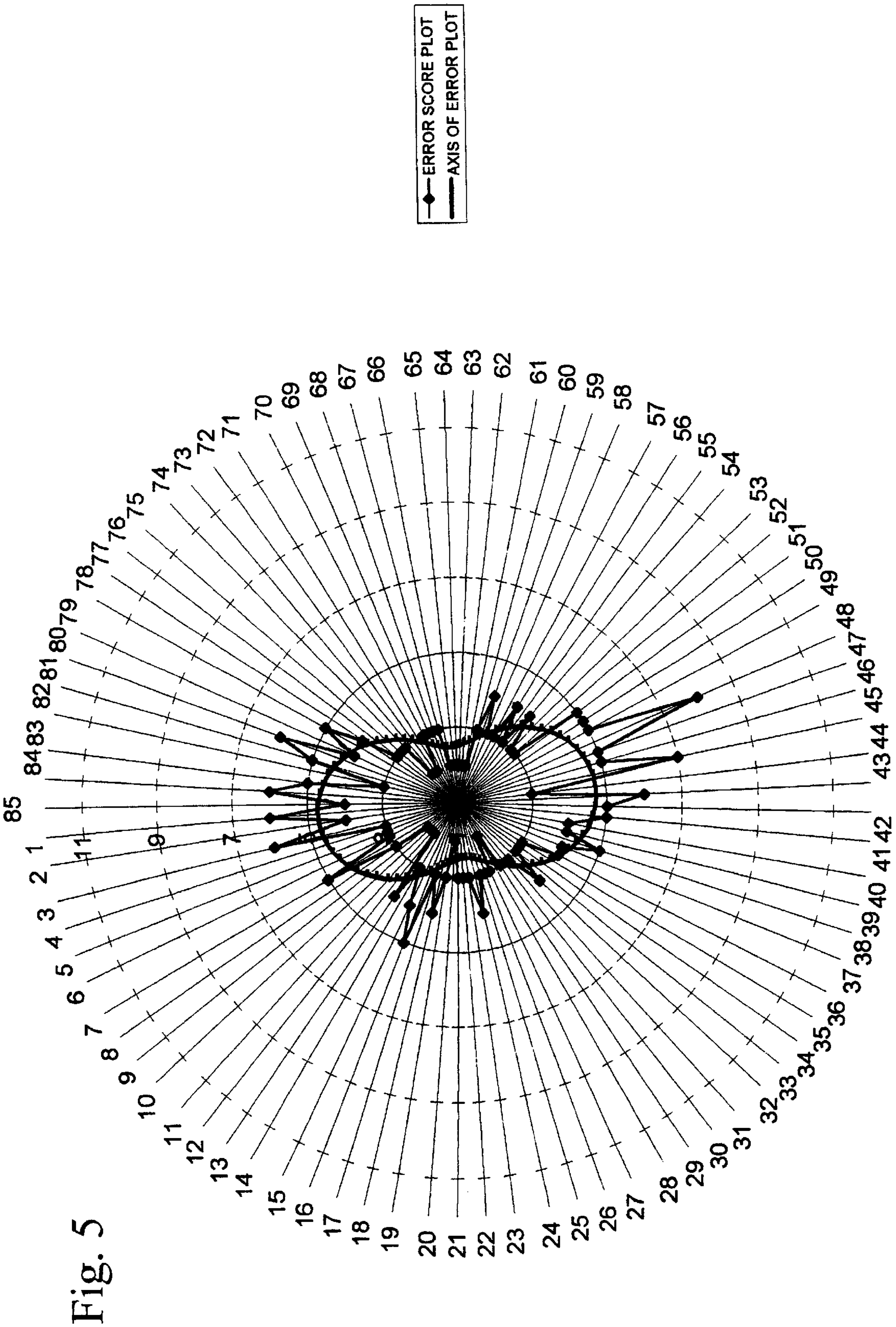
FIG. 5 shows a standard modified circular plot of a Farnsworth-Munsell 100 Hue color test errors for an aberrant color vision for one eye (right) of a patient with renal cancer. Error score does not exceed critical value for P value of error, yet a very clear axis is found in both this Figure and the patient's other eye as illustrated in FIG. 6. The error score of the right eye is 136 which is not grossly abnormal, yet the patient has a color vision defect. The axis of error plot demonstrates an axis to the errors as shown in the color of major axis (CMA information) 1.3; 43.8 with S.D.=∓9.
Figure 6:
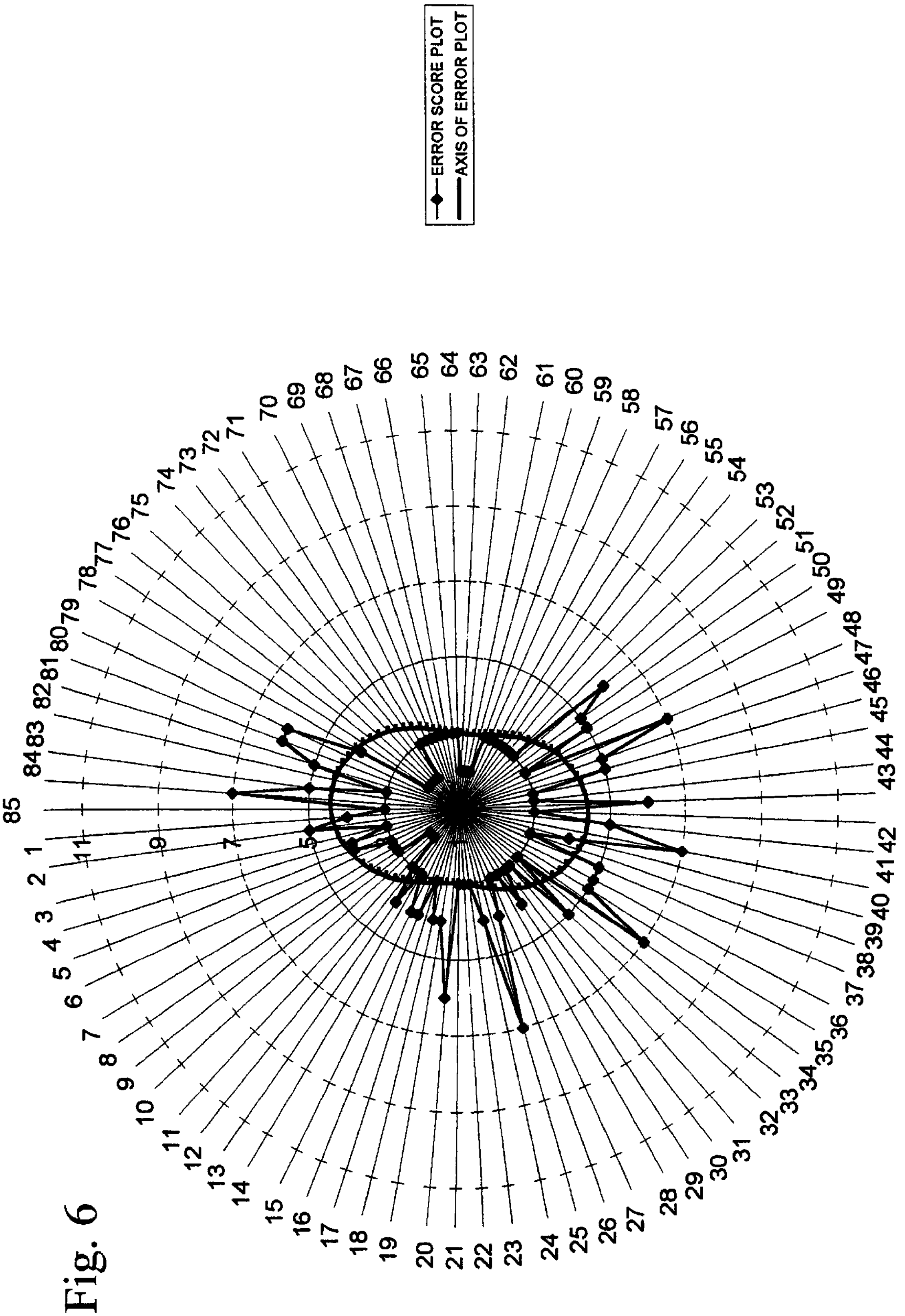
FIG. 6 shows a standard modified circular plot of a Farnsworth-Munsell 100 Hue color test errors for an aberrant color vision for one eye (left) of a patient with renal cancer. Error score does not exceed critical value for P value of error, yet a very clear axis is found in both this Figure and the patient's other eye as illustrated in FIG. 5. The error score of the left eye is 144 which is not grossly abnormal, yet the patient has a color vision defect. The axis of error plot demonstrates an axis to the errors as shown in the color of major axis (CMA information) 83.8; 41.3 with S.D.=∓1.8.

From this study, the following conclusions can be drawn:

1. 100% of patients in the sample had at least 1 identifiable visual deficit, over 95% had 2 or more identifiable visual deficits.
2. No patients with CAR or MAR were found. Instead based upon the widespread indications of visual deficits in these cancer patients we propose a third clinical visual syndrome associated with cancer: Cancer Associated Retinal Deficit (CARD).
3. Patients with CARD exhibit no apparent loss of best corrected visual acuity.
4. Rare color vision deficits are associated with patients who have CARD.
5. In contrast to CAR and MAR the ERG may be only moderately effected in CARD.
6. Rather than random errors in color vision, specific axes are apparent in CARD patients. The aberrant axis may be the same or different in each eye. FIGS. 3 to 6 show examples of color vision plots for CARD patients. These plots show aberrant axes, as illustrated in FIGS. 3 and 4, from a patient with melanoma.

EXAMPLE 4

Diagnosis of Melanoma

See Melanoma Patient Data Chart (PDC) (Table 2) for abnormalities among 10 melanoma patients. The abnormalities are highlighted by heavy lined boxes.

Color vision: Two often sample patients tested for CV with melanoma, had statistically significant CV defects consisting of a tritan defect ((OD−p<0.02), (OS−p<0.01)) in one eye while the other eye was tetartan ((OS−p<0.05), (OD−p<0.001)), respectively. Five of the ten have a tritanomoly or a tritan trend. In a tritanomoly the error score is not high enough to trigger an aberrant reading by p value, yet the direction of the color axis exceeds what could be expected for random error. Thus, eight out of ten melanoma patients tested for CV exhibits an abnormality in their color vision. Of these eight with CV errors two have not received any treatment. The aberrant tritan color vision for PDC melanoma patient #5 in Table 2 is illustrated in FIGS. 3 and 4.

Dark Adaptation: Patients with dark adaptation defects can display more than one type of abnormality. Elevation of final thresholds is the most common method for reporting DA. In patients with melanoma five of eight have an elevated final threshold value of 0.5 log to 1.0 log (>2 SD) above the norm mean. The cone response is abnormal in eight of the eight melanoma patients. One of these eight patients has not received any treatment.

Electroretinogram: Three out of the seven patients tested for ERG have an abnormal ERG. The common defect is a reduction in the oscillatory potential. This occurs in patients with and without interferon treatment.

From analysis of the questionnaire responses, as many as 60% of the volunteers complained of non-diagnosed visual changes, which were not attributable to treatment modalities, and apparently did not change the visual acuity of the patient.

EXAMPLE 5

Test Kits

A test kit can be designed to facilitate practice of the method of the subject invention. One such kit could include, for example, 1) a vision questionnaire portion, 2) color test materials, these may be, for example, specific color tests—utilizing a software, hardware, and/or printed version of pseudo-isochromatic plates such that the errors detected by this series detects those color vision errors present in CARD as shown in, for example, CARD patients in Tables 1–3 (these errors are in contrast to patient #26 of FIG. 7, and FIGS. 1 and 2, age 28, who is a genetic Deutan, and sees none of the standard Ishihara plates). In a specific embodiment, portions of the Farnsworth Munsell 100 hue test (as the results of this study indicate) are provided. Also, color matching can be performed with an anomaloscope (or its soft or hardware embodiment), 3) dark adaptation test materials, and 4) materials for testing and/or interpreting electrical/physiological functioning of components of the neural system as changed in CARD patients. Preferably, the kit would comprise two or more of the components listed above.

Should results indicate that the person needs further testing, then a referral to a qualified eye specialist could be done.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 1

SAMPLE FROM 110 CANCER PATIENT VOLUNTEERS (EXCEPT BREAST CANCER)

| | | | | | | | | | | | COLOR VISION | | | | | ELECTRORETINOGRAM | | | | | | | | |
|---|---|---|---|---|---|---|---|---|---|---|---|---|---|---|---|---|---|---|---|---|---|---|---|---|
| | | | | | | | | | | | | | | | | PHOTO-TOPIC (ms) | | | | | | | | |
| No | AGE | SEX | RACE | CANCER | DATE DIAG | TDT | MET | TREAT-MENT | SMOK-ER | EYE | SCORE | CMA | P | ERROR | ISHHARA | ¼ HZ | 30 HZ | MAC 4° | O.P. | DARK B | DARK ADAPTA-TION Threshold Elevation above norm mean (0.5 = +2 S.D) | BEST CORREC-TED VISU-AL ACCUI-TY | DFE | VISUAL FIELD |
| 1 | 50 | M | W | CLASS IIB SEMINOMA | 3/94 | N | Y | CIS PEB | QUIT 1983 | R | 200 | 1–43 | (P < .05) | TRITAN | 11/11 | 135(27) | 75(27) | 2.27 | 2060 | 570(60) | 0.5 log | 20/20 | NOR | HVF FULL |
| | | | | | | | | | | L | 116 | 4–46 | | | 11/11 | 175(27) | 105(26) | 1.60 | 3289 | 745(135) | 0.5 log | 20/20 | NOR | HVF FULL |
| 2 | 27 | M | W | MELANOMA | 1992 | N | Y | INT | ? | R | 108 | 2–47 | (P < .02) | TRITAN | 11/11 | 120(27) | 57(26) | 3.0 | 1700 | 570(27) | | 20/20 | NOR | HVF FULL |
| | | | | | | | | | | L | 104 | 37–79 | (P < .05) | TETARTAN | 11/11 | 140(27) | 68(25) | 3.3 | 1894 | 810(41) | | 20/25 | NOR | HVF FULL |
| 3 | 55 | M | W | BLADDER | 1996 | Y | Y | R MVAC | NO | R | 188 | 42–84 | (P < .05) | TRITAN | 11/11 | 89(30) | 59(26) | 1.9 | 1289 | 444(33) | 0.7 log | 20/15 NEAR | NOR | FTCF |
| | | | | | | | | | | L | 124 | 4–46 | | | 11/11 | 93(29) | 66(26) | 2.9 | 1036 | 384(45) | 0.5 log | 20/15 NEAR | NOR | FTCF |
| 4 | 55 | M | W | NON-SMALL CELL LUNG | 1/97 | Y | N | RC, CAR, T | 25YRS | R | 56 | 35–77 | | | 11/11 | 110(28) | 73(28) | 5.2 | 1441 | 546(125) | 0.5 log | 20/25 | RPEΔ | GVF FULL |
| | | | | | | | | | | L | 48 | 9–51 | | | 11/11 | 106(28) | 64(27) | 4.8 | 1188 | 566(130) | | 20/20 | NOR | GVF FULL |
| 5 | 63 | M | W | SQUAMOUS CELL LUNG | 1994 | Y | Y | TAXT CIS | 24YRS | R | 56 | 6–48 | | | 11/11 | 130(30) | 129(32) | 2.1 | 1747 | 520(51) | 1.2 log | 20/20 | NOR | HVF FULL |
| | | | | | | | | | | L | 72 | 1–43 | | | 11/11 | 90(30) | 81(31) | 2.2 | 850 | 420(38) | 1 log | 20/25 | NOR | HVF FULL |
| 6 | 46 | M | W | MELANOMA | 4/95 | N | Y | SUR | YES | R | 104 | 29–71 | | | 11/11 | 95 | 39(26) | 2.4 | 1290 | 325 | 1 log | 20/25 | DRS | GVF FULL |
| | | | | | | | | | | L | 96 | 1–43 | | | 9/11(7.2) | 65 | 33(26) | 0.54 | 780 | 296 | 1 log | 20/25 | NOR | GVF CON |
| 7 | 36 | M | W | LEVEL IV MELANOMA | 9/93 | N | Y | INT | 4 YRS | R | 64 | 31–73 | | | 9/11(45.2) | 96(27) | 66(25) | 3.4 | 1492 | 520(90) | 0.5 log | 20/40 | NOR | BAD TEST |
| | | | | | | | | | | L | 68 | 7–49 | TRITANOMOLY | | 9/11(45.2) | 106(27) | 68(27) | 3.9 | 1492 | 620(87) | 0.5 log | 20/30 | NOR | HVF FULL |
| 8 | 51 | M | W | RENAL | 1/96 | Y | Y | INT CRET | ? | R | 132 | 2–44 | TRITANOMOLY | | 11/11 | 95(27) | 57(26) | 1.6 | 1651 | 370(59) | 0.5 log | 20/20 | NOR | HVF FULL |
| | | | | | | | | | | L | 144 | 41–83 | TRITANOMOLY | | 11/11 | 85(26) | 55(26) | 1.2 | 1230 | 345(55) | 0.5 log | 20/20 | NOR | HVF FULL |
| 9 | 49 | M | W | EWING SARCOMA | 8/97 | Y | N | V, CYCL, DOX | YES | R | 52 | 41–83 | | | 11/11 | 75(26) | 53 | 3.1 | 1295 | 255N | 0.5 log | 20/20 | RPEΔ | GVF FULL |
| | | | | | | | | | | L | 40 | 39–81 | | | 11/11 | 90(27) | 55 | 2.5 | 1450 | 321N | 0.5 log | 20/20 | NOR | GVF FULL |
| 10 | 66 | M | W | MELANOMA | 7/97 | N | ? | INT | ? | R | 48 | 42–84 | | | 11/11 | 141 | 84 | 3.3 | 2300 | 780(70) | 1 log | 20/20 | NOR | HVF FULL |
| | | | | | | | | | | L | 56 | 41–83 | | | 11/11 | 131 | 84 | 2.0 | 1900 | 840(95) | | 20/20+ | NOR | HVF FULL |

TABLE 1-continued

SAMPLE FROM 110 CANCER PATIENT VOLUNTEERS (EXCEPT BREAST CANCER)

| | | | | | | | | | | | | | | | | | | | | | | | | |
|---|---|---|---|---|---|---|---|---|---|---|---|---|---|---|---|---|---|---|---|---|---|---|---|---|
| 11 | 66 | M | W | MELANOMA | 1994 10/97 | N | Y | INT | ? | R | 296 | 37–79 | (P < .001 | TETARTAN | 11/11 | 105 | 79 | 4.3 | 1091 | 474 | 0.5 log | 20/25 | NOR | GVF FULL |
| | | | | | | | | | | L | 260 | 42–84 | (P < .01) | TRITAN | 11/11 | 105 | 66 | 2.0 | 829 | 405 | 0.5 log | 20/30 | NOR | GVF FULL |
| 12 | 39 | M | W | MELANOMA | 9/95 | N | Y | INT | YES | R | 112 | 4–46 | TRITANOMOLY | | 11/11 | 203 | 155 | 5.0 | 2507 | 502 | | 20/15 | DRS | GVF FULL |
| | | | | | | | | | | L | 72 | 37–79 | | | 11/11 | 171 | 129 | 4.3 | 1925 | 502 | | 20/15 | NOR | GVF FULL |
| 13 | 66 | F | W | STAGE II OVARIAN | 4/97 | N | Y | CIS, T | NO | R | 28 | 1–43 | | | 11/11 | 120 | 73 | 5.4 | 1207 | 562 | | 20/20 | NOR | HVF FULL |
| | | | | | | | | | | L | 20 | 41–83 | | | 11/11 | 120 | 75 | 5.8 | 1007 | 585 | | 20/20 | NOR | HVF FULL |
| 14 | 66 | F | B | LUNG | 5/95 | Y | Y | NAV | NO | R | 256 | 37–79 | (P < .05) | TRITAN | 11/11 | | | | | | 0.5 log | 20/20 | NV | FTCF |
| | | | | | | | | | | L | 184 | 41–83 | TRITANOMOLY | | 11/11 | | | | | | 0.5 log | 20/20 | NV | FTCF |
| 15 | 42 | M | W | MELANOMA | 1995 | N | Y | INT | 20YRS | R | 100 | 33–75 | | | 11/11 | 180 | 141 | 5.8 | 2596 | 588 | | 20/20 | NOR | FTCF |
| | | | | | | | | | | L | 116 | 28–70 | TRITANOMOLY | | 11/11 | 190 | 107 | 4.5 | 2000 | 560 | | 20/20 | NOR | FTCF |
| ABBERANT | | | | VALUES | | | | | | | | | | | | 78 | 53 | 1.9 | 1500 | 280 | | | | |

DATE DIAG = DATE OF DIAGNOSIS;
TREATMENT: CIS = CISPLATIN;
INT = INTERFERON;
R = RADIATION;
MVAC = METHOTREXATE, VINCRISTINE, ARRIAMIYCIN, CYTOXIN;
C = CYTOXIN;
CAR = CARBOPLATIN;
T = TAXOL;
TAXT = TAXOTERE;
CYCL = CYCLOPHAMIDE;
DOX = DOXORUBICIN;
NAV = NAVELBINE;
SUR = SURGERY ONLY;
TDT = UNDERGOING TREATMENT DATE(S) OF TESTING;
COLOR VISION: COLOR OF MAJOR AXIS = CMA;
ERG: ELECTRORETINOGRAM (MICROVOWS P-P);
MAC 4° = MACULAR 4°;
O.P. = OSCILLITORY POTENTIAL (RMS MICROVOLTS × $10^2$;
DARK B = SCOTOPIC B WAVE;
DARK ADAPTATION: PERFORMED ON GOLDMANN//WEEKERS ADAPTOMETER (HAAG-STREIT);
DFE = DILATED FUNDUS EXAM: RPEΔ = MILD RETINAL PIGMENTED EPITHELIAL CHANGES;
NOR = NORMAL;
DRS = DRUSEN;
NV = NARROWING OF VESSELS;
VISUAL FIELD: HVF = HUMPHRY VISUAL FIELD;
GVF = GOLDMANN-VISUAL FIELD;
CF = FULL TO CONFRONTATION;
CON = CONSTRICTED VISUAL FIELD

TABLE 2

MELANOMA PATIENT DATA CHART - 10 MELANOMA PATIENTS (7 FULLY TESTED, 3 IN TESTING)

| No | AGE | SEX | RACE | CANCER | DATE DIAG | TDT | MET | TREAT-MENT | SMOK-ER | EYE | COLOR VISION SCORE | CMA | P | ERROR | ISHHARA | ELECTRORETINOGRAM PHOTO-TOPIC (ms) ¼ HZ | 30 HZ | MAC 4° | O.P. | DARK B | DARK ADAPTA-TION Threshold Elevation above norm mean (0.5 = +2 S.D) | BEST CORREC-TED VISU-AL ACCUI-TY | DFE | VISUAL FIELD |
|---|---|---|---|---|---|---|---|---|---|---|---|---|---|---|---|---|---|---|---|---|---|---|---|---|
| 1 | 27 | M | W | MELANOMA | 1992 | N | Y | INT | ? | R | 108 | 2–47 | (P < .02) | TRITAN | 11/11 | 120(27) | 57(26) | 3.0 | 1700 | 570(27) | | 20/20 | NOR | HVF FULL |
| | | | | | | | | | | L | 104 | 37–79 | (P < .05) | TETARTAN | 11/11 | 140(27) | 68(25) | 3.3 | 1894 | 810(41) | | 20/25 | NOR | HVF FULL |
| 2 | 46 | M | W | MELANOMA | 4/95 | N | Y | SUR | YES | R | 104 | 29–71 | | | 11/11 | 95 | 39(26) | 2.4 | 1290 | 325 | 1 log | 20/25 | DRS | GVF FULL |
| | | | | | | | | | | L | 96 | 1–43 | | | 9/11(7,2) | 65 | 33(26) | 0.54 | 780 | 296 | 1 log | 20/25 | NOR | GVF CON |
| 3 | 36 | M | W | LEVEL IV | 9/93 | N | Y | INT | 4YRS | R | 64 | 31–73 | | | 9/11(45,2) | 96(27) | 66(25) | 3.4 | 1492 | 520(90) | 0.5 log | 20/40 | NOR | BAD TEST |
| | | | | MELANOMA | | | | | | L | 68 | 7–49 | | TRITANOMOLY | 9/11(45,2) | 106(27) | 68(27) | 3.9 | 1492 | 620(87) | 0.5 log | 20/30 | NOR | HVF FULL |
| 4 | 66 | M | W | MELANOMA | 7/97 | N | ? | INT | ? | R | 48 | 42–98 | | | 11/11 | 141 | 84 | 3.3 | 2300 | 780(70) | 1 log | 20/20 | NOR | HVF FULL |
| | | | | | | | | | | L | 56 | 41–83 | | | 11/11 | 131 | 84 | 2.0 | 1900 | 840(95) | | 20/20+ | NOR | HVF FULL |
| 5 | 66 | M | W | MELANOMA | 1994 | N | Y | INT | ? | R | 296 | 37–79 | (P < .001) | TETARTAN | 11/11 | 105 | 79 | 4.3 | 1091 | 474 | 0.5 log | 20/25 | NOR | GVF FULL |
| | | | | | 10/97 | | | | | L | 260 | 42–84 | (P < .01) | TRITAN | 11/11 | 105 | 66 | 2.0 | 829 | 405 | 0.5 log | 20/30 | NOR | GVF FULL |
| 6 | 39 | M | W | MELANOMA | 9/95 | N | Y | INT | YES | R | 112 | 4–46 | | TRITANOMOLY | 11/11 | 203 | 155 | 5.0 | 2507 | 502 | | 20/15 | DRS | GVF FULL |
| | | | | | | | | | | L | 72 | 37–79 | | | 11/11 | 171 | 129 | 4.3 | 1925 | 502 | | 20/15 | NOR | GVF FULL |
| 7 | 42 | M | W | MELANOMA | 1995 | N | Y | INT | 20 YRS | R | 100 | 33–75 | | | 11/11 | 180 | 141 | 5.8 | 2569 | 588 | | 20/20 | NOR | FTCF |
| | | | | | | | | | | L | 116 | 28–70 | | TRITANOMOLY | 11/11 | 190 | 107 | 4.5 | 2000 | 560 | | 20/20 | NOR | FTCF |
| 8 | 47 | M | W | MELANOMA | 1/97 | N | Y | NONE | 7 YRS | R | 128 | 33–75 | | TRITANOMOLY | 11/11 | ND | ND | ND | ND | ND | ND | 20/30 | ND | FTCF |
| | | | | | | | | | | L | 108 | 7–49 | | TRITANOMOLY | 11/11 | ND | ND | ND | ND | ND | ND | 20/30 | ND | FTCF |
| 9 | 41 | F | W | MELANOMA | 1/98 | N | ? | NONE | NO | R | 84 | 33–75 | | TRITANOMOLY | 11/11 | ND | ND | ND | ND | ND | ND | 20/20 | ND | FTCF |
| | | | | | | | | | | L | 100 | 32–74 | | TRITANOMOLY | 11/11 | ND | ND | ND | ND | ND | ND | 20/20 | ND | FTCF |
| 10 | 46 | F | W | MELANOMA | 97 | N | Y | SOME | 20YRS | R | 124 | 9–51 | | TRITANOMOLY | 9/11(5,16) | ND | ND | ND | ND | ND | 0.5 log | 20/25 | ND | HVF FULL |
| | | | | | | | | INT | | L | 140 | 39–81 | | TRITANOMOLY | 9/11(5,16) | ND | ND | ND | ND | ND | 0.5 log | 20/20 | ND | HVF FULL |
| ABBERANT | | | | VALUES | | | | | | | ERG: NORM 33 EYES AGES 9–59 (>2.0 S.D.) | | | | | 78 | 53 | 1.9 | 1500 | 280 | | | | |

TABLE 2-continued

| MELANOMA PATIENT DATA CHART - 10 MELANOMA PATIENTS (7 FULLY TESTED, 3 IN TESTING) |
| --- |

DATE DIAG = DATE OF DIAGNOSIS;
TREATMENT: INT = INTERFERON;
SUR = SURGERY ONLY;
TDT = UNDERGOING TREATMENT DATE(S) OF TESTING;
COLOR VISION: COLOR OF MAJOR AXIS = CMA;
ERG: ELECTRORETINOGRAM (MICROVOLDS P-P);
MAC 4° = MACULAR 4°;
O.P. = OSCILLITORY POTENTIAL (RMS MICROVOLTS $\times 10^{-2}$;
DARK B = SCOTOPIC B WAVE;
DARK ADAPTATION: PERFORMED ON GOLDMANN//WEEKERS ADAPTOMETER (HAAG-STREIT);
DFE = DILATED FUNDUS EXAM: RPEΔ = MILD RETINAL PIGMENTED EPITHELIAL CHANGES;
NOR = NORMAL;
DRS = DRUSEN;
NV = NARROWING OF VESSELS:
VISVAL FIELD: HVF = HUMPHRY VISUAL FIELD;
GVF = GOLDMANN-VISUAL FIELD;
FTCF = FULL TO CONFRONTATION:
CON = CONSTRICTED VISUAL FIELD

TABLE 3

SAMPLE FROM BREAST CANCER PATIENT VOLUNTEERS

| No | AGE | SEX | RACE | CANCER | DATE DIAG | TDT | MET | TREAT-MENT | SMOK-ER | EYE | COLOR VISION SCORE | COLOR VISION CMA | COLOR VISION P | COLOR VISION ERROR | ISHHARA | ELECTRORETINOGRAM PHOTO-TOPIC (ms) ¼ HZ | ELECTRORETINOGRAM PHOTO-TOPIC (ms) 30 HZ | ELECTRORETINOGRAM MAC 4° | ELECTRORETINOGRAM O.P. | ELECTRORETINOGRAM DARK B | DARK ADAPTA-TION Threshold Elevation above norm mean (0.5 = +2 S.D) | BEST CORREC-TED VISU-AL ACCUI-TY | DFE | VISUAL FIELD |
|---|---|---|---|---|---|---|---|---|---|---|---|---|---|---|---|---|---|---|---|---|---|---|---|---|
| 1 | 45 | F | W | INV.DUCT | 8/97 | Y | ? | A, C | 20YRS | R | 112 | 11–53 | TREND TO TRITAN | | 11/11 | 141(27) | 73(26) | 2.4 | 2315 | 465B | 0.5 log | 20/20 | ND | HVF FULL |
| | | | | | | | | | | L | 120 | 16–58 | TREND TO TRITAN | | 11/11 | 145(27) | 78(26) | 2.8 | 2041 | 438N | | 20/'20 | ND | INFNASAL |
| 2 | 62 | F | W | BREAST | 7/93 | N | ? | NONE | NO | R | 44 | 42–84 | | | 11/11 | 109(27) | 69(27) | 2.07 | 1700 | 461(49) | 0.5 log | 20/25 | NOR | HVF FULL |
| | | | | | | | | | | L | 52 | 2–44 | | | 11/11 | 111(27) | 78(27) | 2.68 | 1550 | 519(70) | 0.5 log | 29/25 | NOR | HVF FULL |
| 3 | 69 | F | W | STAGE IV BREAST | 1995 | Y | Y | C, M, 5-FU, A | YES SEL-DOM | R | 140 | 39–81 | 95% PROBABILITY BINOCULAR ERROR | | 11/11 | 85(28) | 62(28) | 1 | 1380 | 436(65) | 0.5 log | 20/20 | NOR | GVF FULL |
| | | | | | | | | | | L | 208 | 41–83 | | | 10/11(7) | 95(27) | 64(28) | 2 | 1100 | 542(70) | 0.5 log | 20/'20 | NOR | GVF FULL |
| 4 | 57 | F | W | BREAST | 3/97 | Y | Y | CIS T TOP, D | QUIT 1969 | R | 32 | 39–81 | | | 11/11 | 100 | 54 | 3.7 | 1204 | 471 | | 20/20 | NOR | GVF FULL |
| | | | | | | | | | | L | 48 | 40–82 | | | 10/11(16) | 101 | 65 | 2.8 | 1065 | 507 | | 20/'25 | RPEΔ | GVF FULL |
| 5 | 57 | F | W | INF. DUCT | 1994 | Y | Y | NAV | 25YRS | R | 60 | 40–82 | | | 11/11 | 92 | 67 | 3.01 | 1410 | 460 | | 20/20 | RPEΔ | GVF FULL |
| | | | | | | | | | | L | 56 | 38–48 | | | 11/11 | 97 | 69 | 3.09 | 1475 | 440 | | 20/'30 | NOR | GVF FULL |
| 6 | 41 | F | W | INF. | 1994 | N | N | R, 5-FU, C, M | 20+YRS | R | 32 | 31–73 | 95% PROBABILITY BINOCULAR ERROR | | 11/11 | 121 | 78 | 3.4 | 1685 | 337 | | 20/15 | NOR | GVF FULL |
| | | | | | | | | | | L | 84 | 29–71 | | | 11/11 | 130 | 92 | 3.7 | 1726 | 433 | | 20/15 | NOR | GVF FULL |
| 7 | 48 | F | W | LOW RISK | 10/96 | N | N | R, TAM | 15YRS QUIT 89 | R | 60 | 42–84 | | | 11/11 | 95 | 71 | 1.9 | 1751 | 474 | | 20/20 NEAR | NOR | GVF FULL |
| | | | | | | | | | | L | 84 | 42–70 | | | 11/11 | 120 | 88 | 2.7 | 1776 | 526 | | 20/15 NEAR | NOR | GVF FULL |
| 8 | 60 | F | W | BREAST | 93 MET 12/96 | Y | Y | TAXT M 5,FU, AR, P | YES | R | 148 | 21–63 | | | 11/11 | 145 | 86 | 3.6 | 1414 | 708 | | 20/40 | NOR | GVF FULL |
| | | | | | | | | | | L | 112 | 31–73 | | | 11/11 | 150 | 88 | 3.7 | 1642 | 700 | | 20/25 | NOR | GVF FULL |
| 9 | 42 | F | W | INV, TYPE | 7/97 | N | ? | R, C, A | YES | R | 36 | 2–42 | 95% PROBABILITY BINOCULAR ERROR | | 11/11 | 168 | 91 | 1.20 | 1923 | 581 | | 20/20 | NOR | GVF FULL |
| | | | | | | | | | | L | 72 | 6–48 | | | 11/11 | 170 | 88 | 1.29 | 1634 | 680 | | 20/'20 | NOR | GVF FULL |
| 10 | 44 | F | W | INV, DUCT | 6/97 | N | N | R, C, M, 5-FU | YES 23YRS | R | 204 | 38–42 | P<0.01 TRITAN W/ 95% PROBABILITY BINOCULAR ERROR | | 11/11 | 151 | 98 | 2.13 | 2056 | 560 | | 20/15 | NOR | GVF FULL |
| | | | | | | | | | | L | 132 | 22–64 | | | 11/11 | 151 | 87 | 2.50 | 1813 | 595 | | 20/15 | NOR | GVF FULL |
| ABBERANT | | | | VALUES | | | | | | | | | ERG: NORM 33 EYES AGES 9–59 (>2.0 S.D.) | | | 78 | 53 | 1.9 | 1500 | 280 | | | | |

TABLE 3-continued

| SAMPLE FROM BREAST CANCER PATIENT VOLUNTEERS |
|---|
| DATE DIAG = DATE OF DIAGNOSIS;<br>TREATMENT: CIS = CISPLATIN;<br>R = RADIATION;<br>M = METHOTREXATE;<br>C = CYTOXIN:<br>T = TAXOL;<br>TAXT = TAXOTERE;<br>P = PERGIMATE;<br>A = ADRIAMYCIN;<br>D = DDXORUBICIN;<br>TOP = TOPOTECAN;<br>NAV = NAVELBINE;<br>TAM = TAMOXIFIN;<br>TDT = UNDERGOING TREATMENT DATE(S) OF TESTING;<br>COLOR VISION: COLQR OF MAJOR AXIS = CMA;<br>ERG: ELECTRORETINOGRAM (MICROVOLDS P-P);<br>MAC 4° = MACULAR 4°;<br>O.P. = OSCILLITORY POTENTIAL (RMS MICROVOLTS $\times 10^{-2}$;<br>DARK B = SCOTOPIC B WAVE;<br>DARK ADAPTATION: PERFORMED ON GOLDMANN//WEEKERS ADAPTOMETER (HAAG-STREIT);<br>DFE = DILATED FUNDUS EXAM:<br>RPEΔ = MILD RETINAL PIGMENTED EPITHELIAL CHANGES;<br>NOR = NORMAL;<br>DRS = DRUSEN;<br>VISUAL FIELD: HVF = HUMPHRY VISUAL FIELD;<br>GVF = GOLDMANN-VISUAL FIELD;<br>FTCF = FULL TO CONFRONTATION |

APPENDIX

| QUESTIONNAIRE |
|---|

1) Visual Acuity

- Have you noticed any decrease in your vision? (difficulty seeing signs, class, boards, TV, reading, . . .)

☐ No ☐ Yes
- If yes: Which eye? ☐ right ☐ left

Since when did you notice: ______

Was the loss ☐ sudden, or ☐ gradual

Was the loss ☐ permanent; ☐ temporary; or ☐ it comes and goes
- Have you experienced any momentary "total blindness"?

☐ No ☐ Yes
- If yes: Which eye? ☐ right ☐ left

Please describe: ______
- Any other comment related to the above: ______

2) Visual Field

- Have you experienced any loss of peripheral field? (peripheral field means "side vision", peripheral vision, . . .)

☐ No ☐ Yes
- If yes: Which eye? ☐ right ☐ left

Which "side" of vision did you experience this loss" ☐ lower ☐ upper ☐ lateral ☐ don't know
- Have you or someone noticed that you are bumping into chairs, stools, objects, or doors when walking?

☐ No ☐ Yes
- Have you experienced any loss or distortion of your central vision? (an y defect of the "right straight" vision), noticeable more when reading?

☐ No ☐ Yes
- If yes: Which eye? ☐ right ☐ left

Please describe: ______
- Any other comment related to the above: ______

3) Night Blindness

- Can you "see" well in semi-darkness, when there is low light?

☐ No ☐ Yes
- Do you bump into "things" more often when the room is slightly dim mer?

☐ No ☐ Yes
- Do you have troble driving at night?

☐ No ☐ Yes
- Do you recover your "night vision" after a car (with its headlights on) passes you?

☐ No ☐ Yes
- Do you like to drive at night?

☐ No ☐ Yes
- Do oncoming lights from cars or street lights affect your ability to dri ve?

☐ No ☐ Yes
- Have you experienced being "completely blind" where other people still can see in a semi-dark room, where there is low light?

☐ No ☐ Yes
- Any other comment related to the above: ______

APPENDIX-continued

QUESTIONNAIRE

4) Color Vision

- Have you been having difficulties distinguishing colors?

☐ No ☐ Yes

- If yes: Which colors? ______
  Since when ? ______
  Do they look dimmer? ______
  Do they look brighter? ______
- Do you have trouble seeing the red and green traffic lights?

☐ No ☐ Yes
- Any other comment related to the above: ______

5) Floaters and Flashes

- Have you been noticing floaters in your eyes? (floaters mean "clumps", "bugs", "points", . . . )

☐ No ☐ Yes
- If yes: Which eye? ☐ right ☐ left
  How long have you noticed them?
- Do you "see" flashing lights? (light that you "see" but are not real lights, and you "see" even when your eyes are closed)

☐ No ☐ Yes
- If yes: Which eye? ☐ right ☐ left
  How often: ______
- Any other comment related to the above: ______

6) Past Ocular History (known/previous eye disorders)

- Were you ever told you had an eye condition?

☐ No ☐ Yes
- Were you ever treated or operated on for an eye condition?

☐ No ☐ Yes
- If yes on any of the above questions, what condition?

☐ Cataract ☐ right ☐ left
  Surgery? ☐ No ☐ Yes
  When? ______

☐ Glaucoma ☐ right ☐ left
  Treatment: ☐ laser ☐ surgery
  Since When? ______

☐ Retinal tear/Hole ☐ right ☐ left
  Treatment: ☐ laser ☐ surgery

☐ Retinal Detachment ☐ right ☐ left
  Treatment: ☐ laser ☐ surgery

☐ Uveitis/Chorioretinitis ☐ right ☐ left
  Treatment: ☐ laser ☐ surgery ☐ medical ☐ Optic Nerve Diseases (including inflammation, "stroke", tumors . . . )
  ☐ right ☐ left
  Since When? ______
  Treatment? ______
- ☐ Others ("lazy eye", "crossed eyes", macular degeneration, trauma/injury, etc.):
  ______
- Any other comment related to the above: ______

APPENDIX-continued

QUESTIONNAIRE

7) Eye Doctor

- Do you visit an Eye Doctor on a regular basis?

☐ No ☐ Yes

If yes: how often?

- When was the last time you visited an Eye Doctor? ____________________
- Please give the name of your Eye Doctor/or the last one you visited, and location of his/her practice:

Name: ________________________________________

City/State: ____________________________________

8) Please feel free to make any comment that you believe will add to the understanding of your eye problem(s):

9) RISK FACTORS TO VISUAL HEALTH:

SMOKER (brand, packs/day, # years)?

OCCUPATIONAL RISKS?

FAMILY HISTORY OF DISEASE(S)?

To be filled our by nursing personnel:

I. Near visual acuity (Vision card, with glasses):

Right Eye: Left Eye:

II. Color Plates:

Right Eye: Left Eye:

III. Confrontation Visual Fields (as patient sees):

Right Eye: Left Eye:

What is claimed is:

1. A method for the detection of cancer in a patient who does not have CAR, wherein said method comprises evaluating said patient to determine whether said patient has at least one retinal deficit which does not cause a significant loss of visual acuity; and wherein the presence of said retinal deficit is correlated with the presence of cancer in said patient.

2. The method, according to claim 1, wherein said method comprises administering at least one of the following:

a) a color vision test;

b) a dark adaptation test;

c) an EEG; and d) an ERG.

3. The method, according to claim 2, wherein said method further comprises administering a questionnaire concerning the vision of the patient.

4. The method, according to claim 1, wherein the cancer which is detected is selected from the group consisting of testicular, prostate, ovarian, breast, respiratory tract, digestive tract, urinary tract, skin, tumors of internal organs including reproductive organs, and metastatic tumors.

5. The method, according to claim 1, wherein said retinal deficit is not entirely attributable to a condition selected from the group consisting of glaucoma, diabetic retinopathy, and retinitis pigmentosa.

6. The method, according to claim 1, which comprises a standard eye examination.

7. The method, according to claim 1, wherein a diagnosis of visual abnormality is not solely due to causes other than cancer, and wherein said method further comprises referral to an oncological specialist for diagnosis or monitoring of cancer.

8. A method for the detection of cancer in a patient wherein said method comprises evaluating said patient to determine whether said patient has at least one retinal deficit which does not cause a significant loss of visual acuity; wherein the presence of said retinal deficit is correlated with the presence of cancer in said patient; and wherein said retinal deficit is manifested in at least one way selected from the group consisting of:

a) a loss of dark adaptation;

b) a defect in color vision;

c) an abnormality in the ERG; and d) an abnormality in the EEG.

9. The method, according to claim 8, wherein said loss of dark adaptation is detected by measurement of adaptation to light stimulus in the dark over a period of time.

10. The method, according to claim 8, wherein said defect in color vision produces an abnormal axis in the Farnsworth-Munsell 100 Hue color test, a variation of the test, or a color equivalency testing method.

11. The method, according to claim 8, wherein said defect in color vision produces an abnormal score in the Farnsworth-Munsell 100 Hue color test, a variation of the test, or a color equivalency testing method.

12. The method, according to claim 8, wherein said defect in color vision is a tritan defect.

13. The method, according to claim 8, wherein said defect in color vision is a tetaran defect.

14. The method, according to claim 8, wherein said defect in color vision is an unclassified defect.

15. The method, according to claim 8, wherein said defect in color vision is not a genetic binocular protan or deutan defect.

16. The method, according to claim 8, wherein said defect in color vision is showing no axis for the analysis of color vision.

17. The method, according to claim 8, wherein said defect in color vision is determined by axis, even when error score is not aberrant.

18. The method, according to claim 8, wherein said defect in color vision is determined by a monocular defect, where one eye exhibits an error significantly different from the other eye.

19. The method, according to claim 8, wherein said abnormality in the ERG appears as a reduction in signal below a norm.

20. The method, according to claim 8, wherein said deficit is manifested as an abnormality in the EEG.

21. A method for the detection of cancer in a patient wherein said method comprises evaluating said patient to determine whether said patient has at least one retinal deficit which does not cause a significant loss of visual acuity; and wherein said patient does not have CAR; wherein the presence of said retinal deficit is correlated with the presence of cancer in said patient; and wherein said method comprises the administration of psychophysical tests.

22. The method, according to claim 21, wherein said pyschophysical tests evaluate at least one parameter selected from the group consisting of:

a) color responsiveness;

b) contrast; and c) adaptability to light in the dark.

23. A method for detection of cancer in a patient wherein said method comprises detection in said patient of a toxic factor which interacts with neural cells, wherein said toxic factor causes damage to brain or retina cells, and wherein said damage to retina cells does not substantially reduce visual acuity but does result in at least one of the group consisting of the following:

a) a loss of dark adaptation;

b) a defector deficit in color vision;

c) an abnormality in the ERG; and d) an abnormality in the EEG.

24. The method, according to claim 23, wherein said toxic factor is selected from the group consisting of antibodies, cytokines, hormones, and other proteins.

25. A method for monitoring the progression of a cancerous condition and/or the efficacy of treatment thereof, wherein said method comprises monitoring changes in retinal deficits associated with CARD, wherein said method comprises monitoring at least one parameter selected from the group consisting of:

a) dark adaption;

b) color vision;

c) ERG; and d) EEG.

26. A kit for the detection of cancer wherein said kit comprises at least two of the following:

a) dark adaptation test materials;

b) color vision test materials;

c) ERG test materials;

d) EEG test materials; and e) a vision questionnaire.

27. A method for the detection of cancer in a patient wherein said method comprises determining whether the serum of said patient has antibodies to a protein of 30 kD when said antibodies bind to neural cells.

28. The method, according to claim 27, wherein said cells are brain cells or retina cells.

* * * * *